United States Patent
Andre et al.

(10) Patent No.: US 12,134,642 B2
(45) Date of Patent: Nov. 5, 2024

(54) ANTIBODIES BINDING TO α7β1 INTEGRIN ANTIBODIES AND COMPOSITIONS THEREOF

(71) Applicant: Pliant Therapeutics, Inc., South San Francisco, CA (US)

(72) Inventors: Patrick Andre, Short Hills, NJ (US); Chun Chen, Albany, CA (US); Scott Turner, Oakland, CA (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 155 days.

(21) Appl. No.: 17/098,199

(22) Filed: Nov. 13, 2020

(65) Prior Publication Data

US 2021/0147526 A1    May 20, 2021

Related U.S. Application Data

(60) Provisional application No. 63/029,070, filed on May 22, 2020, provisional application No. 63/009,020, filed on Apr. 13, 2020, provisional application No. 62/935,732, filed on Nov. 15, 2019.

(51) Int. Cl.

| | |
|---|---|
| *C07K 16/18* | (2006.01) |
| *A61K 39/00* | (2006.01) |
| *A61K 39/395* | (2006.01) |
| *A61K 45/06* | (2006.01) |
| *A61P 25/28* | (2006.01) |
| *C07K 16/00* | (2006.01) |
| *C07K 16/28* | (2006.01) |

(52) U.S. Cl.
CPC .............. *C07K 16/18* (2013.01); *A61K 45/06* (2013.01); *A61P 25/28* (2018.01); *A61K 2039/505* (2013.01)

(58) Field of Classification Search
CPC .... A61K 2039/505; A61P 29/00; A61P 25/00; A61P 21/00
See application file for complete search history.

(56) References Cited

U.S. PATENT DOCUMENTS

| | | | |
|---|---|---|---|
| 4,522,811 | A | 6/1985 | Eppstein |
| 4,816,397 | A | 3/1989 | Boss |
| 4,816,567 | A | 3/1989 | Cabilly |
| 4,975,369 | A | 12/1990 | Beavers et al. |
| 4,978,775 | A | 12/1990 | Ikegami et al. |
| 5,225,539 | A | 7/1993 | Winter |
| 5,530,101 | A | 6/1996 | Queen |
| 5,585,089 | A | 12/1996 | Queen |
| 5,693,761 | A | 12/1997 | Queen |
| 5,693,762 | A | 12/1997 | Queen |
| 5,985,278 | A | 11/1999 | Mitjans |
| 6,180,370 | B1 | 1/2001 | Queen et al. |
| 6,858,395 | B2 | 2/2005 | Kaufman |
| 2021/0147526 | A1 | 5/2021 | Andre et al. |

FOREIGN PATENT DOCUMENTS

| | | |
|---|---|---|
| RU | 2205223 C2 | 5/2003 |
| WO | 199005144 A1 | 5/1990 |
| WO | 199007861 A1 | 7/1990 |

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-42.*
Holm et al., Mol. Immunol., 2007; 44: 1075-1084.*
Chen et al.,J. Mol. Bio., 1999; 293: 865-881.*
Wu et al.,J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
Shober et al., Exp. Cell Res. 2000; 255:303-313.*
Von Der Mark et al.,J. Mol. Biol., 2007; 371:1188-1203.*
Mielenz et al., J. Biol. Chem. 2001; 276:13417-13426.*
Von Mehren et al., Curr. Opin. Oncol. 1996. 8: 493-8.*
Abcam (2018). Anti-ITGA7 antibody [3C12] ab195959, Product datasheet, 4 total pages.
Belkin, A.M. et al. (2000). "Integrins as receptors for Laminins," Microscopy Res. and Technique 51:280-301.
Boppart, M.D. et al. (2019). "Integrin signaling: Linking mechanical stimulation to skeletal muscle hypertrophy," A. J. Physiol. Cell Physiol. 317:C629-C641.
Burkin, D.J. et al. (2001). "Enhanced expression of the α7β1 integrin reduces muscular dystrophy and restores viability in dystrophic mice," J. Cell Biol. 152:1207-1218.
Engl, T. et al. (2018). "Acquired resistance to temsirolimus is associated with integrin α7 driven chemotactic activity of renal cell carcinoma in vitro," Oncotarget 9:18747-18759. 18747-18759.
Hodges, B.L. et al. (1997). "Altered expression of the α7β1 integrin in human and murine muscular dystrophies," J. Cell Sci. 110:2873-2881.
International Search Report and Written Opinion mailed on Mar. 2, 2021, for PCT Application No. PCT/US2020/060574, filed on Nov. 13, 2020, 21 pages.
Mayer, U. et al. (1997). "Absence of integrin α7 causes a novel form of muscular dystrophy," Nature Genetics 17:318-323.
Sarathy, A. et al. (2017). "SU9516 increase a7β1 integrin and ameliorates disease progression in the mdx mouse model of Duchenne muscular dystrophy," Mol. Ther. 25:1395-1407.

(Continued)

*Primary Examiner* — Chang-Yu Wang
(74) *Attorney, Agent, or Firm* — Morrison & Foerster LLP; Kraig Anderson; Johannes Hull

(57) ABSTRACT

Disclosed herein are pharmaceutical agents and compositions that activate integrin heterodimers that contain beta-1 integrin protein that specifically bind laminin protein. Such agents and compositions are useful for treating diseases related to muscle malfunction, including muscular dystrophies.

15 Claims, 27 Drawing Sheets

Specification includes a Sequence Listing.

(56) References Cited

OTHER PUBLICATIONS

Yucel, N. et al. (2018). "Humanizing the mdx mouse model of DMD: The long and the short of it," Regen. Med. 3:4, 11 total pages.
Bazzoni, G. et al. (Oct. 27, 1995). "Monoclonal Antibody 9EG7 Defines a Novel β1 Integrin Epitope Induced by Soluble Ligand and Manganese, but Inhibited by Calcium," J. Biol. Chem. 270(43):25570-25577.
Bird, R.E. et al. (Oct. 21, 1988). "Single-Chain Antigen-Binding Proteins," Science 242(4877):423-426.
Bogan, A.A. et al. (1998). "Anatomy of Hot Spots in Protein Interfaces," J. Mol. Biol. 280:1-9.
Davidson, E. et al. (2014). "A High-Throughput Shotgun Mutagenesis Approach to Mapping B-Cell Antibody Epitopes," Immunology 143:13-20.
Davies, D.R. et al. (1990). "Antibody-Antigen Complexes," Annual Rev. Biochem. 59:439-473.
Gao, S.H. et al. (2013). "Monoclonal Antibody Humanness Score and its Applications," BMC Biotechnology 13:55, 12 pages.
Hemler, M.E. et al. (Jun. 1984). "Glycoproteins of 210,000 and 130,000 M.W. on Activated T Cells: Cell Distribution and Antigenic Relation to Components on Resting Cells and T Cell Lines," J. Immunol. 132(6):3011-3018.
Holliger, P. et al. (Jul. 1993). ""Diabodies": Small Bivalent and Bispecific Antibody Fragments," Proceedings of the National Academy of Sciences USA 90:6444-6448.
Huston, J.S. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
Hiwang, W.Y.K. et al. (2005). "Use of Human Germline Genes in a CDR Homology-Based Approach to Antibody Humanization," Methods 36: 35-42.
Hynes, R.O. (Sep. 20, 2002). "Integrins: Bidirectional Allosteric Signaling Machines," Cell 110:673-687.
International Preliminary Report on Patentability, issued May 17, 2022, for PCT Application No. PCT/US2020/060574, iled Nov. 13, 2022, 10 pages.
Jones, P. et al. (May 29, 1986). "Replacing The Complementarity-Determining Regions in a Human Antibody With Those From a Mouse," Nature 321:522-525.
Kontermann, R.E. et al. (2001). Antibody Engineering, TOC, vol. 1 and vol. 2, 60 pages.
Lo Conte, L. et al. (1999). "The Atomic Structure of Protein-Protein Recognition Sites," J. Mol. Biol. 285:2177-2198.
Malmqvist, M. (Jan. 14, 1993). "Biospecific Interaction Analysis Using Biosensor Technology," Nature 361(6408):186-187.
Myers, E.W. et al. (1988). "Optimal Alignments in Linear Space," CABIOS 4(1):11-17.
Needleman, S. B. et al. (1970). "A General Method Applicable to the Search for Similarities in the Amino Acid sequence of Two Proteins," J. Mol. Biol. 48:443-453.
Orlandi, R. et al. (May 1989). "Cloning Immunoglobulin Variable Domains for Expression by the Polymerase Chain Reaction," Proc. Natl. Acad. Sci. USA 86(10):3833-3837.
Poljak, R.J. (Dec. 15, 1994). "Production and Structure of Diabodies," Structure 2(12):1121-1123.
Queen, C. et al. (Dec. 1989). "A Humanized Antibody That Binds to the Interleukin 2 Receptor," Proc. Natl Acad. Sci. USA 86:10029-10033.
Riechmann, L. et al. (Mar. 24, 1988). "Reshaping Human Antibodies for Therapy," Nature 332:323-329.
Seno, M.M.G. et al. (Sep. 1, 2008, e-pub. May 28, 2008). "RNAi-Mediated Knockdown of Dystrophin Expression in Adult Mice Does Not Lead to Overt Muscular Dystrophy Pathology," Human Molecular Genetics 17(17):2622-2632.
Verhoeyen, M. et al. (Mar. 25, 1988). "Reshaping Human Antibodies: Grafting an Antilysozyme Activity," Science 239:1534-1536.
Ward, E.S. et al. (1995). "The Effector Functions of Immunoglobulins: Implications for Therapy," Ther. Immunol., 2:77-94.
Ward, E.S. et al. (Oct. 12, 1989). "Binding Activities of a Repertoire of Single Immunoglobulin Variable Domains Secreted From *Escherichia coli*," Nature 341(6242): 544-546.
Xiao, J. et al. (Dec. 12. 2003). "Regulation of β7 Integrin Expression During Muscle Differentiation," J. Biol. Chem. 278(50):49780-49788.
Xie, C. et al. (2010). "Structure of an Integrin with an αI Domain, Complement Receptor Type 4," EMBO. J. 29(3):666-679.
Yaffe, D. et al. (Dec. 22-29, 1977). "Serial Passaging and Differentiation of Myogenic Cells Isolated from Dystrophic Mouse Muscle," Nature 270(5639):725-727.
Yao, C.-C. et al. (Dec. 1996). "Laminins Promote the Locomotion of Skeletal Myoblasts via the alpha 7 Integrin Receptor," J. Cell Sci. 109(pt. 13):3139-3150.
Bulfield et al., "X chromosome-linked muscular dystrophy (mdx) in the mouse," PNAS 81(4):1189-1192 (1984).
Duggan et al., "Mutations in the Sarcoglycan Genes in Patients with Myopathy," NEJM 336:618-625 N Engl J Med (1997).
Elsherif et al., "Combined Deficiency of Dystrophin and β1 Integrin in the Cardiac Myocyte Causes Myocardial Dysfunction, Fibrosis and Calcification," Circulation Research 102:1109-1117 (2008).
Guo et al., "Absence of α7 integrin in dystrophin-deficient mice causes a myopathy similar to Duchenne muscular dystrophy," Human Molecular Genetics 15(6):989-998 (2006).
Hayashi et al., "Mutations in the integrin α7 gene cause congenital myopathy," Nat Genetics 19:94-97 (1998).
Helbling-Leclerc et al., "Mutations in the laminin α2-chain gene (LAMA2) cause merosin-deficient congenital muscular dystrophy," Nature Genetics 11:216-218 (1995).
Rooney et al., "Severe muscular dystrophy in mice that lack dystrophin and α7 integrin," J Cell Sci 119: 2185-2195 (2006).
UniProt ID: Q13683.3 (Apr. 2021). "ITA7_Human," 9 pages.
Kwon, M.S. et al. (Apr. 2000). "Calreticulin Couples Calcium Release And Calcium Influx In Integrin-mediated Calcium Signaling," Molecular Biology of the Cell 11(4):1433-1443.
Badri, H. et al. (2016, e-pub. Jun. 21, 2015). "Optimization Of Radiation Dosing Schedules For Proneural Glioblastoma," J Math Biol. 72(5):1301-1336, 36 pages.
Baylot, V. et al. (2017). "TCTP Has A Crucial Role In The Different Stages Of Prostate Cancer Malignant Progression," Chapter 13 in TCTP/tpt1-Remodeling Signaling From Stem Cell To Disease, Telerman, A. et al. eds., Springer International Publishing: Cham, Switzerland, pp. 255-261.
Kussie, P.H. et al. (1994). "A Single Engineered Amino Acid Substitution Changes Antibody Fine Specificity ," J. Immunol. 152:146-152.
Mariuzza, R.A. et al. (1987). "The Structural Basis Of Antigen-Antibody Recognition," Annu. Rev. Biophys. Biophys. Chem. 16:139-159.
Muller, S. et al. (Dec. 2008). "Spliceosomal Peptide P140 for Immunotherapy of Systemic Lupus Erythematosus: Results of an Early Phase II Clinical Trial," Arthritis & Rheumatism: Official Journal of the American College of Rheumatology 58(12):3873-3883.

\* cited by examiner

X1: TARVELCAQGSADLAHLDDGPYEAGGEKEQDPRLIPVPANSYFG (SEQ ID NO: 1)
X2: LLFVTNIDSSDPDQLVYKTLDPADRLPGPAGDLALNSYLG (SEQ ID NO: 10)

SEQUENCE LISTING

```
<160> NUMBER OF SEQ ID NOS: 87

<210> SEQ ID NO 1
<211> LENGTH: 44
<212> TYPE: PRT
<213> ORGANISM: Homo sapiens

<400> SEQUENCE: 1

Thr Ala Arg Val Glu Leu Cys Ala Gln Gly Ser Ala Asp Leu Ala His
1               5                   10                  15

Leu Asp Asp Gly Pro Tyr Glu Ala Gly Gly Glu Lys Glu Gln Asp Pro
            20                  25                  30

Arg Leu Ile Pro Val Pro Ala Asn Ser Tyr Phe Gly
        35                  40
```

```
<210> SEQ ID NO 2
<211> LENGTH: 8
<212> TYPE: PRT
<213> ORGANISM: Mus musculus

<400> SEQUENCE: 2

Gly Tyr Asn Phe Thr Lys Tyr Trp
1               5

<210> SEQ ID NO 3
<211> LENGTH: 8
<212> TYPE: PRT
<213> ORGANISM: Mus musculus

<400> SEQUENCE: 3

Ile Tyr Pro Gly Ser Ser Thr Ser
1               5

<210> SEQ ID NO 4
<211> LENGTH: 5
<212> TYPE: PRT
<213> ORGANISM: Mus musculus

<400> SEQUENCE: 4

Val Arg Gly Asp Asp
1               5

<210> SEQ ID NO 5
<211> LENGTH: 10
<212> TYPE: PRT
<213> ORGANISM: Mus musculus

<400> SEQUENCE: 5

Glu Ser Val Asp Asn Tyr Gly Ile Ser Phe
1               5                   10

<210> SEQ ID NO 6
<211> LENGTH: 3
<212> TYPE: PRT
<213> ORGANISM: Mus musculus

<400> SEQUENCE: 6

Ala Ala Ser
1

<210> SEQ ID NO 7
<211> LENGTH: 9
<212> TYPE: PRT
<213> ORGANISM: Mus musculus

<400> SEQUENCE: 7

His Gln Ser Lys Glu Val Pro Tyr Thr
1               5

<210> SEQ ID NO 8
<211> LENGTH: 112
<212> TYPE: PRT
<213> ORGANISM: Mus musculus

<400> SEQUENCE: 8

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Asn Phe Thr Lys Tyr
            20                  25                  30
```

```
Trp Ile Asn Trp Val Lys Gln Arg Pro Gly Gln Gly Leu Glu Trp Ile
             35                  40                  45

Gly Ile Ile Tyr Pro Gly Ser Ser Thr Ser Asn Tyr Asn Glu Lys Phe
 50                      55                  60

Lys Thr Lys Ala Thr Leu Thr Val Glu Ile Ser Ser Thr Thr Ala Tyr
 65                  70                  75                  80

Met Gln Leu Ser Ser Leu Thr Ser Asp Asp Ser Ala Val Tyr Tyr Cys
                 85                  90                  95

Val Arg Gly Asp Asp Trp Gly Gln Gly Thr Thr Leu Thr Val Ser Ser
            100                 105                 110

<210> SEQ ID NO 9
<211> LENGTH: 111
<212> TYPE: PRT
<213> ORGANISM: Mus musculus

<400> SEQUENCE: 9

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Asn Tyr
             20                  25                  30

Gly Ile Ser Phe Met Asn Trp Phe Gln Gln Lys Pro Gly Gln Pro Pro
         35                  40                  45

Lys Leu Leu Ile Tyr Ala Ala Ser Asp Leu Gly Ser Gly Val Pro Ala
 50                  55                  60

Arg Phe Thr Gly Ser Gly Ser Gly Thr Asp Phe Ser Leu Asn Ile His
 65                  70                  75                  80

Pro Met Glu Glu Asp Asp Ser Ala Met Tyr Phe Cys His Gln Ser Lys
                 85                  90                  95

Glu Val Pro Tyr Thr Phe Gly Gly Gly Thr Lys Leu Glu Ile Lys
            100                 105                 110

<210> SEQ ID NO 10
<211> LENGTH: 40
<212> TYPE: PRT
<213> ORGANISM: Homo sapiens

<400> SEQUENCE: 10

Leu Leu Phe Val Thr Asn Ile Asp Ser Ser Asp Pro Asp Gln Leu Val
  1               5                  10                  15

Tyr Lys Thr Leu Asp Pro Ala Asp Arg Leu Pro Gly Pro Ala Gly Asp
             20                  25                  30

Leu Ala Leu Asn Ser Tyr Leu Gly
         35                  40

<210> SEQ ID NO 11
<211> LENGTH: 446
<212> TYPE: PRT
<213> ORGANISM: Homo sapiens

<400> SEQUENCE: 11

Phe Asn Leu Asp Val Met Gly Ala Leu Arg Lys Glu Gly Glu Pro Gly
  1               5                  10                  15

Ser Leu Phe Gly Phe Ser Val Ala Leu His Arg Gln Leu Gln Pro Arg
             20                  25                  30

Pro Gln Ser Trp Leu Leu Val Gly Ala Pro Gln Ala Leu Ala Leu Pro
         35                  40                  45

Gly Gln Gln Ala Asn Arg Thr Gly Gly Leu Phe Ala Cys Pro Leu Ser
```

```
                50                  55                  60
Leu Glu Glu Thr Asp Cys Tyr Arg Val Asp Ile Asp Gln Gly Ala Asp
 65                  70                  75                  80

Met Gln Lys Glu Ser Lys Glu Asn Gln Trp Leu Gly Val Ser Val Arg
                 85                  90                  95

Ser Gln Gly Pro Gly Gly Lys Ile Val Thr Cys Ala His Arg Tyr Glu
            100                 105                 110

Ala Arg Gln Arg Val Asp Gln Ile Leu Glu Thr Arg Asp Met Ile Gly
        115                 120                 125

Arg Cys Phe Val Leu Ser Gln Asp Leu Ala Ile Arg Asp Glu Leu Asp
    130                 135                 140

Gly Gly Glu Trp Lys Phe Cys Glu Gly Arg Pro Gln Gly His Glu Gln
145                 150                 155                 160

Phe Gly Phe Cys Gln Gln Gly Thr Ala Ala Phe Ser Pro Asp Ser
                165                 170                 175

His Tyr Leu Leu Phe Gly Ala Pro Gly Thr Tyr Asn Trp Lys Gly Thr
                180                 185                 190

Ala Arg Val Glu Leu Cys Ala Gln Gly Ser Ala Asp Leu Ala His Leu
            195                 200                 205

Asp Asp Gly Pro Tyr Glu Ala Gly Glu Lys Glu Gln Asp Pro Arg
        210                 215                 220

Leu Ile Pro Val Pro Ala Asn Ser Tyr Phe Gly Phe Ser Ile Asp Ser
225                 230                 235                 240

Gly Lys Gly Leu Val Arg Ala Glu Glu Leu Ser Phe Val Ala Gly Ala
                245                 250                 255

Pro Arg Ala Asn His Lys Gly Ala Val Val Ile Leu Arg Lys Asp Ser
                260                 265                 270

Ala Ser Arg Leu Val Pro Glu Val Met Leu Ser Gly Glu Arg Leu Thr
            275                 280                 285

Ser Gly Phe Gly Tyr Ser Leu Ala Val Ala Asp Leu Asn Ser Asp Gly
        290                 295                 300

Trp Pro Asp Leu Ile Val Gly Ala Pro Tyr Phe Phe Glu Arg Gln Glu
305                 310                 315                 320

Glu Leu Gly Gly Ala Val Tyr Val Tyr Leu Asn Gln Gly Gly His Trp
                325                 330                 335

Ala Gly Ile Ser Pro Leu Arg Leu Cys Gly Ser Pro Ser Met Phe
            340                 345                 350

Gly Ile Ser Leu Ala Val Leu Gly Asp Leu Asn Gln Asp Gly Phe Pro
        355                 360                 365

Asp Ile Ala Val Gly Ala Pro Phe Asp Gly Asp Gly Lys Val Phe Ile
    370                 375                 380

Tyr His Gly Ser Ser Leu Gly Val Val Ala Lys Pro Ser Gln Val Leu
385                 390                 395                 400

Glu Gly Glu Ala Val Gly Ile Lys Ser Phe Gly Tyr Ser Leu Ser Gly
                405                 410                 415

Ser Leu Asp Met Asp Gly Asn Gln Tyr Pro Asp Leu Leu Val Gly Ser
            420                 425                 430

Leu Ala Asp Thr Ala Val Leu Phe Arg Ala Arg Pro Ile Leu
        435                 440                 445

<210> SEQ ID NO 12
<211> LENGTH: 445
<212> TYPE: PRT
<213> ORGANISM: Homo sapiens
```

<400> SEQUENCE: 12

```
Phe Asn Leu Asp Thr Arg Glu Asp Asn Val Ile Arg Lys Tyr Gly Asp
1               5                   10                  15

Pro Gly Ser Leu Phe Gly Phe Ser Leu Ala Met His Trp Gln Leu Gln
            20                  25                  30

Pro Glu Asp Lys Arg Leu Leu Leu Val Gly Ala Pro Arg Ala Glu Ala
        35                  40                  45

Leu Pro Leu Gln Arg Ala Asn Arg Thr Gly Gly Leu Tyr Ser Cys Asp
    50                  55                  60

Ile Thr Ala Arg Gly Pro Cys Thr Arg Ile Glu Phe Asp Asn Asp Ala
65                  70                  75                  80

Asp Pro Thr Ser Glu Ser Lys Glu Asp Gln Trp Met Gly Val Thr Val
                85                  90                  95

Gln Ser Gln Gly Pro Gly Gly Lys Val Val Thr Cys Ala His Arg Tyr
            100                 105                 110

Glu Lys Arg Gln His Val Asn Thr Lys Gln Glu Ser Arg Asp Ile Phe
        115                 120                 125

Gly Arg Cys Tyr Val Leu Ser Gln Asn Leu Arg Ile Glu Asp Asp Met
    130                 135                 140

Asp Gly Gly Asp Trp Ser Phe Cys Asp Gly Arg Leu Arg Gly His Glu
145                 150                 155                 160

Lys Phe Gly Ser Cys Gln Gln Gly Val Ala Ala Thr Phe Thr Lys Asp
                165                 170                 175

Phe His Tyr Ile Val Phe Gly Ala Pro Gly Thr Tyr Asn Trp Lys Gly
            180                 185                 190

Ile Val Arg Val Glu Gln Lys Asn Asn Thr Phe Phe Asp Met Asn Ile
        195                 200                 205

Phe Glu Asp Gly Pro Tyr Glu Val Gly Gly Glu Thr Glu His Asp Glu
    210                 215                 220

Ser Leu Val Pro Val Pro Ala Asn Ser Tyr Leu Gly Phe Ser Leu Asp
225                 230                 235                 240

Ser Gly Lys Gly Ile Val Ser Lys Asp Glu Ile Thr Phe Val Ser Gly
                245                 250                 255

Ala Pro Arg Ala Asn His Ser Gly Ala Val Val Leu Leu Lys Arg Asp
            260                 265                 270

Met Lys Ser Ala His Leu Leu Pro Glu His Ile Phe Asp Gly Glu Gly
        275                 280                 285

Leu Ala Ser Ser Phe Gly Tyr Asp Val Ala Val Asp Leu Asn Lys
    290                 295                 300

Asp Gly Trp Gln Asp Ile Val Ile Gly Ala Pro Gln Tyr Phe Asp Arg
305                 310                 315                 320

Asp Gly Glu Val Gly Gly Ala Val Tyr Val Tyr Met Asn Gln Gln Gly
                325                 330                 335

Arg Trp Asn Asn Val Lys Pro Ile Arg Leu Asn Gly Thr Lys Asp Ser
            340                 345                 350

Met Phe Gly Ile Thr Val Lys Asn Ile Gly Asp Ile Asn Gln Asp Gly
        355                 360                 365

Tyr Pro Asp Ile Ala Val Gly Ala Pro Tyr Asp Asp Leu Gly Lys Val
    370                 375                 380

Phe Ile Tyr His Gly Ser Ala Asn Gly Ile Asn Thr Lys Pro Thr Gln
385                 390                 395                 400

Val Leu Lys Gly Ile Ser Pro Tyr Phe Gly Tyr Ser Ile Ala Gly Asn
```

```
                       405                 410                 415
Met Asp Leu Asp Arg Asn Ser Tyr Pro Asp Val Ala Val Gly Ser Leu
                   420                 425                 430

Ser Asp Ser Val Thr Ile Phe Arg Ser Arg Pro Val Ile
               435                 440                 445

<210> SEQ ID NO 13
<211> LENGTH: 434
<212> TYPE: PRT
<213> ORGANISM: Homo sapiens

<400> SEQUENCE: 13

Phe Asn Leu Asp Thr Arg Phe Leu Val Val Lys Glu Ala Gly Asn Pro
1               5                   10                  15

Gly Ser Leu Phe Gly Tyr Ser Val Ala Leu His Arg Gln Thr Glu Arg
            20                  25                  30

Gln Gln Arg Tyr Leu Leu Leu Ala Gly Ala Pro Arg Glu Leu Ala Val
        35                  40                  45

Pro Asp Gly Tyr Thr Asn Arg Thr Gly Ala Val Tyr Leu Cys Pro Leu
    50                  55                  60

Thr Ala His Lys Asp Asp Cys Glu Arg Met Asn Ile Thr Val Lys Asn
65                  70                  75                  80

Asp Pro Gly His His Ile Ile Glu Asp Met Trp Leu Gly Val Thr Val
                85                  90                  95

Ala Ser Gln Gly Pro Ala Gly Arg Val Leu Val Cys Ala His Arg Tyr
            100                 105                 110

Thr Gln Val Leu Trp Ser Gly Ser Glu Asp Gln Arg Arg Met Val Gly
        115                 120                 125

Lys Cys Tyr Val Arg Gly Asn Asp Leu Glu Leu Asp Ser Ser Asp Asp
    130                 135                 140

Trp Gln Thr Tyr His Asn Glu Met Cys Asn Ser Asn Thr Asp Tyr Leu
145                 150                 155                 160

Glu Thr Gly Met Cys Gln Leu Gly Thr Ser Gly Gly Phe Thr Gln Asn
                165                 170                 175

Thr Val Tyr Phe Gly Ala Pro Gly Ala Tyr Asn Trp Lys Gly Asn Ser
            180                 185                 190

Tyr Met Ile Gln Arg Lys Glu Trp Asp Leu Ser Glu Tyr Ser Tyr Lys
        195                 200                 205

Asp Pro Glu Asp Gln Gly Asn Leu Tyr Ile Gly Tyr Thr Met Gln Val
    210                 215                 220

Gly Ser Phe Ile Leu His Pro Lys Asn Ile Thr Ile Val Thr Gly Ala
225                 230                 235                 240

Pro Arg His Arg His Met Gly Ala Val Phe Leu Leu Ser Gln Glu Ala
                245                 250                 255

Gly Gly Asp Leu Arg Arg Arg Gln Val Leu Glu Gly Ser Gln Val Gly
            260                 265                 270

Ala Tyr Phe Gly Ser Ala Ile Ala Leu Ala Asp Leu Asn Asn Asp Gly
        275                 280                 285

Trp Gln Asp Leu Leu Val Gly Ala Pro Tyr Tyr Phe Glu Arg Lys Glu
    290                 295                 300

Glu Val Gly Gly Ala Ile Tyr Val Phe Met Asn Gln Ala Gly Thr Ser
305                 310                 315                 320

Phe Pro Ala His Pro Ser Leu Leu Leu His Gly Pro Ser Gly Ser Ala
                325                 330                 335
```

Phe Gly Leu Ser Val Ala Ser Ile Gly Asp Ile Asn Gln Asp Gly Phe
            340                 345                 350

Gln Asp Ile Ala Val Gly Ala Pro Phe Glu Gly Leu Gly Lys Val Tyr
            355                 360                 365

Ile Tyr His Ser Ser Ser Lys Gly Leu Leu Arg Gln Pro Gln Gln Val
            370                 375                 380

Ile His Gly Glu Lys Leu Gly Leu Pro Gly Leu Ala Thr Phe Gly Tyr
385                 390                 395                 400

Ser Leu Ser Gly Gln Met Asp Val Asp Glu Asn Phe Tyr Pro Asp Leu
                405                 410                 415

Leu Val Gly Ser Leu Ser Asp His Ile Val Leu Leu Arg Ala Arg Pro
            420                 425                 430

Val Ile

<210> SEQ ID NO 14
<211> LENGTH: 8
<212> TYPE: PRT
<213> ORGANISM: Artificial Sequence
<220> FEATURE:
<223> OTHER INFORMATION: humanized antibody VL3VHK20TFT HCDR1

<400> SEQUENCE: 14

Gly Tyr Thr Phe Thr Lys Tyr Trp
1               5

<210> SEQ ID NO 15
<211> LENGTH: 5
<212> TYPE: PRT
<213> ORGANISM: Artificial Sequence
<220> FEATURE:
<223> OTHER INFORMATION: humanized antibody VL3VHK20TFT HCDR3

<400> SEQUENCE: 15

Val Lys Asn Asp Asn
1               5

<210> SEQ ID NO 16
<211> LENGTH: 112
<212> TYPE: PRT
<213> ORGANISM: Artificial Sequence
<220> FEATURE:
<223> OTHER INFORMATION: humanized antibody VL3VHK20TFT VH

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Ile Asn Trp Val Arg Gln Ala Pro Gly Gln Gly Leu Glu Trp Met
            35                  40                  45

Gly Ile Ile Tyr Pro Gly Ser Ser Thr Ser Asn Tyr Asn Glu Lys Phe
        50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

<210> SEQ ID NO 17

```
<211> LENGTH: 111
<212> TYPE: PRT
<213> ORGANISM: Artificial Sequence
<220> FEATURE:
<223> OTHER INFORMATION: humanized antibody VL3VHK20TFT VL

<400> SEQUENCE: 17
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His Gln Ser Lys
                85                  90                  95

Glu Val Pro Tyr Thr Phe Gly Gln Gly Thr Lys Leu Glu Ile Lys
            100                 105                 110

```
<210> SEQ ID NO 18
<211> LENGTH: 438
<212> TYPE: PRT
<213> ORGANISM: Artificial Sequence
<220> FEATURE:
<223> OTHER INFORMATION: humanized antibody VL3VHK20TFT heavy chain

<400> SEQUENCE: 18
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro

```
                210                 215                 220
Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 19
<211> LENGTH: 218
<212> TYPE: PRT
<213> ORGANISM: Artificial Sequence
<220> FEATURE:
<223> OTHER INFORMATION: humanized antibody VL3VHK20TFT light chain

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His Gln Ser Lys
                85                  90                  95

Glu Val Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

```
                130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 20
<211> LENGTH: 1389
<212> TYPE: DNA
<213> ORGANISM: Artificial Sequence
<220> FEATURE:
<223> OTHER INFORMATION: humanized antibody VL3VHK20TFT heavy chain

<400> SEQUENCE: 20
atggacccca agggcagcct gagctggaga atcctgctgt tcctgagcct ggccttcgag     60
ctgagctacg ccaggtgca gctggtgcag agcggtgcgg aagtgaagaa gcccggtgcc    120
agcgtgaagg tgagctgcaa ggccagcggc tacaccttca ccaagtactg gatcaactgg    180
gtgaggcagg caccggcca aggcctggag tggatgggca tcatctaccc cggcagcagc    240
accagcaatt acaacgagaa gttcaagacc cgagtaacca tgaccgtgga cacctccacc    300
agcaccgcct acatggagct gagcagcctg aggagcgagg acaccgcagt gtactactgc    360
gtgaagaacg acaactgggg ccagggcacc ctggtgaccg tcagctctgc tagcaccaag    420
ggccccagcg tgtttcctct cgctccctgc agccggagca catccgagag caccgctgct    480
ctgggctgtc tcgtgaagga ctacttccct gaacccgtca ccgtcagctg gaatagcggc    540
gccctgacat ccggcgtcca cacattcccc gctgtcctgc agagcagcgg cctgtacagc    600
ctgagctccg tggtcaccgt gcctagcagc agcctgggaa caaagaccta cacctgcaac    660
gtggaccata agccctccaa caccaaggtg gacaagcggg tggaatccaa gtatggaccc    720
ccctgtcctc cttgccctgc tcctgaattt ctcggaggcc cctccgtctt cctgtttccc    780
cccaagccca aggacaccct gatgatctcc cggacacccg aagtcacctg cgtcgtggtg    840
gatgtcagcc aggaagatcc cgaggtgcag ttcaactggt acgtggacgg agtggaggtg    900
cataacgcca aaaccaagcc cagggaagag cagttcaaca gcacctatcg ggtcgtgtcc    960
gtgctcaccg tcctgcatca ggattggctc aacggcaagg agtacaagtg caaggtgtcc   1020
aacaagggcc tgccctcctc catcgagaag accatctcca aggctaaggg ccaacctcgg   1080
gagccccaag tgtataccct ccctcccagc caggaggaga tgaccaagaa tcaagtgagc   1140
ctgacctgcc tcgtgaaggg attttacccc tccgacatcg ctgtggaatg ggaaagcaat   1200
ggccaacctg agaacaacta caagaccaca ccccccgtgc tggactccga tggctccttc   1260
ttcctgtaca gcaggctgac cgtggacaaa tccggtggc aagagggaaa cgtgttcagc   1320
tgctccgtga tgcacgaggc tctccacaac cactacaccc agaagagcct ctccctgagc   1380
ctcggctag                                                            1389

<210> SEQ ID NO 21
<211> LENGTH: 717
<212> TYPE: DNA
```

-continued

<213> ORGANISM: Artificial Sequence
<220> FEATURE:
<223> OTHER INFORMATION: humanized antibody VL3VHK20TFT light chain

<400> SEQUENCE: 21

```
atggagaccg acaccctgct gctctgggtg ctgctgctct gggtgcccgg ctccaccgga      60
gacatccaga tgacccagag ccccagcagc ctgtccgcta gcgtaggcga cagggtcacc     120
atcacctgta gggccagtga gagcgtggac aactacggca tcagcttat gaactggttc      180
cagcagaagc ccggcaaggc ccccaagctg ctgatttacg ccgccagcga cctgggcagc     240
ggcgtgccca gtaggttcag cggctccggt agcggcaccg acttcaccct gactatcagc     300
tctctgcagc ccgaggactt cgccacctac tactgccacc agagcaagga ggtccctat     360
accttcggcc aaggcaccaa gttggagatc aagcggaccg tggccgcccc cagcgtgttc     420
atcttccctc ccagcgacga gcagctgaag tctggcaccg ccagcgtggt gtgcctgctg     480
aacaacttct accccgcga ggccaaggtg cagtggaagg tggacaacgc cctgcagagc     540
ggcaacagcc aggagagcgt gaccgagcag gactccaagg acagcaccta cagcctgagc     600
agcaccctga ccctgagcaa ggccgactac gagaagcaca aggtgtacgc ctgcgaggtg     660
acccaccagg gactgtctag ccccgtgacc aagagcttca ccggggcga gtgctaa         717
```

<210> SEQ ID NO 22
<211> LENGTH: 24
<212> TYPE: PRT
<213> ORGANISM: Unknown
<220> FEATURE:
<223> OTHER INFORMATION: leader sequence

<400> SEQUENCE: 22

Met Asp Pro Lys Gly Ser Leu Ser Trp Arg Ile Leu Leu Phe Leu Ser
1               5                   10                  15

Leu Ala Phe Glu Leu Ser Tyr Gly
            20

<210> SEQ ID NO 23
<211> LENGTH: 20
<212> TYPE: PRT
<213> ORGANISM: Unknown
<220> FEATURE:
<223> OTHER INFORMATION: leader sequence

<400> SEQUENCE: 23

Met Glu Thr Asp Thr Leu Leu Leu Trp Val Leu Leu Leu Trp Val Pro
1               5                   10                  15

Gly Ser Thr Gly
            20

<210> SEQ ID NO 24
<211> LENGTH: 1181
<212> TYPE: PRT
<213> ORGANISM: Homo sapiens

<400> SEQUENCE: 24

Met Ala Gly Ala Arg Ser Arg Asp Pro Trp Gly Ala Ser Gly Ile Cys
1               5                   10                  15

Tyr Leu Phe Gly Ser Leu Leu Val Glu Leu Leu Phe Ser Arg Ala Val
            20                  25                  30

Ala Phe Asn Leu Asp Val Met Gly Ala Leu Arg Lys Glu Gly Glu Pro
        35                  40                  45

-continued

```
Gly Ser Leu Phe Gly Phe Ser Val Ala Leu His Arg Gln Leu Gln Pro
    50                  55                  60

Arg Pro Gln Ser Trp Leu Leu Val Gly Ala Pro Gln Ala Leu Ala Leu
65                  70                  75                  80

Pro Gly Gln Gln Ala Asn Arg Thr Gly Gly Leu Phe Ala Cys Pro Leu
                85                  90                  95

Ser Leu Glu Glu Thr Asp Cys Tyr Arg Val Asp Ile Asp Gln Gly Ala
            100                 105                 110

Asp Met Gln Lys Glu Ser Lys Glu Asn Gln Trp Leu Gly Val Ser Val
        115                 120                 125

Arg Ser Gln Gly Pro Gly Gly Lys Ile Val Thr Cys Ala His Arg Tyr
    130                 135                 140

Glu Ala Arg Gln Arg Val Asp Gln Ile Leu Glu Thr Arg Asp Met Ile
145                 150                 155                 160

Gly Arg Cys Phe Val Leu Ser Gln Asp Leu Ala Ile Arg Asp Glu Leu
                165                 170                 175

Asp Gly Gly Glu Trp Lys Phe Cys Glu Gly Arg Pro Gln Gly His Glu
            180                 185                 190

Gln Phe Gly Phe Cys Gln Gln Gly Thr Ala Ala Ala Phe Ser Pro Asp
        195                 200                 205

Ser His Tyr Leu Leu Phe Gly Ala Pro Gly Thr Tyr Asn Trp Lys Gly
    210                 215                 220

Thr Ala Arg Val Glu Leu Cys Ala Gln Gly Ser Ala Asp Leu Ala His
225                 230                 235                 240

Leu Asp Asp Gly Pro Tyr Glu Ala Gly Gly Glu Lys Glu Gln Asp Pro
                245                 250                 255

Arg Leu Ile Pro Val Pro Ala Asn Ser Tyr Phe Gly Leu Leu Phe Val
            260                 265                 270

Thr Asn Ile Asp Ser Ser Asp Pro Asp Gln Leu Val Tyr Lys Thr Leu
        275                 280                 285

Asp Pro Ala Asp Arg Leu Pro Gly Pro Ala Gly Asp Leu Ala Leu Asn
    290                 295                 300

Ser Tyr Leu Gly Phe Ser Ile Asp Ser Gly Lys Gly Leu Val Arg Ala
305                 310                 315                 320

Glu Glu Leu Ser Phe Val Ala Gly Ala Pro Arg Ala Asn His Lys Gly
                325                 330                 335

Ala Val Val Ile Leu Arg Lys Asp Ser Ala Ser Arg Leu Val Pro Glu
            340                 345                 350

Val Met Leu Ser Gly Glu Arg Leu Thr Ser Gly Phe Gly Tyr Ser Leu
        355                 360                 365

Ala Val Ala Asp Leu Asn Ser Asp Gly Trp Pro Asp Leu Ile Val Gly
    370                 375                 380

Ala Pro Tyr Phe Phe Glu Arg Gln Glu Glu Leu Gly Gly Ala Val Tyr
385                 390                 395                 400

Val Tyr Leu Asn Gln Gly Gly His Trp Ala Gly Ile Ser Pro Leu Arg
                405                 410                 415

Leu Cys Gly Ser Pro Asp Ser Met Phe Gly Ile Ser Leu Ala Val Leu
            420                 425                 430

Gly Asp Leu Asn Gln Asp Gly Phe Pro Asp Ile Ala Val Gly Ala Pro
        435                 440                 445

Phe Asp Gly Asp Gly Lys Val Phe Ile Tyr His Gly Ser Ser Leu Gly
    450                 455                 460

Val Val Ala Lys Pro Ser Gln Val Leu Glu Gly Glu Ala Val Gly Ile
```

```
              465                 470                 475                 480
        Lys Ser Phe Gly Tyr Ser Leu Ser Gly Ser Leu Asp Met Asp Gly Asn
                            485                 490                 495

Gln Tyr Pro Asp Leu Leu Val Gly Ser Leu Ala Asp Thr Ala Val Leu
                            500                 505                 510

Phe Arg Ala Arg Pro Ile Leu His Val Ser His Glu Val Ser Ile Ala
                            515                 520                 525

Pro Arg Ser Ile Asp Leu Glu Gln Pro Asn Cys Ala Gly Gly His Ser
                            530                 535                 540

Val Cys Val Asp Leu Arg Val Cys Phe Ser Tyr Ile Ala Val Pro Ser
        545                 550                 555                 560

Ser Tyr Ser Pro Thr Val Ala Leu Asp Tyr Val Leu Asp Ala Asp Thr
                            565                 570                 575

Asp Arg Arg Leu Arg Gly Gln Val Pro Arg Val Thr Phe Leu Ser Arg
                            580                 585                 590

Asn Leu Glu Glu Pro Lys His Gln Ala Ser Gly Thr Val Trp Leu Lys
                            595                 600                 605

His Gln His Asp Arg Val Cys Gly Asp Ala Met Phe Gln Leu Gln Glu
                            610                 615                 620

Asn Val Lys Asp Lys Leu Arg Ala Ile Val Val Thr Leu Ser Tyr Ser
        625                 630                 635                 640

Leu Gln Thr Pro Arg Leu Arg Arg Gln Ala Pro Gly Gln Gly Leu Pro
                            645                 650                 655

Pro Val Ala Pro Ile Leu Asn Ala His Gln Pro Ser Thr Gln Arg Ala
                            660                 665                 670

Glu Ile His Phe Leu Lys Gln Gly Cys Gly Glu Asp Lys Ile Cys Gln
                            675                 680                 685

Ser Asn Leu Gln Leu Val Arg Ala Arg Phe Cys Thr Arg Val Ser Asp
                            690                 695                 700

Thr Glu Phe Gln Pro Leu Pro Met Asp Val Asp Gly Thr Thr Ala Leu
        705                 710                 715                 720

Phe Ala Leu Ser Gly Gln Pro Val Ile Gly Leu Glu Leu Met Val Thr
                            725                 730                 735

Asn Leu Pro Ser Asp Pro Ala Gln Pro Gln Ala Asp Gly Asp Asp Ala
                            740                 745                 750

His Glu Ala Gln Leu Leu Val Met Leu Pro Asp Ser Leu His Tyr Ser
                            755                 760                 765

Gly Val Arg Ala Leu Asp Pro Ala Glu Lys Pro Leu Cys Leu Ser Asn
                            770                 775                 780

Glu Asn Ala Ser His Val Glu Cys Glu Leu Gly Asn Pro Met Lys Arg
        785                 790                 795                 800

Gly Ala Gln Val Thr Phe Tyr Leu Ile Leu Ser Thr Ser Gly Ile Ser
                            805                 810                 815

Ile Glu Thr Thr Glu Leu Glu Val Glu Leu Leu Leu Ala Thr Ile Ser
                            820                 825                 830

Glu Gln Glu Leu His Pro Val Ser Ala Arg Ala Arg Val Phe Ile Glu
                            835                 840                 845

Leu Pro Leu Ser Ile Ala Gly Met Ala Ile Pro Gln Gln Leu Phe Phe
                            850                 855                 860

Ser Gly Val Val Arg Gly Glu Arg Ala Met Gln Ser Glu Arg Asp Val
        865                 870                 875                 880

Gly Ser Lys Val Lys Tyr Glu Val Thr Val Ser Asn Gln Gly Gln Ser
                            885                 890                 895
```

```
Leu Arg Thr Leu Gly Ser Ala Phe Leu Asn Ile Met Trp Pro His Glu
            900                 905                 910
Ile Ala Asn Gly Lys Trp Leu Leu Tyr Pro Met Gln Val Glu Leu Glu
            915                 920                 925
Gly Gly Gln Gly Pro Gln Lys Gly Leu Cys Ser Pro Arg Pro Asn
930                 935                 940
Ile Leu His Leu Asp Val Asp Ser Arg Asp Arg Arg Arg Glu Leu
945                 950                 955                 960
Glu Pro Pro Glu Gln Gln Pro Gly Glu Arg Gln Glu Pro Ser Met
                965                 970                 975
Ser Trp Trp Pro Val Ser Ser Ala Glu Lys Lys Lys Asn Ile Thr Leu
            980                 985                 990
Asp Cys Ala Arg Gly Thr Ala Asn Cys Val Val Phe Ser Cys Pro Leu
            995                 1000                1005
Tyr Ser Phe Asp Arg Ala Ala Val Leu His Val Trp Gly Arg Leu
    1010                1015                1020
Trp Asn Ser Thr Phe Leu Glu Glu Tyr Ser Ala Val Lys Ser Leu
    1025                1030                1035
Glu Val Ile Val Arg Ala Asn Ile Thr Val Lys Ser Ser Ile Lys
    1040                1045                1050
Asn Leu Met Leu Arg Asp Ala Ser Thr Val Ile Pro Val Met Val
    1055                1060                1065
Tyr Leu Asp Pro Met Ala Val Val Ala Glu Gly Val Pro Trp Trp
    1070                1075                1080
Val Ile Leu Leu Ala Val Leu Ala Gly Leu Leu Val Leu Ala Leu
    1085                1090                1095
Leu Val Leu Leu Leu Trp Lys Met Gly Phe Phe Lys Arg Ala Lys
    1100                1105                1110
His Pro Glu Ala Thr Val Pro Gln Tyr His Ala Val Lys Ile Pro
    1115                1120                1125
Arg Glu Asp Arg Gln Gln Phe Lys Glu Lys Thr Gly Thr Ile
    1130                1135                1140
Leu Arg Asn Asn Trp Gly Ser Pro Arg Arg Glu Gly Pro Asp Ala
    1145                1150                1155
His Pro Ile Leu Ala Ala Asp Gly His Pro Glu Leu Gly Pro Asp
    1160                1165                1170
Gly His Pro Gly Pro Gly Thr Ala
    1175                1180

<210> SEQ ID NO 25
<211> LENGTH: 4
<212> TYPE: PRT
<213> ORGANISM: Homo sapiens

<400> SEQUENCE: 25

Ser Trp Trp Pro
1

<210> SEQ ID NO 26
<211> LENGTH: 5
<212> TYPE: PRT
<213> ORGANISM: Artificial Sequence
<220> FEATURE:
<223> OTHER INFORMATION: VK CDR1

<400> SEQUENCE: 26
```

```
Tyr Gly Ile Ser Phe
1               5

<210> SEQ ID NO 27
<211> LENGTH: 10
<212> TYPE: PRT
<213> ORGANISM: Artificial Sequence
<220> FEATURE:
<223> OTHER INFORMATION: VH CDR1

<400> SEQUENCE: 27

Gly Tyr Thr Phe Thr Ser Tyr Tyr Met His
1               5                   10

<210> SEQ ID NO 28
<211> LENGTH: 5
<212> TYPE: PRT
<213> ORGANISM: Artificial Sequence
<220> FEATURE:
<223> OTHER INFORMATION: VK CDR1

<400> SEQUENCE: 28

Gln Gly Thr Ser Tyr
1               5

<210> SEQ ID NO 29
<211> LENGTH: 5
<212> TYPE: PRT
<213> ORGANISM: Artificial Sequence
<220> FEATURE:
<223> OTHER INFORMATION: VK CDR1

<400> SEQUENCE: 29

Ser Gly Thr Ser Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: VK CDR1

<400> SEQUENCE: 30

Arg Ala Ser Gln Ser Ile Ser Ser Tyr Leu Asn
1               5                   10

<210> SEQ ID NO 31
<211> LENGTH: 438
<212> TYPE: PRT
<213> ORGANISM: Artificial Sequence
<220> FEATURE:
<223> OTHER INFORMATION: Heavy chain VHK33

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Val Arg Gly Asp Glu Trp Gly Gln Gly Thr Leu Val Thr Val Ser Ser
                100                 105                 110

Ala Ser Thr Lys Gly Pro Ser Val Phe Pro Leu Ala Pro Cys Ser Arg
                115                 120                 125

Ser Thr Ser Glu Ser Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
                180                 185                 190

Tyr Thr Cys Asn Val Asp His Lys Pro Ser Asn Thr Lys Val Asp Lys
                195                 200                 205

Arg Val Glu Ser Lys Tyr Gly Pro Pro Cys Pro Pro Cys Pro Ala Pro
            210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
                260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
                340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly
            435

<210> SEQ ID NO 32
<211> LENGTH: 438
<212> TYPE: PRT
<213> ORGANISM: Artificial Sequence
<220> FEATURE:
<223> OTHER INFORMATION: Heavy chain VHK20

<400> SEQUENCE: 32

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Asn Phe Thr Lys Tyr
            20                  25                  30

Trp Ile Asn Trp Val Arg Gln Ala Pro Gly Gln Gly Leu Glu Trp Met
            35                  40                  45

Gly Ile Ile Tyr Pro Gly Ser Ser Thr Ser Asn Tyr Asn Glu Lys Phe
50                      55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
                180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415
```

Cys Ser Val Met His Glu Ala Leu His Asn His Tyr Thr Gln Lys Ser
            420                 425                 430
Leu Ser Leu Ser Leu Gly
        435

<210> SEQ ID NO 33
<211> LENGTH: 438
<212> TYPE: PRT
<213> ORGANISM: Artificial Sequence
<220> FEATURE:
<223> OTHER INFORMATION: Heavy chain VHK22

<400> SEQUENCE: 33

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Asn Phe Thr Lys Tyr
            20                  25                  30
Trp Ile Asn Trp Val Arg Gln Ala Pro Gly Gln Gly Leu Glu Trp Met
        35                  40                  45
Gly Ile Ile Tyr Pro Gly Ser Ser Ser Asn Tyr Asn Glu Lys Phe
    50                  55                  60
Lys Thr Arg Val Thr Met Thr Val Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Val Lys Asn Asp Val Trp Gly Gln Gly Thr Leu Val Thr Val Ser Ser
            100                 105                 110
Ala Ser Thr Lys Gly Pro Ser Val Phe Pro Leu Ala Pro Cys Ser Arg
        115                 120                 125
Ser Thr Ser Glu Ser Thr Ala Ala Leu Gly Cys Leu Val Lys Asp Tyr
    130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Lys Thr
            180                 185                 190
Tyr Thr Cys Asn Val Asp His Lys Pro Ser Asn Thr Lys Val Asp Lys
        195                 200                 205
Arg Val Glu Ser Lys Tyr Gly Pro Pro Cys Pro Pro Cys Pro Ala Pro
    210                 215                 220
Glu Phe Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser Gln Glu Asp Pro Glu Val Gln Phe Asn Trp Tyr Val Asp
            260                 265                 270
Gly Val Glu Val His Asn Ala Lys Thr Lys Pro Arg Glu Glu Gln Phe
        275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Gly Leu
305                 310                 315                 320
Pro Ser Ser Ile Glu Lys Thr Ile Ser Lys Ala Lys Gly Gln Pro Arg
                325                 330                 335

```
Glu Pro Gln Val Tyr Thr Leu Pro Pro Ser Gln Glu Glu Met Thr Lys
                340                 345                 350

Asn Gln Val Ser Leu Thr Cys Leu Val Lys Gly Phe Tyr Pro Ser Asp
                355                 360                 365

Ile Ala Val Glu Trp Glu Ser Asn Gly Gln Pro Glu Asn Asn Tyr Lys
                370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly
                435

<210> SEQ ID NO 34
<211> LENGTH: 438
<212> TYPE: PRT
<213> ORGANISM: Artificial Sequence
<220> FEATURE:
<223> OTHER INFORMATION: Heavy chain VHK48

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
                20                  25                  30

Trp Ile Asn Trp Val Arg Gln Ala Pro Gly Gln Gly Leu Glu Trp Met
                35                  40                  45

Gly Ile Ile Tyr Pro Gly Ser Ser Thr Ser Asn Tyr Asn Glu Lys Phe
        50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Asp Asn Trp Gly Gln Gly Thr Leu Val Thr Val Ser Ser
                100                 105                 110

Ala Ser Thr Lys Gly Pro Ser Val Phe Pro Leu Ala Pro Cys Ser Arg
                115                 120                 125

Ser Thr Ser Glu Ser Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
                180                 185                 190

Tyr Thr Cys Asn Val Asp His Lys Pro Ser Asn Thr Lys Val Asp Lys
                195                 200                 205

Arg Val Glu Ser Lys Tyr Gly Pro Pro Cys Pro Pro Cys Pro Ala Pro
                210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255
```

-continued

Asp Val Ser Gln Glu Asp Pro Glu Val Gln Phe Asn Trp Tyr Val Asp
                260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
        290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 35
<211> LENGTH: 438
<212> TYPE: PRT
<213> ORGANISM: Artificial Sequence
<220> FEATURE:
<223> OTHER INFORMATION: Heavy chain VHK14

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
                20                  25                  30

Trp Ile Asn Trp Val Arg Gln Ala Pro Gly Gln Gly Leu Glu Trp Met
            35                  40                  45

Gly Ile Ile Tyr Pro Gly Ser Ser Thr Ser Asn Tyr Asn Glu Lys Phe
        50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Gly Asp Val Trp Gly Gln Gly Thr Leu Val Thr Val Ser Ser
                100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

-continued

Leu Ser Ser Val Val Thr Val Pro Ser Ser Leu Gly Thr Lys Thr
            180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
        435

<210> SEQ ID NO 36
<211> LENGTH: 438
<212> TYPE: PRT
<213> ORGANISM: Artificial Sequence
<220> FEATURE:
<223> OTHER INFORMATION: Heavy chain VHK7

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Val Lys Gly Asp Lys Trp Gly Gln Gly Thr Leu Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
        435

<210> SEQ ID NO 37
<211> LENGTH: 438
<212> TYPE: PRT
<213> ORGANISM: Artificial Sequence
<220> FEATURE:
<223> OTHER INFORMATION: Heavy chain VHK51

<400> SEQUENCE: 37

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Asn Phe Thr Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Asp Thr Trp Gly Gln Gly Thr Leu Val Thr Val Ser Ser
                100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
                180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
```

<210> SEQ ID NO 38
<211> LENGTH: 438
<212> TYPE: PRT
<213> ORGANISM: Artificial Sequence
<220> FEATURE:
<223> OTHER INFORMATION: Heavy chain VHK11

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Gly Asp Gln Trp Gly Gln Gly Thr Leu Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
```

```
            355                 360                 365
Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                    405                 410                 415

Cys Ser Val Met His Glu Ala Leu His Asn His Tyr Thr Gln Lys Ser
                420                 425                 430

Leu Ser Leu Ser Leu Gly
            435

<210> SEQ ID NO 39
<211> LENGTH: 438
<212> TYPE: PRT
<213> ORGANISM: Artificial Sequence
<220> FEATURE:
<223> OTHER INFORMATION: Heavy chain VHK2

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
                20                  25                  30

Trp Ile Asn Trp Val Arg Gln Ala Pro Gly Gln Gly Leu Glu Trp Met
            35                  40                  45

Gly Ile Ile Tyr Pro Gly Ser Ser Thr Ser Asn Tyr Asn Glu Lys Phe
        50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Gly Asp Ala Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
```

```
                275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Gly Leu
305                 310                 315                 320
Pro Ser Ser Ile Glu Lys Thr Ile Ser Lys Ala Lys Gly Gln Pro Arg
                325                 330                 335
Glu Pro Gln Val Tyr Thr Leu Pro Pro Ser Gln Glu Glu Met Thr Lys
                340                 345                 350
Asn Gln Val Ser Leu Thr Cys Leu Val Lys Gly Phe Tyr Pro Ser Asp
                355                 360                 365
Ile Ala Val Glu Trp Glu Ser Asn Gly Gln Pro Glu Asn Asn Tyr Lys
                370                 375                 380
Thr Thr Pro Pro Val Leu Asp Ser Asp Gly Ser Phe Phe Leu Tyr Ser
385                 390                 395                 400
Arg Leu Thr Val Asp Lys Ser Arg Trp Gln Glu Gly Asn Val Phe Ser
                405                 410                 415
Cys Ser Val Met His Glu Ala Leu His Asn His Tyr Thr Gln Lys Ser
                420                 425                 430
Leu Ser Leu Ser Leu Gly
            435

<210> SEQ ID NO 40
<211> LENGTH: 438
<212> TYPE: PRT
<213> ORGANISM: Artificial Sequence
<220> FEATURE:
<223> OTHER INFORMATION: Heavy chain VHK4

<400> SEQUENCE: 40

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Asn Phe Thr Lys Tyr
                20                  25                  30
Trp Ile Asn Trp Val Arg Gln Ala Pro Gly Gln Gly Leu Glu Trp Met
            35                  40                  45
Gly Ile Ile Tyr Pro Gly Ser Ser Thr Ser Asn Tyr Asn Glu Lys Phe
        50                  55                  60
Lys Thr Arg Val Thr Met Thr Val Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Val Lys Gly Asp Glu Trp Gly Gln Gly Thr Leu Val Thr Val Ser Ser
                100                 105                 110
Ala Ser Thr Lys Gly Pro Ser Val Phe Pro Leu Ala Pro Cys Ser Arg
            115                 120                 125
Ser Thr Ser Glu Ser Thr Ala Ala Leu Gly Cys Leu Val Lys Asp Tyr
        130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Lys Thr
                180                 185                 190
Tyr Thr Cys Asn Val Asp His Lys Pro Ser Asn Thr Lys Val Asp Lys
```

```
            195                 200                 205
Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
                260                 265                 270

Gly Val Glu Val His Asn Ala Lys Thr Lys Pro Arg Glu Glu Gln Phe
                275                 280                 285

Asn Ser Thr Tyr Arg Val Val Ser Val Leu Thr Val Leu His Gln Asp
                290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
                340                 345                 350

Asn Gln Val Ser Leu Thr Cys Leu Val Lys Gly Phe Tyr Pro Ser Asp
                355                 360                 365

Ile Ala Val Glu Trp Glu Ser Asn Gly Gln Pro Glu Asn Asn Tyr Lys
                370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly
                435

<210> SEQ ID NO 41
<211> LENGTH: 438
<212> TYPE: PRT
<213> ORGANISM: Artificial Sequence
<220> FEATURE:
<223> OTHER INFORMATION: Heavy chain VHK12

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
                20                  25                  30

Trp Ile Asn Trp Val Arg Gln Ala Pro Gly Gln Gly Leu Glu Trp Met
            35                  40                  45

Gly Ile Ile Tyr Pro Gly Ser Thr Ser Asn Tyr Asn Glu Lys Phe
        50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Gly Asp Ser Trp Gly Gln Gly Thr Leu Val Thr Val Ser Ser
                100                 105                 110

Ala Ser Thr Lys Gly Pro Ser Val Phe Pro Leu Ala Pro Cys Ser Arg
```

```
                115                 120                 125
Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
        435

<210> SEQ ID NO 42
<211> LENGTH: 438
<212> TYPE: PRT
<213> ORGANISM: Artificial Sequence
<220> FEATURE:
<223> OTHER INFORMATION: Heavy chain VH

<400> SEQUENCE: 42

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Asn Phe Thr Lys Tyr
            20                  25                  30

Trp Ile Asn Trp Val Lys Gln Arg Pro Gly Gln Gly Leu Glu Trp Ile
```

```
              35                  40                  45
Gly Ile Ile Tyr Pro Gly Ser Ser Thr Ser Asn Tyr Asn Glu Lys Phe
 50                  55                  60

Lys Thr Lys Ala Thr Leu Thr Val Glu Ile Ser Ser Thr Thr Ala Tyr
 65                  70                  75                  80

Met Gln Leu Ser Ser Leu Thr Ser Asp Asp Ser Ala Val Tyr Tyr Cys
                 85                  90                  95

Val Arg Gly Asp Asp Trp Gly Gln Gly Thr Thr Leu Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
        290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 43
```

<211> LENGTH: 438
<212> TYPE: PRT
<213> ORGANISM: Artificial Sequence
<220> FEATURE:
<223> OTHER INFORMATION: Heavy chain VH3

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Gly Asp Asp Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

```
Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
            405                 410                 415

Cys Ser Val Met His Glu Ala Leu His Asn His Tyr Thr Gln Lys Ser
        420                 425                 430

Leu Ser Leu Ser Leu Gly
            435

<210> SEQ ID NO 44
<211> LENGTH: 438
<212> TYPE: PRT
<213> ORGANISM: Artificial Sequence
<220> FEATURE:
<223> OTHER INFORMATION: Heavy chain VHK20NFA

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Lys Tyr
            20                  25                  30

Trp Ile Asn Trp Val Arg Gln Ala Pro Gly Gln Gly Leu Glu Trp Met
        35                  40                  45

Gly Ile Ile Tyr Pro Gly Ser Ser Thr Ser Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300
```

```
Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
                340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435
```

<210> SEQ ID NO 45
<211> LENGTH: 438
<212> TYPE: PRT
<213> ORGANISM: Artificial Sequence
<220> FEATURE:
<223> OTHER INFORMATION: Heavy chain VHK20TFT-A

<400> SEQUENCE: 45

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

His Ile Asn Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220
```

```
Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 46
<211> LENGTH: 438
<212> TYPE: PRT
<213> ORGANISM: Artificial Sequence
<220> FEATURE:
<223> OTHER INFORMATION: Heavy chain VHK20TFT-B

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
                20                  25                  30

Asn Ile Asn Trp Val Arg Gln Ala Pro Gly Gln Gly Leu Glu Trp Met
            35                  40                  45

Gly Ile Ile Tyr Pro Gly Ser Ser Ser Asn Tyr Asn Glu Lys Phe
        50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140
```

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Lys Thr
        180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
        210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser Gln Glu Asp Pro Glu Val Gln Phe Asn Trp Tyr Val Asp
        260                 265                 270

Gly Val Glu Val His Asn Ala Lys Thr Lys Pro Arg Glu Glu Gln Phe
    275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
        340                 345                 350

Asn Gln Val Ser Leu Thr Cys Leu Val Lys Gly Phe Tyr Pro Ser Asp
    355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
            405                 410                 415

Cys Ser Val Met His Glu Ala Leu His Asn His Tyr Thr Gln Lys Ser
        420                 425                 430

Leu Ser Leu Ser Leu Gly
        435

<210> SEQ ID NO 47
<211> LENGTH: 438
<212> TYPE: PRT
<213> ORGANISM: Artificial Sequence
<220> FEATURE:
<223> OTHER INFORMATION: Heavy chain VHK20TFT-C

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Trp Ile Asn Trp Val Arg Gln Ala Pro Gly Gln Gly Leu Glu Trp Met
        35                  40                  45

Gly Thr Ile Gln Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
        435

<210> SEQ ID NO 48
<211> LENGTH: 438
<212> TYPE: PRT
<213> ORGANISM: Artificial Sequence
<220> FEATURE:

<223> OTHER INFORMATION: Heavy chain VHK20TFT-D

<400> SEQUENCE: 48

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Val | Ser | Cys | Lys | Ala | Ser | Gly | Tyr | Thr | Phe | Thr | Lys | Tyr |
| | | | 20 | | | | | 25 | | | | | 30 | | |
| Trp | Ile | Asn | Trp | Val | Arg | Gln | Ala | Pro | Gly | Gln | Gly | Leu | Glu | Trp | Met |
| | | | 35 | | | | | 40 | | | | | 45 | | |
| Gly | Thr | Ile | His | Pro | Gly | Ser | Ser | Ser | Asn | Tyr | Asn | Glu | Lys | Phe |
| | 50 | | | | | 55 | | | | | 60 | | | | |
| Lys | Thr | Arg | Val | Thr | Met | Thr | Val | Asp | Thr | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Val | Lys | Asn | Asp | Asn | Trp | Gly | Gln | Gly | Thr | Leu | Val | Thr | Val | Ser | Ser |
| | | | 100 | | | | | 105 | | | | | 110 | | |
| Ala | Ser | Thr | Lys | Gly | Pro | Ser | Val | Phe | Pro | Leu | Ala | Pro | Cys | Ser | Arg |
| | | | 115 | | | | | 120 | | | | | 125 | | |
| Ser | Thr | Ser | Glu | Ser | Thr | Ala | Ala | Leu | Gly | Cys | Leu | Val | Lys | Asp | Tyr |
| | | | 130 | | | | | 135 | | | | | 140 | | |
| Phe | Pro | Glu | Pro | Val | Thr | Val | Ser | Trp | Asn | Ser | Gly | Ala | Leu | Thr | Ser |
| 145 | | | | | 150 | | | | | 155 | | | | | 160 |
| Gly | Val | His | Thr | Phe | Pro | Ala | Val | Leu | Gln | Ser | Ser | Gly | Leu | Tyr | Ser |
| | | | | 165 | | | | | 170 | | | | | 175 | |
| Leu | Ser | Ser | Val | Val | Thr | Val | Pro | Ser | Ser | Ser | Leu | Gly | Thr | Lys | Thr |
| | | | | 180 | | | | | 185 | | | | | 190 | |
| Tyr | Thr | Cys | Asn | Val | Asp | His | Lys | Pro | Ser | Asn | Thr | Lys | Val | Asp | Lys |
| | | | | 195 | | | | | 200 | | | | | 205 | |
| Arg | Val | Glu | Ser | Lys | Tyr | Gly | Pro | Pro | Cys | Pro | Pro | Cys | Pro | Ala | Pro |
| | | | 210 | | | | | 215 | | | | | 220 | | |
| Glu | Phe | Leu | Gly | Gly | Pro | Ser | Val | Phe | Leu | Phe | Pro | Pro | Lys | Pro | Lys |
| 225 | | | | | 230 | | | | | 235 | | | | | 240 |
| Asp | Thr | Leu | Met | Ile | Ser | Arg | Thr | Pro | Glu | Val | Thr | Cys | Val | Val | Val |
| | | | | 245 | | | | | 250 | | | | | 255 | |
| Asp | Val | Ser | Gln | Glu | Asp | Pro | Glu | Val | Gln | Phe | Asn | Trp | Tyr | Val | Asp |
| | | | | 260 | | | | | 265 | | | | | 270 | |
| Gly | Val | Glu | Val | His | Asn | Ala | Lys | Thr | Lys | Pro | Arg | Glu | Glu | Gln | Phe |
| | | | 275 | | | | | 280 | | | | | 285 | | |
| Asn | Ser | Thr | Tyr | Arg | Val | Val | Ser | Val | Leu | Thr | Val | Leu | His | Gln | Asp |
| | | | 290 | | | | | 295 | | | | | 300 | | |
| Trp | Leu | Asn | Gly | Lys | Glu | Tyr | Lys | Cys | Lys | Val | Ser | Asn | Lys | Gly | Leu |
| 305 | | | | | 310 | | | | | 315 | | | | | 320 |
| Pro | Ser | Ser | Ile | Glu | Lys | Thr | Ile | Ser | Lys | Ala | Lys | Gly | Gln | Pro | Arg |
| | | | | 325 | | | | | 330 | | | | | 335 | |
| Glu | Pro | Gln | Val | Tyr | Thr | Leu | Pro | Pro | Ser | Gln | Glu | Glu | Met | Thr | Lys |
| | | | 340 | | | | | 345 | | | | | 350 | | |
| Asn | Gln | Val | Ser | Leu | Thr | Cys | Leu | Val | Lys | Gly | Phe | Tyr | Pro | Ser | Asp |
| | | | 355 | | | | | 360 | | | | | 365 | | |
| Ile | Ala | Val | Glu | Trp | Glu | Ser | Asn | Gly | Gln | Pro | Glu | Asn | Asn | Tyr | Lys |
| | | 370 | | | | | 375 | | | | | 380 | | | |
| Thr | Thr | Pro | Pro | Val | Leu | Asp | Ser | Asp | Gly | Ser | Phe | Phe | Leu | Tyr | Ser |
| 385 | | | | | 390 | | | | | 395 | | | | | 400 |

```
Arg Leu Thr Val Asp Lys Ser Arg Trp Gln Glu Gly Asn Val Phe Ser
                405                 410                 415
Cys Ser Val Met His Glu Ala Leu His Asn His Tyr Thr Gln Lys Ser
            420                 425                 430
Leu Ser Leu Ser Leu Gly
            435
```

<210> SEQ ID NO 49
<211> LENGTH: 438
<212> TYPE: PRT
<213> ORGANISM: Artificial Sequence
<220> FEATURE:
<223> OTHER INFORMATION: Heavy chain VHK20TFT-E

<400> SEQUENCE: 49

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Lys Tyr
            20                  25                  30
Trp Ile Asn Trp Val Arg Gln Ala Pro Gly Gln Gly Leu Glu Trp Met
        35                  40                  45
Gly Thr Ile Asn Pro Gly Ser Ser Thr Ser Asn Tyr Asn Glu Lys Phe
    50                  55                  60
Lys Thr Arg Val Thr Met Thr Val Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Val Lys Asn Asp Asn Trp Gly Gln Gly Thr Leu Val Thr Val Ser Ser
            100                 105                 110
Ala Ser Thr Lys Gly Pro Ser Val Phe Pro Leu Ala Pro Cys Ser Arg
        115                 120                 125
Ser Thr Ser Glu Ser Thr Ala Ala Leu Gly Cys Leu Val Lys Asp Tyr
    130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Lys Thr
            180                 185                 190
Tyr Thr Cys Asn Val Asp His Lys Pro Ser Asn Thr Lys Val Asp Lys
        195                 200                 205
Arg Val Glu Ser Lys Tyr Gly Pro Pro Cys Pro Pro Cys Pro Ala Pro
    210                 215                 220
Glu Phe Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser Gln Glu Asp Pro Glu Val Gln Phe Asn Trp Tyr Val Asp
            260                 265                 270
Gly Val Glu Val His Asn Ala Lys Thr Lys Pro Arg Glu Glu Gln Phe
        275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Gly Leu
305                 310                 315                 320
```

```
Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
        340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 50
<211> LENGTH: 438
<212> TYPE: PRT
<213> ORGANISM: Artificial Sequence
<220> FEATURE:
<223> OTHER INFORMATION: Heavy chain VHK20TFT-F

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Tyr Pro Gly Ser Ser Thr Ser Asn Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240
```

```
Asp Thr Leu Met Ile Ser Arg Thr Pro Glu Val Thr Cys Val Val Val
            245                 250                 255

Asp Val Ser Gln Glu Asp Pro Glu Val Gln Phe Asn Trp Tyr Val Asp
        260                 265                 270

Gly Val Glu Val His Asn Ala Lys Thr Lys Pro Arg Glu Glu Gln Phe
    275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 51
<211> LENGTH: 218
<212> TYPE: PRT
<213> ORGANISM: Artificial Sequence
<220> FEATURE:
<223> OTHER INFORMATION: Light chain VL1

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Tyr Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His Gln Ser Lys
                85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 218
<212> TYPE: PRT
<213> ORGANISM: Artificial Sequence
<220> FEATURE:
<223> OTHER INFORMATION: Light chain VL2

<400> SEQUENCE: 52

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Tyr Gln Gln Lys Pro Gly Lys Ala Pro
        35                  40                  45

Lys Leu Leu Ile Tyr Ala Ala Ser Asp Leu Gly Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys His Gln Ser Lys
                85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 53
<211> LENGTH: 218
<212> TYPE: PRT
<213> ORGANISM: Artificial Sequence
<220> FEATURE:
<223> OTHER INFORMATION: Light chain VL3

<400> SEQUENCE: 53

Asp Ile Gln Met Thr Gln Ser Pro Ser Leu Ser Ala Ser Val Gly
1               5                   10                  15

Asp Arg Val Thr Ile Thr Cys Arg Ala Ser Glu Ser Val Asp Asn Tyr
            20                  25                  30
```

```
Gly Ile Ser Phe Met Asn Trp Phe Gln Gln Lys Pro Gly Lys Ala Pro
            35                  40                  45

Lys Leu Leu Ile Tyr Ala Ala Ser Asp Leu Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys His Gln Ser Lys
                 85                  90                  95

Glu Val Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 54
<211> LENGTH: 218
<212> TYPE: PRT
<213> ORGANISM: Artificial Sequence
<220> FEATURE:
<223> OTHER INFORMATION: Light chain VL4

<400> SEQUENCE: 54

Asp Ile Gln Leu Thr Gln Ser Pro Ser Ser Leu Ser Val Ser Val Gly
 1               5                  10                  15

Asp Arg Ala Thr Ile Thr Cys Arg Ala Ser Glu Ser Val Asp Asn Tyr
                20                  25                  30

Gly Ile Ser Phe Met Asn Trp Phe Gln Gln Lys Pro Gly Lys Ala Pro
            35                  40                  45

Lys Leu Leu Ile Tyr Ala Ala Ser Asp Leu Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Met Gln Pro Glu Asp Phe Ala Thr Tyr Tyr Cys His Gln Ser Lys
                 85                  90                  95

Glu Val Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 55
<211> LENGTH: 218
<212> TYPE: PRT
<213> ORGANISM: Artificial Sequence
<220> FEATURE:
<223> OTHER INFORMATION: Light chain VL5

<400> SEQUENCE: 55

```
Asp Ile Gln Leu Thr Gln Ser Pro Ser Ser Leu Ser Val Ser Val Gly
1               5                   10                  15

Asp Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Met Gln Pro Glu Asp Ser Ala Thr Tyr Tyr Cys His Gln Ser Lys
                85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 56
<211> LENGTH: 218
<212> TYPE: PRT
<213> ORGANISM: Artificial Sequence
<220> FEATURE:
<223> OTHER INFORMATION: Light chain VL

<400> SEQUENCE: 56

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
```

```
            35                  40                  45
Lys Leu Leu Ile Tyr Ala Ala Ser Asp Leu Gly Ser Gly Val Pro Ala
 50                  55                  60

Arg Phe Thr Gly Ser Gly Ser Gly Thr Asp Phe Ser Leu Asn Ile His
 65                  70                  75                  80

Pro Met Glu Glu Asp Ser Ala Met Tyr Phe Cys His Gln Ser Lys
                 85                  90                  95

Glu Val Pro Tyr Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 57
<211> LENGTH: 218
<212> TYPE: PRT
<213> ORGANISM: Artificial Sequence
<220> FEATURE:
<223> OTHER INFORMATION: Light chain VL6

<400> SEQUENCE: 57

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Ser Val Asp Asn Tyr
                 20                  25                  30

Gly Ile Ser Phe Met Asn Trp Tyr Gln Gln Lys Pro Gly Lys Ala Pro
             35                  40                  45

Lys Leu Leu Ile Tyr Ala Ala Ser Asp Leu Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys His Gln Ser Lys
                 85                  90                  95

Glu Val Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

```
                180             185             190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 58
<211> LENGTH: 218
<212> TYPE: PRT
<213> ORGANISM: Artificial Sequence
<220> FEATURE:
<223> OTHER INFORMATION: Light chain VL7

<400> SEQUENCE: 58

Asp Ile Gln Leu Thr Gln Ser Pro Ser Ser Leu Ser Ala Ser Val Gly
1               5                   10                  15
Asp Arg Val Thr Ile Thr Cys Arg Ala Ser Glu Ser Val Asp Asn Tyr
            20                  25                  30
Gly Ile Ser Phe Met Asn Trp Tyr Gln Gln Lys Pro Gly Lys Ala Pro
        35                  40                  45
Lys Leu Leu Ile Tyr Ala Ala Ser Asp Leu Gly Ser Gly Val Pro Ser
50                  55                  60
Arg Phe Thr Gly Ser Gly Ser Gly Thr Asp Phe Ser Leu Thr Ile Ser
65                  70                  75                  80
Ser Leu Gln Pro Glu Asp Phe Ala Thr Tyr Phe Cys His Gln Ser Lys
                85                  90                  95
Glu Val Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 59
<211> LENGTH: 218
<212> TYPE: PRT
<213> ORGANISM: Artificial Sequence
<220> FEATURE:
<223> OTHER INFORMATION: Light chain VL8

<400> SEQUENCE: 59

Asp Ile Gln Leu Thr Gln Ser Pro Ser Ser Leu Ser Val Ser Val Gly
1               5                   10                  15
Asp Arg Ala Thr Ile Thr Cys Arg Ala Ser Glu Ser Val Asp Asn Tyr
            20                  25                  30
Gly Ile Ser Phe Met Asn Trp Tyr Gln Gln Lys Pro Gly Lys Ala Pro
        35                  40                  45
```

```
Lys Leu Leu Ile Tyr Ala Ala Ser Asp Leu Gly Ser Gly Val Pro Ser
 50                  55                  60

Arg Phe Thr Gly Ser Gly Ser Gly Thr Asp Phe Ser Leu Thr Ile Ser
 65                  70                  75                  80

Ser Met Gln Pro Glu Asp Phe Ala Thr Tyr Phe Cys His Gln Ser Lys
                 85                  90                  95

Glu Val Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 60
<211> LENGTH: 218
<212> TYPE: PRT
<213> ORGANISM: Artificial Sequence
<220> FEATURE:
<223> OTHER INFORMATION: Light chain VL9

<400> SEQUENCE: 60

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Asn Tyr
             20                  25                  30

Gly Ile Ser Phe Met Asn Trp Phe Gln Gln Lys Pro Gly Lys Ala Pro
         35                  40                  45

Lys Leu Leu Ile Tyr Ala Ala Ser Asp Leu Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys His Gln Ser Lys
                 85                  90                  95

Glu Val Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 61
<211> LENGTH: 218
<212> TYPE: PRT
<213> ORGANISM: Artificial Sequence
<220> FEATURE:
<223> OTHER INFORMATION: Light chain VL10

<400> SEQUENCE: 61

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys His Gln Ser Lys
                85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 62
<211> LENGTH: 218
<212> TYPE: PRT
<213> ORGANISM: Artificial Sequence
<220> FEATURE:
<223> OTHER INFORMATION: Light chain VL11

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Gln
            20                  25                  30

Gly Thr Ser Tyr Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His Gln Ser Lys
            85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 63
<211> LENGTH: 218
<212> TYPE: PRT
<213> ORGANISM: Artificial Sequence
<220> FEATURE:
<223> OTHER INFORMATION: Light chain VL12

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Ser
            20                  25                  30

Gly Thr Ser Tyr Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His Gln Ser Lys
            85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

```
Val Thr Lys Ser Phe Asn Arg Gly Glu Cys
    210                 215

<210> SEQ ID NO 64
<211> LENGTH: 218
<212> TYPE: PRT
<213> ORGANISM: Artificial Sequence
<220> FEATURE:
<223> OTHER INFORMATION: Light chain VL13

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Ser Phe Met Asn Trp Phe Gln Gln Lys Pro Gly Lys Ala Pro
        35                  40                  45

Lys Leu Leu Ile Tyr Ala Ala Ser Asp Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His Gln Ser Lys
                85                  90                  95

Glu Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 65
<211> LENGTH: 8
<212> TYPE: PRT
<213> ORGANISM: Artificial Sequence
<220> FEATURE:
<223> OTHER INFORMATION: antibody HCDR1

<400> SEQUENCE: 65

Gly Tyr Thr Phe Thr Lys Tyr His
1               5

<210> SEQ ID NO 66
<211> LENGTH: 5
<212> TYPE: PRT
<213> ORGANISM: Artificial Sequence
<220> FEATURE:
<223> OTHER INFORMATION: antibody HCDR3

<400> SEQUENCE: 66
```

Val Lys Asn Asp Asn
1               5

<210> SEQ ID NO 67
<211> LENGTH: 112
<212> TYPE: PRT
<213> ORGANISM: Artificial Sequence
<220> FEATURE:
<223> OTHER INFORMATION: antibody VH

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
                20                  25                  30

His Ile Asn Trp Val Arg Gln Ala Pro Gly Gln Gly Leu Glu Trp Met
            35                  40                  45

Gly Ile Ile Tyr Pro Gly Ser Ser Thr Ser Asn Tyr Asn Glu Lys Phe
        50                  55                  60

Lys Thr Arg Val Thr Met Thr Val Asp Thr Ser Ser Thr Thr Ala Tyr
65                  70                  75                  80

Met Glu Leu Ser Ser Leu Arg Ser Glu Asp Thr Ala Val Tyr Tyr Cys
                85                  90                  95

Val Lys Asn Asp Asn Trp Gly Gln Gly Thr Leu Val Thr Val Ser Ser
                100                 105                 110

<210> SEQ ID NO 68
<211> LENGTH: 5
<212> TYPE: PRT
<213> ORGANISM: Artificial Sequence
<220> FEATURE:
<223> OTHER INFORMATION: antibody HCDR3

<400> SEQUENCE: 68

Val Lys Asn Asp Asn
1               5

<210> SEQ ID NO 69
<211> LENGTH: 10
<212> TYPE: PRT
<213> ORGANISM: Artificial Sequence
<220> FEATURE:
<223> OTHER INFORMATION: antibody LCDR1

<400> SEQUENCE: 69

Glu Ser Val Asp Asn Gln Gly Thr Ser Tyr
1               5                   10

<210> SEQ ID NO 70
<211> LENGTH: 111
<212> TYPE: PRT
<213> ORGANISM: Artificial Sequence
<220> FEATURE:
<223> OTHER INFORMATION: antibody VL

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Gln
                20                  25                  30

Gly Thr Ser Tyr Met Asn Trp Phe Gln Gln Lys Pro Gly Lys Ala Pro
            35                  40                  45

```
Lys Leu Leu Ile Tyr Ala Ala Ser Asp Leu Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys His Gln Ser Lys
             85                  90                  95

Glu Val Pro Tyr Thr Phe Gly Gln Gly Thr Lys Leu Glu Ile Lys
            100                 105                 110

<210> SEQ ID NO 71
<211> LENGTH: 10
<212> TYPE: PRT
<213> ORGANISM: Artificial Sequence
<220> FEATURE:
<223> OTHER INFORMATION: antibody LCDR1

<400> SEQUENCE: 71

Glu Ser Val Asp Asn Ser Gly Thr Ser Tyr
1               5                   10

<210> SEQ ID NO 72
<211> LENGTH: 111
<212> TYPE: PRT
<213> ORGANISM: Artificial Sequence
<220> FEATURE:
<223> OTHER INFORMATION: antibody VL

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Ser
             20                  25                  30

Gly Thr Ser Tyr Met Asn Trp Phe Gln Gln Lys Pro Gly Lys Ala Pro
         35                  40                  45

Lys Leu Leu Ile Tyr Ala Ala Ser Asp Leu Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys His Gln Ser Lys
             85                  90                  95

Glu Val Pro Tyr Thr Phe Gly Gln Gly Thr Lys Leu Glu Ile Lys
            100                 105                 110

<210> SEQ ID NO 73
<211> LENGTH: 139
<212> TYPE: PRT
<213> ORGANISM: Homo sapiens

<400> SEQUENCE: 73

Asp Asn Val Cys Lys Pro Lys Leu Glu Val Ser Val Asp Ser Asp Gln
1               5                   10                  15

Lys Lys Ile Tyr Ile Gly Asp Asp Asn Pro Leu Thr Leu Ile Val Lys
             20                  25                  30

Ala Gln Asn Gln Gly Glu Gly Ala Tyr Glu Ala Glu Leu Ile Val Ser
         35                  40                  45

Ile Pro Leu Gln Ala Asp Phe Ile Gly Val Val Arg Asn Asn Glu Ala
 50                  55                  60

Leu Ala Arg Leu Ser Cys Ala Phe Lys Thr Glu Asn Gln Thr Arg Gln
 65                  70                  75                  80
```

-continued

Val Val Cys Asp Leu Gly Asn Pro Met Lys Ala Gly Thr Gln Leu Leu
                85                  90                  95

Ala Gly Leu Arg Phe Ser Val His Gln Gln Ser Glu Met Asp Thr Ser
            100                 105                 110

Val Lys Phe Asp Leu Gln Ile Gln Ser Ser Asn Leu Phe Asp Lys Val
        115                 120                 125

Ser Pro Val Val Ser His Lys Val Asp Leu Ala
    130                 135

<210> SEQ ID NO 74
<211> LENGTH: 219
<212> TYPE: PRT
<213> ORGANISM: Homo sapiens

<400> SEQUENCE: 74

Val Leu Ala Ala Val Glu Ile Arg Gly Val Ser Ser Pro Asp His Val
1               5                   10                  15

Phe Leu Pro Ile Pro Asn Trp Glu His Lys Glu Asn Pro Glu Thr Glu
            20                  25                  30

Glu Asp Val Gly Pro Val Val Gln His Ile Tyr Glu Leu Arg Asn Asn
        35                  40                  45

Gly Pro Ser Ser Phe Ser Lys Ala Met Leu His Leu Gln Trp Pro Tyr
    50                  55                  60

Lys Tyr Asn Asn Asn Thr Leu Leu Tyr Ile Leu His Tyr Asp Ile Asp
65                  70                  75                  80

Gly Pro Met Asn Cys Thr Ser Asp Met Glu Ile Asn Pro Leu Arg Ile
                85                  90                  95

Lys Ile Ser Ser Leu Gln Thr Thr Glu Lys Asn Asp Thr Val Ala Gly
            100                 105                 110

Gln Gly Glu Arg Asp His Leu Ile Thr Lys Arg Asp Leu Ala Leu Ser
        115                 120                 125

Glu Gly Asp Ile His Thr Leu Gly Cys Gly Val Ala Gln Cys Leu Lys
    130                 135                 140

Ile Val Cys Gln Val Gly Arg Leu Asp Arg Gly Lys Ser Ala Ile Leu
145                 150                 155                 160

Tyr Val Lys Ser Leu Leu Trp Thr Glu Thr Phe Met Asn Lys Glu Asn
                165                 170                 175

Gln Asn His Ser Tyr Ser Leu Lys Ser Ser Ala Ser Phe Asn Val Ile
            180                 185                 190

Glu Phe Pro Tyr Lys Asn Leu Pro Ile Glu Asp Ile Thr Asn Ser Thr
        195                 200                 205

Leu Val Thr Thr Asn Val Thr Trp Gly Ile Gln
    210                 215

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Gly Tyr Asn Phe Ala Lys Tyr Trp
1               5

<210> SEQ ID NO 76
<211> LENGTH: 8
<212> TYPE: PRT

```
<213> ORGANISM: Artificial Sequence
<220> FEATURE:
<223> OTHER INFORMATION: Synthetic Construct

<400> SEQUENCE: 76

Gly Tyr Thr Phe Thr Lys Tyr Asn
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Construct

<400> SEQUENCE: 77

Val Arg Gly Asp Glu
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Construct

<400> SEQUENCE: 78

Val Lys Asn Asp Val
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Construct

<400> SEQUENCE: 79

Val Arg Arg Asp Asn
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct

<400> SEQUENCE: 80

Val Lys Gly Asp Val
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Construct

<400> SEQUENCE: 81

Val Lys Gly Asp Lys
1               5

<210> SEQ ID NO 82
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 82

Val Arg Arg Asp Thr
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic Construct

<400> SEQUENCE: 83

Val Lys Gly Asp Gln
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic Construct

<400> SEQUENCE: 84

Val Lys Gly Asp Ala
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic Construct

<400> SEQUENCE: 85

Val Lys Gly Asp Glu
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Construct

<400> SEQUENCE: 86

Val Arg Gly Asp Glu
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Construct

<400> SEQUENCE: 87

Val Lys Gly Asp Ser
1               5
```

ANTIBODIES BINDING TO α7β1 INTEGRIN ANTIBODIES AND COMPOSITIONS THEREOF

CROSS-REFERENCE TO RELATED APPLICATIONS

This application claims the benefit of U.S. Provisional Patent Application No. 63/029,070, filed on May 22, 2020, U.S. Provisional Patent Application No. 63/009,020, filed on Apr. 13, 2020, and U.S. Provisional Patent Application No. 62/935,732, filed on Nov. 15, 2019, the disclosure of each of which is hereby incorporated by reference in its entirety.

DESCRIPTION OF THE TEXT FILE SUBMITTED ELECTRONICALLY

The Sequence Listing associated with this application is provided in text format in lieu of a paper copy, and is hereby incorporated by reference into the specification. The name of the text file containing the Sequence Listing is 768092005600SUBSEQLIST.TXT. The text file is 152,334 bytes, was created on Jul. 26, 2023, and is being submitted electronically via EFS-Web.

FIELD OF THE INVENTION

The invention relates generally to compositions and methods for activating integrin heterodimers that contain beta-1 integrin protein that specifically binds laminin protein. Such compositions and methods are useful for treating diseases related to muscle malfunction, including muscular dystrophies.

BACKGROUND OF THE INVENTION

Skeletal muscle cells are surrounded by a basement membrane bridging the muscle membrane (sarcolemma) to the interstitial extracellular matrix. The basement membrane plays key roles during development and in adults, supporting development, muscle integrity, synaptogenesis and muscle repair.

Mutations affecting functionality or synthesis of proteins involved in the extracellular matrix-basement membrane-skeletal muscle cells interactions are associated with muscular dystrophies. There are no current cures for any form of muscular dystrophy. Several types have been reported that can be categorized according to the function of the gene that is affected. These can be separated into several classes, with the most important one stemming from mutations in the plasma membrane cytoskeleton complex of the myofibers (the laminin dystroglycan/sarcoglycan/dystrophin complex). This complex acts as a laminin receptor anchoring the extracellular matrix to cytoskeletal proteins of the skeletal muscle cells.

The most common form of muscular dystrophy representing approximately half of the cases is that induced by mutations in the dystrophin gene (PNAS 1984; 81:1189). The presence of a truncated, partially functional form of dystrophin leads to symptoms associated with Becker muscular dystrophy (an X-linked recessive disorder). A more severe form is observed in Duchenne muscular dystrophy (DMD) patients (representing half of all muscular dystrophy cases), who have a mutation that leads to absence of, or a non-functional form of, the dystrophin protein. The incidence of DMD is about 1 in 3500 newborn males. Mutations in dystrophin are also believed to exhaust the muscle stem cell (satellite cells) pool which is activated in response to muscle injury. Mutations in the sarcoglycan gene (sarcoglycanopathies) lead to malfunction of a protein complex facilitating the interaction between the extracellular matrix and muscle via laminin α2 (merosin)-dystroglycan-dystrophin. Such mutations also lead to autosomal recessive muscular dystrophy that closely mimics the Duchenne dystrophy (NEJM 1997; 336:618). Mutations in laminin α2-chain (merosin), although rare, lead to the most severe form of myopathy as the muscle cells lose their extracellular matrix anchor (Nat Genetics 1995; 11:216).

Another protein, the integrin α7β1, also bridges laminin and cytoskeletal protein and actively contributes to muscle biology as its deficiency is also associated with a form of muscular dystrophy (Nat Genetics 1998; 19:94; Nat Genetics 1997; 17:318). Two other beta-1 containing heterodimers (α3β1, α6β1) bind to laminin, but there have been no reports of muscular dystrophy associated with mutations in these genes. α7β1 is the primary laminin receptor that is expressed in skeletal, cardiac and vascular smooth muscle cells, and its deficiency leads to delayed development and impaired mobility. The integrin α7β1 is believed to play a compensatory role in muscular dystrophies associated with mutations in dystrophin associated proteins. Indeed, its expression is upregulated in human and animal models of muscular dystrophies (J Cell Sci 1997; 110:2873). Integrin α7β1 deficiency combined with dystrophin, utrophin or sarcoglycan deficiencies leads to even more severe forms of the disease (Hum Mol Gen 2006; 15:989, J Cell Sci 2006; 119:2185, J Cell Biol 2001; 152:1207) and further causes myocardial dysfunction, fibrosis and calcification (Circ Res 2008; 102:1109).

There remains a need for a pharmaceutical agent that can provide a therapeutic benefit to subjects with deficiency in or malfunctions of the laminin/dystroglycan/sarcoglycan/dystrophin complex.

SUMMARY OF THE INVENTION

The invention provides a pharmaceutical agent that is an agonist of at least one of α7β1 integrin, α6β1 integrin and α3β1 integrin and that binds to the extracellular domain of at least one of α7 protein, α6 protein and α3 protein. In some embodiments, the pharmaceutical agent of claim 1, wherein the pharmaceutical agent binds at least one of: the laminin binding domain of at least one of α7 protein, α6 protein and α3 protein; the CALF-1 domain of at least one of α7 protein, α6 protein and α3 protein; and the CALF-2 domain of at least one of α7 protein, α6 protein and α3 protein. In some embodiments, a pharmaceutical agent is an agonist of α7β1 integrin and binds specifically to the α7 protein. In some embodiments, a pharmaceutical agent does not increase the amount of α7 protein in a muscle cell of a subject when the pharmaceutical agent is administered to the subject.

In some embodiments, a pharmaceutical agent that is an agonist of at least one of α7β1 integrin, α6β1 integrin and α3β1 integrin is an antibody. In some embodiments, an antibody is a monoclonal antibody. In certain embodiments, an antibody is a multispecific antibody (e.g., a bispecific antibody). In some embodiments, an antibody of the invention is human, humanized or chimeric.

In some embodiments, the invention encompasses a pharmaceutical agent that activates at least one of α7β1 integrin, α6β1 integrin and α3β1 integrin. In some embodiments, a pharmaceutical agent stabilizes the active conformation of at least one of α7β1 integrin, α6β1 integrin and α3β1 integrin.

In certain embodiments, a pharmaceutical agent does not bind specifically to the β1 protein. In some embodiments, a pharmaceutical agent increases the adhesion of a myoblast to merosin. For example, the myoblast may be a healthy human myoblast or a healthy murine myoblast. Alternatively, the myoblast may be a human myoblast or a murine myoblast that is dystrophin deficient, comprises a mutation in dystrophin or comprises non-functioning dystrophin. In some embodiments, a pharmaceutical agent increases the adhesion of a myotube to merosin. For example, the myotube may be a healthy human myotube or a healthy murine myotube. Alternatively, the myotube may be a human myotube or a murine myotube that is dystrophin deficient, comprises a mutation in dystrophin or comprises non-functioning dystrophin.

The invention further provides a monoclonal antibody that is an agonist of α7β1 integrin (e.g., human α7β1 integrin), or an antibody fragment thereof, wherein the antibody or the antibody fragment binds specifically to an epitope of α7 protein, wherein the epitope comprises, consists essentially of, or consists of: (i) the amino acid sequence of SEQ ID NO: 10 or SEQ ID NO: 1; (ii) 5-10, 10-15, 15-20, 20-25, 25-30, 30-35 or 35-40 amino acids of SEQ ID NO: 10 or SEQ ID NO: 1; or (iii) 5-10, 10-15, 15-20, 20-25, 25-30, 30-35 or 35-40 amino acids of SEQ ID NO: 24.

The invention also provides a monoclonal antibody that is an agonist of α7β1 integrin, or an antibody fragment thereof, wherein the antibody or the antibody fragment binds specifically to an epitope of α7 protein, wherein the epitope comprises SWWP (SEQ ID NO: 25). Further provided herein is a monoclonal antibody that is an agonist of α7β1 integrin, or an antibody fragment thereof, wherein the antibody or the antibody fragment binds specifically to an epitope comprising the residues S977, W978, W979 and P980 of SEQ ID NO: 24. In some embodiments, the epitope comprises, consists essentially of, or consists of 5-10 or 10-15 amino acids of SEQ ID NO: 24. The invention further provides a monoclonal antibody that is an agonist of α7β1 integrin, or an antibody fragment thereof, wherein the antibody or the antibody fragment binds specifically to an epitope comprising the residues R958, M976, S977, W978, W979 and P980 of SEQ ID NO: 24. In some embodiments, the epitope comprises, consists essentially of, or consists of 6-10 or 10-15 amino acids of SEQ ID NO: 24. In some embodiments, the epitope is continuous. In some embodiments, the epitope is discontinuous.

The invention further provides a monoclonal antibody that is an agonist of α7β1 integrin, or an antibody fragment thereof, that binds specifically to an epitope disclosed herein and comprises a heavy chain variable (VH) region comprising an HCDR1, an HCDR2 and an HCDR3, and a light chain variable (VL) region comprising an LCDR1, an LCDR2 and an LCDR3, (i) wherein the HCDR3 comprises SEQ ID NO: 15; and/or wherein the LCDR3 comprises SEQ ID NO: 7; (ii) wherein the HCDR3 comprises SEQ ID NO: 66; and/or wherein the LCDR3 comprises SEQ ID NO: 7; or (iii) wherein the HCDR3 comprises SEQ ID NO: 68; and/or wherein the LCDR3 comprises SEQ ID NO: 7.

In some embodiments, a monoclonal antibody that is an agonist of α7β1 integrin, or an antibody fragment thereof, binds specifically to an epitope disclosed herein and comprises a VH region comprising an HCDR1, an HCDR2 and an HCDR3, and a VL region comprising an LCDR1, an LCDR2 and an LCDR3, wherein the HCDR2 comprises SEQ ID NO: 3; and/or wherein the LCDR2 comprises SEQ ID NO: 6.

In some embodiments, a monoclonal antibody that is an agonist of α7β1 integrin, or an antibody fragment thereof, binds specifically to an epitope disclosed herein and comprises a VH region comprising an HCDR1, an HCDR2 and an HCDR3, and a VL region comprising an LCDR1, an LCDR2 and an LCDR3, (i) wherein the HCDR1 comprises SEQ ID NO: 14; and/or wherein the LCDR1 comprises SEQ ID NO: 5; (ii) wherein the HCDR1 comprises SEQ ID NO: 65; and/or wherein the LCDR1 comprises SEQ ID NO: 5; (iii) wherein the HCDR1 comprises SEQ ID NO: 14; and/or wherein the LCDR1 comprises SEQ ID NO: 69; or (iv) wherein the HCDR1 comprises SEQ ID NO: 14; and/or wherein the LCDR1 comprises SEQ ID NO: 71.

The invention encompasses a monoclonal antibody that is an agonist of α7β1 integrin (e.g., human α7β1 integrin), or an antibody fragment thereof, wherein the antibody or the antibody fragment comprises a heavy chain variable (VH) region and a light chain variable (VL) region, wherein the VH region amino acid sequence comprises HCDR1 of SEQ ID NO: 2, HCDR2 of SEQ ID NO: 3 and HCDR3 of SEQ ID NO: 4, or a variant thereof having 5 or fewer conservative amino acid substitutions in HCDR1, HCDR2, and/or HCDR3; wherein the VH region amino acid sequence comprises HCDR1 of SEQ ID NO: 14, HCDR2 of SEQ ID NO: 3 and HCDR3 of SEQ ID NO: 15, or a variant thereof having 5 or fewer conservative amino acid substitutions in HCDR1, HCDR2, and/or HCDR3; wherein the VH region amino acid sequence comprises HCDR1 of SEQ ID NO: 65, HCDR2 of SEQ ID NO: 3 and HCDR3 of SEQ ID NO: 66, or a variant thereof having 5 or fewer conservative amino acid substitutions in HCDR1, HCDR2, and/or HCDR3; or wherein the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3.

The invention also encompasses a monoclonal antibody that is an agonist of α7β1 integrin, or an antibody fragment thereof, wherein the antibody or the antibody fragment comprises a light chain variable (VL) region and a heavy chain variable (VH) region, wherein the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; wherein the VL region amino acid sequence comprises LCDR1 of SEQ ID NO: 69, LCDR2 of SEQ ID NO: 6 and LCDR3 of SEQ ID NO: 7, or a variant thereof having 5 or fewer conservative amino acid substitutions in LCDR1, LCDR2, and/or LCDR3; or wherein the VL region amino acid sequence comprises LCDR1 of SEQ ID NO: 71, LCDR2 of SEQ ID NO: 6 and LCDR3 of SEQ ID NO: 7, or a variant thereof having 5 or fewer conservative amino acid substitutions in LCDR1, LCDR2, and/or LCDR3.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein: (i) the VH region amino acid sequence comprises HCDR1 of SEQ ID NO: 2, HCDR2 of SEQ ID NO: 3 and HCDR3 of SEQ ID NO: 4, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; (ii) the VH region amino acid sequence comprises HCDR1 of SEQ ID NO: 14, HCDR2 of SEQ ID NO: 3 and HCDR3 of SEQ ID NO: 15, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; (iii) the VH region amino acid sequence comprises HCDR1 of SEQ ID NO: 65, HCDR2 of SEQ ID NO: 3 and HCDR3 of SEQ ID NO: 66, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; (iv) the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3; and the VL region amino acid sequence comprises LCDR1 of SEQ ID NO: 69, LCDR2 of SEQ ID NO: 6 and LCDR3 of SEQ ID NO: 7, or a variant thereof having 5 or fewer conservative amino acid substitutions in LCDR1, LCDR2, and/or LCDR3; or (v) the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3; and the VL region amino acid sequence comprises LCDR1 of SEQ ID NO: 71, LCDR2 of SEQ ID NO: 6 and LCDR3 of SEQ ID NO: 7, or a variant thereof having 5 or fewer conservative amino acid substitutions in LCDR1, LCDR2, and/or LCDR3.

The invention also encompasses an antibody or an antibody fragment thereof, wherein the VH region amino acid sequence comprises (i) SEQ ID NO: 8, or an amino acid sequence that is at least 95%, 96%, 97%, 98% or 99% identical to the amino acid sequence of SEQ ID NO: 8; (ii) SEQ ID NO: 16, or an amino acid sequence that is at least 95%, 96%, 97%, 98% or 99% identical to the amino acid sequence of SEQ ID NO: 16; or (iii) SEQ ID NO: 67, or an amino acid sequence that is at least 95%, 96%, 97%, 98% or 99% identical to the amino acid sequence of SEQ ID NO: 67.

The invention encompasses an antibody or an antibody fragment thereof, wherein the VL region amino acid sequence comprises (i) SEQ ID NO: 9, or an amino acid sequence that is at least 95%, 96%, 97%, 98% or 99% identical to the amino acid sequence of SEQ ID NO: 9; (ii) SEQ ID NO: 17, or an amino acid sequence that is at least 95%, 96%, 97%, 98% or 99% identical to the amino acid sequence of SEQ ID NO: 17; (iii) SEQ ID NO: 70, or an amino acid sequence that is at least 95%, 96%, 97%, 98% or 99% identical to the amino acid sequence of SEQ ID NO: 70; or (iv) SEQ ID NO: 72, or an amino acid sequence that is at least 95%, 96%, 97%, 98% or 99% identical to the amino acid sequence of SEQ ID NO: 72.

The invention also encompasses an antibody or an antibody fragment thereof, wherein (i) the VH region amino acid sequence comprises SEQ ID NO: 8, or an amino acid sequence that is at least 95%, 96%, 97%, 98% or 99% identical to the amino acid sequence of SEQ ID NO: 8; and the VL region amino acid sequence comprises SEQ ID NO: 9, or an amino acid sequence that is at least 95%, 96%, 97%, 98% or 99% identical to the amino acid sequence of SEQ ID NO: 9; (ii) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 17, or an amino acid sequence that is at least 95%, 96%, 97%, 98% or 99% identical to the amino acid sequence of SEQ ID NO: 17; (iii) the VH region amino acid sequence comprises SEQ ID NO: 67, or an amino acid sequence that is at least 95%, 96%, 97%, 98% or 99% identical to the amino acid sequence of SEQ ID NO: 67; and the VL region amino acid sequence comprises SEQ ID NO: 17, or an amino acid sequence that is at least 95%, 96%, 97%, 98% or 99% identical to the amino acid sequence of SEQ ID NO: 17; (iv) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 70, or an amino acid sequence that is at least 95%, 96%, 97%, 98% or 99% identical to the amino acid sequence of SEQ ID NO: 70; or (v) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 72, or an amino acid sequence that is at least 95%, 96%, 97%, 98% or 99% identical to the amino acid sequence of SEQ ID NO: 72.

In some embodiments, provided herein is a monoclonal antibody that is an agonist of α7β1 integrin, or an antibody fragment thereof, wherein the antibody comprises a heavy chain and a light chain, (i) wherein the heavy chain amino acid sequence comprises SEQ ID NO: 18, and the light chain amino acid sequence comprises SEQ ID NO: 19; (ii) wherein the heavy chain amino acid sequence comprises SEQ ID NO: 45, and the light chain amino acid sequence comprises SEQ ID NO: 53; (iii) wherein the heavy chain amino acid sequence comprises SEQ ID NO: 18, and the light chain amino acid sequence comprises SEQ ID NO: 62; or (iv) wherein the heavy chain amino acid sequence comprises SEQ ID NO: 18, and the light chain amino acid sequence comprises SEQ ID NO: 63.

In some embodiments, an antibody or antibody fragment of the invention binds specifically to α7 protein. In some cases, the antibody or the antibody fragment binds specifically to an epitope of α7 protein comprising, consisting essentially of, or consisting of the (i) amino acid sequence of SEQ ID NO: 10; (ii) 5-10, 10-15, 15-20, 20-25, 25-30, 30-35 or 35-40 amino acids of SEQ ID NO: 10; or (iii) 5-10, 10-15, 15-20, 20-25, 25-30, 30-35 or 35-40 amino acids of SEQ ID NO: 24.

In some embodiments, an antibody fragment of the invention may be an Fab, an F(ab')$_2$, an Fab', an scFv, a single domain antibody, a diabody or a single chain camelid antibody The invention encompasses an isolated nucleic acid molecule encoding an antibody or an antibody fragment disclosed herein. The invention also provides an expression vector comprising the nucleic acid molecule disclosed herein. In some embodiments of expression vectors, the nucleic acid molecule is operatively linked to regulatory sequences suitable for expression of the nucleic acid segment in a host cell. Additionally, the invention provides a recombinant host cell comprising an expression vector disclosed herein. The invention encompasses a method for producing an antibody that is an agonist of α7β1 integrin, or an antibody fragment thereof, the method comprising: culturing a recombinant host cell comprising an expression vector disclosed herein under conditions whereby the nucleic acid molecule is expressed, thereby producing the antibody that is an agonist of α7β1 integrin, or an antibody fragment thereof.

In some embodiments, the invention provides a pharmaceutical composition comprising a pharmaceutical agent, an antibody that is an agonist of at least one of α7β1 integrin, α6β1 integrin and α3β1 integrin, or an antibody fragment thereof, and a pharmaceutically acceptable carrier, diluent or excipient. In some embodiments, a pharmaceutical composition of the invention further comprises an additional pharmaceutical agent that is an agonist of at least one of α7β1 integrin, α6β1 integrin and α3β1 integrin.

The invention encompasses a method of treating a disorder or a disease in a subject comprising administering to the subject a therapeutically effective amount of a pharmaceutical agent, an antibody that is an agonist of at least one of α7β1 integrin, α6β1 integrin and α3β1 integrin, or an antibody fragment thereof, thereby treating the disorder or the disease in the subject. The disorder or the disease can be characterized by one or more of: a malfunction of α7β1 integrin in the subject; a dystrophin deficiency in the subject; a mutation in dystrophin in the subject; non-functioning dystrophin in the subject; or a muscle dysfunction other than α7β1 malfunction, or dystrophin deficiency, mutation, or non-function.

In some embodiments, the muscle dysfunction is caused by or associated with one or more of: cancer, congestive heart failure, chronic obstructive pulmonary disease, chronic kidney disease, HIV infection/AIDS, anorexia nervosa, bulimia, malnutrition, exposure, nausea, type I diabetes, type II diabetes, metabolic syndrome, cachexia, anemia, heart failure, high blood pressure, rhabdomyolysis, sepsis, sarcopenia, physical inactivity, damage due to excess physical activity, hypothermia, hyperthermia, injury, denervation, amyotrophic lateral sclerosis, multiple sclerosis, spinal muscular atrophy, alcohol-associated myopathy, burn-associated myopathy, stroke, steroid therapy or the withdrawal of steroid therapy, dermatomyositis, Guillain-Barré syndrome, neuropathy, osteoarthritis, infection, polio, polymyositis, inflammation, rheumatoid arthritis, hypocholesterolemia, electrical injury, heat stroke, prolonged immobilization, lack of blood flow to a limb, or contact with venom. The methods of treatment of the invention may further comprise a step of identifying a subject having a muscle dysfunction.

In some embodiments, the disease is a muscle wasting disease. In some embodiments, a muscle wasting disease is a muscular dystrophy. In certain cases, the muscular dystrophy is Duchenne muscular dystrophy (DMD), Becker muscular dystrophy, merosin-deficient congenital muscular dystrophy type 1A or limb-girdle muscular dystrophy. The methods of treatment of the invention may further comprise a step of identifying a subject having a muscle wasting disease. In some embodiments, the administration of a therapeutically effective amount of a pharmaceutical agent, an antibody that is an agonist of at least one of α7β1 integrin, α6β1 integrin and α3β1 integrin, or an antibody fragment thereof, reverses, stabilizes or slows muscle wasting or muscle dysfunction in the subject. In certain cases, the administration improves muscle function in the subject. In some embodiments, the administration does not worsen muscle function in the subject. The methods of treatment of the invention may further comprise measuring muscle function in the subject after the administration step, wherein the rate of worsening of muscle function is reduced.

In some embodiments, administering to the subject the therapeutically effective amount of the pharmaceutical agent is effective to upregulate the activity and/or amount of α7β1 integrin in the subject effective to treat the malfunction of α7β1 integrin in the subject.

In some embodiments, administering to the subject the therapeutically effective amount of the pharmaceutical agent is effective to upregulate activity and/or amount of α7β1 integrin in the subject, the upregulated activity and/or amount of α7β1 integrin in the subject being effective to at least in part mitigate the effect of at least one of: the dystrophin deficiency in the subject; the mutation in dystrophin in the subject; or the non-functioning dystrophin in the subject.

In some embodiments, administering to the subject the therapeutically effective amount of the pharmaceutical agent is effective to mitigate muscle injury in the subject.

In some embodiments, administering to the subject the therapeutically effective amount of the pharmaceutical agent is effective to mitigate eccentric muscle injury in the subject.

In some embodiments, administering to the subject the therapeutically effective amount of the pharmaceutical agent is effective to improve diaphragm muscle function in the subject.

In some embodiments, a method of the invention further comprises administering to the subject one or more other therapies, the one or more other therapies directed to muscular dystrophy or muscle wasting. In some embodiments, the one or more other therapies comprises one or more of: an anticonvulsant; an immunosuppressant; an antibiotic; quinine; therapy for management of congestive heart failure; a gene replacement therapy; an exon skipping therapy; a nonsense suppression therapy; therapy using an engineered nuclease; cell therapy using muscle precursor cells or stem cells; upregulation of utrophin; an anti-inflammatory therapy; an antifibrotic therapy; a steroid therapy; a myostatin blocker; insulin growth factor; a phosphodiesterase-5 inhibitor; an ACE inhibitor; induction of angiogenesis through delivery of vascular endothelial growth factor (VEGF); downregulation of VEGF decoy-receptor type 1 (VEGFR-1 or Flt-1); physical therapy; occupational therapy; surgery; orthotic intervention; speech therapy; respiratory therapy; a pacemaker; and a respiratory assistance device.

The invention encompasses a method of activating α7β1 integrin in a muscle cell of a subject, the method comprising: administering to the subject a therapeutically effective amount of a pharmaceutical agent, an antibody that is an agonist of at least one of α7β1 integrin, α6β1 integrin and α3β1 integrin, or an antibody fragment thereof, thereby activating α7β1 integrin in a muscle cell of the subject. The invention also provides a method of enhancing binding of α7β1 integrin to its ligand in a muscle cell of a subject, the method comprising: administering to the subject a therapeutically effective amount of a pharmaceutical agent, an antibody that is an agonist of at least one of α7β1 integrin, α6β1 integrin and α3β1 integrin, or an antibody fragment thereof, thereby enhancing binding of α7β1 integrin to its ligand in a muscle cell of the subject.

The invention provides a use of the pharmaceutical agent of a pharmaceutical agent, an antibody that is an agonist of at least one of α7β1 integrin, α6β1 integrin and α3β1 integrin, or an antibody fragment thereof, in the manufacture of a medicament for treating a disorder or a disease characterized by a malfunction of α7β1 integrin in a subject.

DETAILED DESCRIPTION OF THE INVENTION

The invention provides pharmaceutical agents that activate integrin heterodimers containing the beta-1 (β1) protein that specifically bind laminin protein. An agonist of an integrin heterodimer containing the β1 protein may provide therapeutic benefits to a subject with muscular dystrophy associated with a malfunction of one of the proteins of the laminin/dystroglycan/sarcoglycan/dystrophin complex or the laminin-α2 (merosin) protein.

Integrin heterodimers are composed of non-covalently associated a and β protein subunits and act as transmembrane adhesion receptors (Hynes, (2002) Cell 110:673-687). In some embodiments, a pharmaceutical agent described herein is an agonist of at least one of α7β1 integrin, α6β1 integrin and α3β1 integrin. In certain cases, a pharmaceutical agent is an agonist of α7β1 integrin, α6β1 integrin and α3β1 integrin. In other embodiments, a pharmaceutical agent is an agonist of α7β1 integrin and α6β1 integrin. In other embodiments, a pharmaceutical agent is an agonist of α6β1 integrin and α3β1 integrin. In yet other embodiments, a pharmaceutical agent is an agonist of α7β1 integrin and α3β1 integrin. In one embodiment, a pharmaceutical agent is an agonist of α7β1 integrin. In another embodiment, a pharmaceutical agent is an agonist of α6β 1 integrin. In yet another embodiment, a pharmaceutical agent is an agonist of α3β1 integrin. In some examples, the integrin proteins are human integrin proteins. In some embodiments, a pharmaceutical agent does not bind specifically to the β1 protein.

Figure 31:
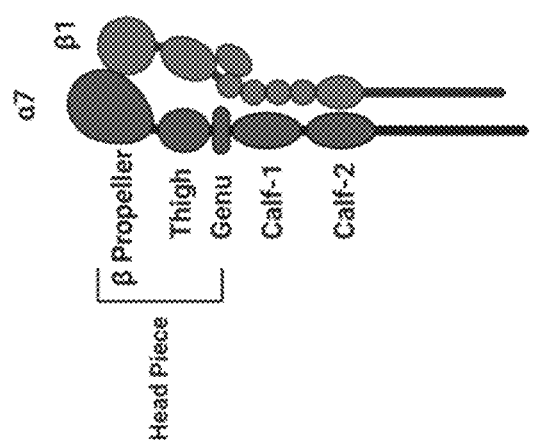
FIG. 31 is an illustration depicting the extracellular region of α7β1 integrin and various domains therein. The a chain of such integrins, e.g., α3, α6 and α7 (shown), include four extracellular domains: a seven-bladed β-propeller, a thigh, and two calf domains (CALF-1 and CALF-2). The thigh and calf domains have similar, immunoglobulin-like, β-sandwich folds.

The invention provides a pharmaceutical agent that is an agonist of at least one of α7β1 integrin, α6β1 integrin and α3β1 integrin and that binds to the extracellular domain of at least one of α7 protein, α6 protein and α3 protein. In some embodiments, a pharmaceutical agent binds at least one of: the laminin binding domain of at least one of α7 protein, α6 protein and α3 protein; the CALF-1 domain of at least one of α7 protein, α6 protein and α3 protein; and the CALF-2 domain of at least one of α7 protein, α6 protein and α3 protein. An illustration depicting the extracellular region of α7β1 integrin and various domains therein, including the CALF domains, is provided in FIG. 31.

In certain cases, a pharmaceutical agent binds to the laminin binding domains of one or more of α7 protein (SEQ ID NO: 11), α6 protein (SEQ ID NO: 12) and α3 protein (SEQ ID NO: 13). In some embodiments, a pharmaceutical agent binds to the laminin binding domains of α7 protein (SEQ ID NO: 11), α6 protein (SEQ ID NO: 12) and α3 protein (SEQ ID NO: 13).

In some embodiments, a pharmaceutical agent binds to the CALF-1 domain of at least one of α7 protein, α6 protein and α3 protein. An exemplary sequence of a human CALF-1 domain is provided in Table 1β. In some embodiments, a pharmaceutical agent binds to a CALF-1 domain comprising SEQ ID NO: 73.

In some embodiments, a pharmaceutical agent binds to the CALF-2 domain of at least one of α7 protein, α6 protein and α3 protein. An exemplary sequence of a human CALF-2 domain is provided in Table 1C. In some embodiments, a pharmaceutical agent binds to a CALF-2 domain comprising SEQ ID NO: 74.

The invention relates to a pharmaceutical agent that is an agonist of α7β1 integrin and that binds specifically to the α7 protein. In one embodiment, the invention provides a pharmaceutical agent that is an agonist of α7β1 integrin and that binds specifically to the α7 protein with the negative proviso that the pharmaceutical agent does not increase the amount of α7 protein in a muscle cell of a subject when the pharmaceutical agent is administered to the subject.

In some embodiments, the invention provides a pharmaceutical agent that confers an activated state on an α7β1 integrin heterodimer.

In some embodiments, a pharmaceutical agent described herein is an antibody.

Antibodies

In some embodiments, the invention provides a pharmaceutical agent that is an antibody. In one embodiment, an antibody binds specifically to the α7 protein. In another embodiment, an antibody binds specifically to the α6 protein. In a further embodiment, an antibody binds specifically to the α3 protein.

As used herein, the term "antibody" refers to immunoglobulin (Ig) molecules and immunologically active portions or fragments of immunoglobulin molecules, i.e., molecules that contain an antigen binding site that specifically binds (immunoreacts with) an antigen (e.g., α7 protein, α6 protein or α3 protein). By "specifically binds" or "immunoreacts with" is meant that the antibody reacts with one or more antigenic determinants of the desired antigen and does not react with other polypeptides. In certain embodiments, an antibody is said to specifically bind an antigen when it preferentially recognizes its target antigen in a complex mixture of proteins and/or macromolecules. The term "antibody" broadly refers to an immunoglobulin (Ig) molecule, generally comprising four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art.

In a full-length antibody, each heavy chain comprises a heavy chain variable region (abbreviated herein as HCVR or VH region) and a heavy chain constant region. The heavy chain constant region comprises three domains, CH1, CH2 and CH3. Each light chain comprises a light chain variable region (abbreviated herein as LCVR or VL region) and a light chain constant region. The light chain constant region comprises one domain, CL. The VH and VL regions can be further subdivided into regions of hypervariability, termed complementarity determining regions (CDRs), interspersed with regions that are more conserved, termed framework regions (FRs). Each VH region and VL region is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG3, IgG4, IgA1 and IgA2) or subclass. IgG, IgD, and IgE antibodies generally contain two identical heavy chains and two identical light chains and two antigen combining domains, each composed of a heavy chain variable region (VH) and a light chain variable region (VL). Generally IgA antibodies are composed of two monomers, each monomer composed of two heavy chains and two light chains (as for IgG, IgD, and IgE antibodies); in this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies); in this way the IgM molecule has ten antigen binding domains, each again composed of a VH and a VL. A cell surface form of IgM also exists and this has two heavy chain/two light chain structure similar to IgG, IgD, and IgE antibodies.

The term "antigen binding fragment" or "antigen binding portion" of an antibody (or simply "antibody fragment" or "antibody portion"), as used herein, refers to one or more fragments of an antibody that retain the ability to specifically bind to an antigen (e.g., α7 protein). It has been shown that the antigen binding function of an antibody can be performed by fragments of a full-length antibody. Antibody and antibody fragment embodiments may also be bispecific, trispecific, dual specific, or multi-specific formats; specifically binding to two or more different antigens. Examples of binding fragments encompassed within the term "antigen binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546, Winter et al., PCT publication WO 90/05144 A1, each herein incorporated by reference in its entirety), which comprises a single variable domain; and (vi) an isolated complementarity determining region (CDR). The invention also encompasses an Fab' fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding fragment" of an antibody. In certain embodiments of the invention, scFv molecules may be incorporated into a fusion protein. In some embodiments, the invention includes a single chain camelid antibody. Other forms of single chain antibodies, such as diabodies are also included. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding fragments are known in the art (Kontermann and Dubel eds., Antibody Engineering (2001) Springer-Verlag. New York. 790 pp.). In some aspects, the invention includes a single domain antibody. In general, the term "antibody" when used herein encompasses an "antibody fragment". An antibody fragment generally retains the antigen-binding properties of a full length antibody.

In certain embodiments, the invention provides antibodies and antibody fragments that are agonists of α7β1 integrin and that comprise one or more amino acid sequences shown in Table 2 or Table 3.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein the VH region amino acid sequence comprises HCDR1 of SEQ ID NO: 2, HCDR2 of SEQ ID NO: 3 and HCDR3 of SEQ ID NO: 4, or a variant thereof having 5 or fewer conservative amino acid substitutions in HCDR1, HCDR2, and/or HCDR3; wherein the VH region amino acid sequence comprises HCDR1 of SEQ ID NO: 14, HCDR2 of SEQ ID NO: 3 and HCDR3 of SEQ ID NO: 15, or a variant thereof having 5 or fewer conservative amino acid substitutions in HCDR1, HCDR2, and/or HCDR3; wherein the VH region amino acid sequence comprises HCDR1 of SEQ ID NO: 65, HCDR2 of SEQ ID NO: 3 and HCDR3 of SEQ ID NO: 66, or a variant thereof having 5 or fewer conservative amino acid substitutions in HCDR1, HCDR2, and/or HCDR3; or wherein the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3.

The invention also encompasses a monoclonal antibody that is an agonist of α7β1 integrin, or an antibody fragment thereof, wherein the antibody or the antibody fragment comprises a light chain variable (VL) region and a heavy chain variable (VH) region, wherein the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; wherein the VL region amino acid sequence comprises LCDR1 of SEQ ID NO: 69, LCDR2 of SEQ ID NO: 6 and LCDR3 of SEQ ID NO: 7, or a variant thereof having 5 or fewer conservative amino acid substitutions in LCDR1, LCDR2, and/or LCDR3; or wherein the VL region amino acid sequence comprises LCDR1 of SEQ ID NO: 71, LCDR2 of SEQ ID NO: 6 and LCDR3 of SEQ ID NO: 7, or a variant thereof having 5 or fewer conservative amino acid substitutions in LCDR1, LCDR2, and/or LCDR3.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 4, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; (ii) the VH region amino acid sequence comprises HCDR1 of SEQ ID NO: 14, HCDR2 of SEQ ID NO: 3 and HCDR3 of SEQ ID NO: 15, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; (iii) the VH region amino acid sequence comprises HCDR1 of SEQ ID NO: 65, HCDR2 of SEQ ID NO: 3 and HCDR3 of SEQ ID NO: 66, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3; (iv) the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3; and the VL region amino acid sequence comprises LCDR1 of SEQ ID NO: 69, LCDR2 of SEQ ID NO: 6 and LCDR3 of SEQ ID NO: 7, or a variant thereof having 5 or fewer conservative amino acid substitutions in LCDR1, LCDR2, and/or LCDR3; or (v) the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3; and the VL region amino acid sequence comprises LCDR1 of SEQ ID NO: 71, LCDR2 of SEQ ID NO: 6 and LCDR3 of SEQ ID NO: 7, or a variant thereof having 5 or fewer conservative amino acid substitutions in LCDR1, LCDR2, and/or LCDR3.

In some embodiments, the invention provides a monoclonal antibody that is an agonist of α71 integrin, or an antibody fragment thereof, wherein the antibody or the antibody fragment comprises a heavy chain variable (VH) region and a light chain variable (VL) region, wherein (i) the VH region amino acid sequence comprises a HCDR1 sequence comprising SEQ ID NO: 14 with an amino acid substitution at its eight amino acid residue, HCDR2 of SEQ ID NO: 3 and HCDR3 of SEQ ID NO: 4, SEQ ID NO: 66 or SEQ ID NO: 68; and the VL region amino acid sequence comprises LCDR1 of SEQ ID NO: 5, SEQ ID NO: 69 or SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein the VH region amino acid sequence comprises (i) SEQ ID NO: 8, or an amino acid sequence that is at least 95%, 96%, 97%, 98% or 99% identical to the amino acid sequence of SEQ ID NO: 8; (ii) SEQ ID NO: 16, or an amino acid sequence that is at least 95%, 96%, 97%, 98% or 99% identical to the amino acid sequence of SEQ ID NO: 16; or (iii) SEQ ID NO: 67, or an amino acid sequence that is at least 95%, 96%, 97%, 98% or 99% identical to the amino acid sequence of SEQ ID NO: 67.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, SEQ ID NO: 14 or SEQ ID NO: 65, HCDR2 of SEQ ID NO: 3 and HCDR3 of SEQ ID NO: 4, SEQ ID NO: 15, SEQ ID NO: 66 or SEQ ID NO: 68; and the VL region amino acid sequence comprises LCDR1 of SEQ ID NO: 5, SEQ ID NO: 69 or SEQ ID NO: 71, LCDR2 of SEQ ID NO: 6 and LCDR3 of SEQ ID NO: 7.

In some embodiments, the invention provides a monoclonal antibody that is an agonist of α71 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 15; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α71 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 15; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 15; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 66; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 66; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 66; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 68; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 68; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α71 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 2, HCDR2 of SEQ ID NO: 3 and HCDR3 of SEQ ID NO: 68; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α71 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 15; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 15; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 15; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 66; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 66; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 66; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 68; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 68; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α71 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 14, HCDR2 of SEQ ID NO: 3 and HCDR3 of SEQ ID NO: 68; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 15; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 15; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 15; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 66; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 66; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 66; and the VL region amino acid sequence comprises LCDR1 of SEQ ID NO: 71, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 68; and the VL region amino acid sequence comprises LCDR1 of SEQ ID NO: 5, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 68; and the VL region amino acid sequence comprises LCDR1 of SEQ ID NO: 69, LCDR2 of SEQ ID NO: 6 and LCDR3 of SEQ ID NO: 7.

In some embodiments, the invention provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises HCDR1 of SEQ ID NO: 65, HCDR2 of SEQ ID NO: 3 and HCDR3 of SEQ ID NO: 68; and the VL region amino acid sequence comprises LCDR1 of SEQ ID NO: 71, LCDR2 of SEQ ID NO: 6 and LCDR3 of SEQ ID NO: 7.

In some embodiments, the invention encompasses a monoclonal antibody that is an agonist of α7β1 integrin, or an antibody fragment thereof, wherein the antibody or the antibody fragment comprises a light chain variable (VL) region and a heavy chain variable (VH) region, wherein the VL region amino acid sequence comprises (i) SEQ ID NO: 9, or an amino acid sequence that is at least 95%, 96%, 97%, 98% or 99% identical to the amino acid sequence of SEQ ID NO: 9; (ii) SEQ ID NO: 17, or an amino acid sequence that is at least 95%, 96%, 97%, 98% or 99% identical to the amino acid sequence of SEQ ID NO: 17; (iii) SEQ ID NO: 70, or an amino acid sequence that is at least 95%, 96%, 97%, 98% or 99% identical to the amino acid sequence of SEQ ID NO: 70; or (iv) SEQ ID NO: 72, or an amino acid sequence that is at least 95%, 96%, 97%, 98% or 99% identical to the amino acid sequence of SEQ ID NO: 72.

The invention further provides a monoclonal antibody that is an agonist of α7β1 integrin, or an antibody fragment thereof, wherein the antibody or the antibody fragment comprises a heavy chain variable (VH) region and a light chain variable (VL) region, wherein (i) the VH region amino acid sequence comprises SEQ ID NO: 8, or an amino acid sequence that is at least 95%, 96%, 97%, 98% or 99% identical to the amino acid sequence of SEQ ID NO: 8; and the VL region amino acid sequence comprises SEQ ID NO: 9, or an amino acid sequence that is at least 95%, 96%, 97%, 98% or 99% identical to the amino acid sequence of SEQ ID NO: 9; (ii) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 17, or an amino acid sequence that is at least 95%, 96%, 97%, 98% or 99% identical to the amino acid sequence of SEQ ID NO: 17; (iii) the VH region amino acid sequence comprises SEQ ID NO:

67, or an amino acid sequence that is at least 95%, 96%, 97%, 98% or 99% identical to the amino acid sequence of SEQ ID NO: 67; and the VL region amino acid sequence comprises SEQ ID NO: 17, or an amino acid sequence that is at least 95%, 96%, 97%, 98% or 99% identical to the amino acid sequence of SEQ ID NO: 17; (iv) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 70, or an amino acid sequence that is at least 95%, 96%, 97%, 98% or 99% identical to the amino acid sequence of SEQ ID NO: 70; or (v) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 72, or an amino acid sequence that is at least 95%, 96%, 97%, 98% or 99% identical to the amino acid sequence of SEQ ID NO: 72.

In some embodiments, provided herein is a monoclonal antibody that is an agonist of α7β1 integrin, or an antibody fragment thereof, wherein the antibody comprises a heavy chain and a light chain, (i) wherein the heavy chain amino acid sequence comprises SEQ ID NO: 18, and the light chain amino acid sequence comprises SEQ ID NO: 19; (ii) wherein the heavy chain amino acid sequence comprises SEQ ID NO: 45, and the light chain amino acid sequence comprises SEQ ID NO: 53; (iii) wherein the heavy chain amino acid sequence comprises SEQ ID NO: 18, and the light chain amino acid sequence comprises SEQ ID NO: 62; (iv) wherein the heavy chain amino acid sequence comprises SEQ ID NO: 18, and the light chain amino acid sequence comprises SEQ ID NO: 63.

In some embodiments, provided herein is a monoclonal antibody that is an agonist of α7β1 integrin, or an antibody fragment thereof, wherein the antibody is hIgG4-1, hIgG4-2, hIgG4-3, hIgG4-4, hIgG4-5, hIgG4-6, hIgG4-7, hIgG4-8, hIgG4-9, hIgG4-10, hIgG4-11, hIgG4-12, hIgG4-13, hIgG4-14, hIgG4-15, hIgG4-16, hIgG4-17, hIgG4-18, hIgG4-19, hIgG4-20, hIgG4-21, hIgG4-22, hIgG4-23, hIgG4-24, hIgG4-25, hIgG4-26, hIgG4-27, hIgG4-28, hIgG4-29, hIgG4-30, hIgG4-31, hIgG4-32, hIgG4-33, hIgG4-34, hIgG4-35, hIgG4-36, hIgG4-37, hIgG4-38, hIgG4-39, hIgG4-40, hIgG4-41, hIgG4-42, hIgG4-43, hIgG4-44, hIgG4-45, hIgG4-46, hIgG4-47, hIgG4-48, or hIgG4-49. The combinations of heavy chain and light chain sequences forming these antibodies are provided in Table 10.

In some embodiments, an anti-α7 antibody or an α7-binding antibody fragment comprises a polypeptide having one or more amino acid substitutions, deletions or insertions as compared to a polypeptide having an amino acid sequence of one or more of SEQ ID NOs: 2-9, 14-19 and 31-72. For example, an anti-α7 antibody or an α7-binding antibody fragment may have 1, 2, 3, 4, 5, 6, 7, 8, 9, 10, or more amino acid substitutions, deletions or insertions. Substitutions, deletions or insertions may be introduced by standard techniques, such as site-directed mutagenesis or PCR-mediated mutagenesis of a nucleic acid molecule encoding a polypeptide of an anti-α7 antibody or an α7-binding antibody fragment.

In some embodiments, conservative amino acid substitutions are made at one or more positions in the amino acid sequences of antibodies or antibody fragments disclosed herein. A "conservative amino acid substitution" is one in which the amino acid residue is replaced with an amino acid residue having a similar side chain. In certain embodiments, conservative amino acid substitutions are made only in the FR sequences and not in the CDR sequences of an antibody or antibody fragment. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan; histidine). Thus, an amino acid residue in a polypeptide of an anti-α7 antibody or an α7-binding antibody fragment may be replaced with another amino acid residue from the same side chain family. In some embodiments, a string of amino acids can be replaced with a structurally similar string that differs in order and/or composition of side chain family members. In some embodiments, a substitution may replace the original amino acid residue with a relatively more hydrophobic amino acid residue. In some embodiments, a substitution may replace the original amino acid residue with a relatively less hydrophobic amino acid residue. Those skilled in the art will be able to evaluate whether an anti-α7 antibody or an α7-binding antibody fragment comprising a polypeptide having one or more amino acid substitutions, deletions or insertions as compared to a polypeptide having an amino acid sequence of one or more of SEQ ID NOs: 2-9, 14-19 and 31-72 binds α7 protein by utilizing art-recognized methods including, but not limited to, ELISAs, Western blots, phage display, etc.

Calculations of sequence homology or identity (the terms are used interchangeably herein) between sequences may be performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman et al. ((1970) J. Mol. Biol. 48:444-453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) is a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. ((1989) CABIOS 4:11-17) which has been incorporated into the ALIGN program (version 2.0), using a PAM120 weight residue table, a gap length penalty of 12 and a gap penalty of 4.

In some embodiments, an antibody is a monoclonal antibody. In some embodiments, an antibody is a polyclonal antibody. The term "monoclonal antibody" refers to a population of antibody molecules that contain only one species of an antigen binding site capable of immunoreacting with a particular epitope of an antigen. A monoclonal antibody composition thus typically displays a single binding affinity for a particular protein with which it immunoreacts.

In some embodiments, an antibody of the invention is humanized, chimeric or human.

In some embodiments, an antibody of the invention is a humanized antibody and an integrin agonist. "Humanized antibody" as the term is used herein refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. Humanized antibodies are typically less immunogenic to humans, relative to non-humanized antibodies, and thus offer therapeutic benefits in certain situations. Those skilled in the art will be aware of humanized antibodies, and will also be aware of suitable techniques for their generation. See for example, Hwang, W. Y. K., et al., Methods 36:35, 2005; Queen et al., Proc. Natl. Acad. Sci. USA, 86:10029-10033, 1989; Jones et al., Nature, 321:522-25, 1986; Riechmann et al., Nature, 332:323-27, 1988; Verhoeyen et al., Science, 239:1534-36, 1988; Orlandi et al., Proc. Natl. Acad. Sci. USA, 86:3833-37, 1989; U.S. Pat. Nos. 5,225,539; 5,530,101; 5,585,089; 5,693,761; 5,693,762; 6,180,370; and Selick et al., WO 90/07861, each of which is incorporated herein by reference in its entirety. In some embodiments, an antibody or antigen-binding fragment of the invention may comprise a VH region amino acid sequence that comprises HCDR1 of SEQ ID NO: 2, HCDR2 of SEQ ID NO: 3 and HCDR3 of SEQ ID NO: 4; and a VL region amino acid sequence that comprises LCDR1 of SEQ ID NO: 5, LCDR2 of SEQ ID NO: 6 and LCDR3 of SEQ ID NO: 7; and one or more human framework region sequences. In some embodiments, an antibody or antigen-binding fragment of the invention may comprise a VH region amino acid sequence that comprises HCDR1 of SEQ ID NO: 14, HCDR2 of SEQ ID NO: 3 and HCDR3 of SEQ ID NO: 15; and a VL region amino acid sequence that comprises LCDR1 of SEQ ID NO: 5, LCDR2 of SEQ ID NO: 6 and LCDR3 of SEQ ID NO: 7; and one or more human framework region sequences. In some embodiments, an antibody or antigen-binding fragment of the invention may comprise a VH region amino acid sequence that comprises HCDR1 of SEQ ID NO: 65, HCDR2 of SEQ ID NO: 3 and HCDR3 of SEQ ID NO: 66; and a VL region amino acid sequence that comprises LCDR1 of SEQ ID NO: 5, LCDR2 of SEQ ID NO: 6 and LCDR3 of SEQ ID NO: 7; and one or more human framework region sequences. In some embodiments, an antibody or antigen-binding fragment of the invention may comprise a VH region amino acid sequence that comprises HCDR1 of SEQ ID NO: 14, HCDR2 of SEQ ID NO: 3 and HCDR3 of SEQ ID NO: 68; and a VL region amino acid sequence that comprises LCDR1 of SEQ ID NO: 69, LCDR2 of SEQ ID NO: 6 and LCDR3 of SEQ ID NO: 7; and one or more human framework region sequences. In some embodiments, an antibody or antigen-binding fragment of the invention may comprise a VH region amino acid sequence that comprises HCDR1 of SEQ ID NO: 14, HCDR2 of SEQ ID NO: 3 and HCDR3 of SEQ ID NO: 68; and a VL region amino acid sequence that comprises LCDR1 of SEQ ID NO: 71, LCDR2 of SEQ ID NO: 6 and LCDR3 of SEQ ID NO: 7; and one or more human framework region sequences.

In some embodiments, an antibody of the invention is a chimeric antibody and an integrin agonist. "Chimeric antibody" as the term is used herein refers to an antibody that has been engineered to comprise at least one human constant region. For example, one or all the variable regions of the light chain(s) and/or one or all the variable regions of the heavy chain(s) of a mouse antibody (e.g., a mouse monoclonal antibody) may each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies, and will also be aware of suitable techniques for their generation. See, for example, Cabilly et al., U.S. Pat. No. 4,816,567; Shoemaker et al., U.S. Pat. No. 4,978,775; Beavers et al., U.S. Pat. No. 4,975,369; and Boss et al., U.S. Pat. No. 4,816,397, each of which is incorporated herein by reference in its entirety. In some embodiments, an antibody or antigen-binding fragment of the invention may comprise a VH region comprising SEQ ID NO: 8; a VL region comprising SEQ ID NO: 9, and a human constant region. In some embodiments, an antibody or antigen-binding fragment of the invention may comprise a VH region comprising SEQ ID NO: 16; a VL region comprising SEQ ID NO: 17, and a human constant region. In some embodiments, an antibody or antigen-binding fragment of the invention may comprise a VH region comprising SEQ ID NO: 67; a VL region comprising SEQ ID NO: 17, and a human constant region. In some embodiments, an antibody or antigen-binding fragment of the invention may comprise a VH region comprising SEQ ID NO: 16; a VL region comprising SEQ ID NO: 70, and a human constant region. In some embodiments, an antibody or antigen-binding fragment of the invention may comprise a VH region comprising SEQ ID NO: 16; a VL region comprising SEQ ID NO: 72, and a human constant region.

In some embodiments, a monoclonal antibody that is an agonist of $\alpha 7\beta 1$ integrin, or an antibody fragment thereof, may comprise an immunoglobulin constant region. In some embodiments, the immunoglobulin constant region is IgG1, IgG2, IgG3, IgG4, IgA1 or IgA2. In some embodiments, the immunoglobulin constant region is IgG1, IgG2, IgG3, IgG1null, IgG4 (S228P), IgA1 or IgA2. The antibody molecule or antigen-binding portion thereof may comprise an immunologically inert constant region. In some embodiments, a monoclonal antibody or an antibody fragment thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some embodiments, a monoclonal antibody or an antibody fragment thereof may comprise an immunoglobulin constant region comprising a wild-type human IgG2 constant region or a wild-type human IgG4 constant region. In some embodiments, a monoclonal antibody or an antibody fragment thereof may comprise an immunoglobulin constant region comprising an amino acid sequence of an Fc region of human IgG4, human IgG4 (S228P), human IgG2, human IgG1, human IgG1-3M or human IgG1-4M. For example, the human IgG4 (S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some embodiments, a position of an amino acid residue in a constant region of an immunoglobulin molecule is numbered according to EU nomenclature (Ward et al., 1995 Therap. Immunol. 2:77-94).

In some embodiments, a monoclonal antibody that is an agonist of α7β1 integrin, or an antibody fragment thereof, may comprise an immunoglobulin light chain constant region that is a kappa light chain constant region or a lambda light chain constant region.

In some embodiments, the invention provides a monoclonal antibody that is an agonist of α7β1 integrin, or an antibody fragment thereof, wherein the antibody or the antibody fragment binds specifically to an epitope of α7 protein. In some embodiments, an epitope of α7 protein bound by an antibody or antibody fragment is continuous. In some embodiments, an epitope of α7 protein bound by an antibody or antibody fragment is discontinuous.

In some embodiments, a monoclonal antibody that is an agonist of α7β1 integrin, or an antibody fragment thereof, binds specifically to the extracellular domain of α7 protein. α7 protein may have two different extracellular sequences (designated "X1" and "X2") due to post-transcriptional modifications. The region that is variable between the X1 and X2 sequences is located between the III and IV homology repeat domains of α7 protein, near the putative ligand binding site. In certain embodiments, a monoclonal antibody or an antibody fragment thereof that is an agonist of α7β1 integrin binds specifically to a region of α7 protein between the III and IV homology repeat domains near the putative ligand binding site. The X1 sequence consists of, consists essentially of, or comprises TARVELCAQGSADLAHL-DDGPYEAGGEKEQDPRLIPVPANSYFG (SEQ ID NO: 1). The X2 sequence consists of, consists essentially of, or comprises LLFVTNIDSSDPDQLVYKTLD-PADRLPGPAGDLALNSYLG (SEQ ID NO: 10). The X2 sequence is preferentially expressed in adult skeletal cells. In some embodiments, a monoclonal antibody that is an agonist of α7β1 integrin, or an antibody fragment thereof, binds specifically to an epitope of α7 protein that comprises, consists essentially of, or consists of SEQ ID NO: 10. In some embodiments, a monoclonal antibody that is an agonist of α7β1 integrin, or an antibody fragment thereof, binds specifically to an epitope of α7 protein that comprises, consists essentially of, or consists of 5-10, 10-15, 15-20, 20-25, 25-30, 30-35 or 35-40 amino acids of SEQ ID NO: 10. In some embodiments, a monoclonal antibody that is an agonist of α7β1 integrin, or an antibody fragment thereof, binds specifically to an epitope of α7 protein that comprises, consists essentially of, or consists of SEQ ID NO: 1. In some embodiments, a monoclonal antibody that is an agonist of α7β1 integrin, or an antibody fragment thereof, binds specifically to an epitope of α7 protein that comprises, consists essentially of, or consists of 5-10, 10-15, 15-20, 20-25, 25-30, 30-35, 35-40 or 40-44 amino acids of SEQ ID NO: 1.

In some embodiments, a monoclonal antibody that is an agonist of α7β1 integrin, or an antibody fragment thereof, binds specifically to an epitope of α7 protein that comprises, consists essentially of, or consists of 5-10, 10-15, 15-20, 20-25, 25-30, 30-35 or 35-40 amino acids of SEQ ID NO: 24.

In some embodiments, an antibody binds to a CALF-2 domain of α7 protein (e.g., human α7 protein).

In some embodiments, a monoclonal antibody that is an agonist of α7β1 integrin, or an antibody fragment thereof, binds specifically to an epitope of α7 protein, wherein the epitope comprises SWWP (SEQ ID NO: 25). In some embodiments, a monoclonal antibody that is an agonist of α7β1 integrin, or an antibody fragment thereof, binds specifically to an epitope of α7 protein, wherein the epitope comprises SWWP (SEQ ID NO: 25), and wherein the epitope comprises, consists essentially of, or consists of 5-10 or 10-15 amino acids of SEQ ID NO: 24. In some embodiments, a monoclonal antibody that is an agonist of α7β1 integrin, or an antibody fragment thereof, binds specifically to an epitope comprising the residues S977, W978, W979 and P980 of SEQ ID NO: 24. In some embodiments, a monoclonal antibody that is an agonist of α7β1 integrin, or an antibody fragment thereof, binds specifically to an epitope comprising the residues S977, W978, W979 and P980 of SEQ ID NO: 24, wherein the epitope comprises, consists essentially of, or consists of 5-10 or 10-15 amino acids of SEQ ID NO: 24. In some embodiments, a monoclonal antibody that is an agonist of α7β1 integrin, or an antibody fragment thereof, binds specifically to an epitope comprising the residues R958, M976, S977, W978, W979 and P980 of SEQ ID NO: 24. In some embodiments, a monoclonal antibody that is an agonist of α7β1 integrin, or an antibody fragment thereof, binds specifically to an epitope comprising the residues R958, M976, S977, W978, W979 and P980 of SEQ ID NO: 24, wherein the epitope comprises, consists essentially of, or consists of 6-10 or 10-15 amino acids of SEQ ID NO: 24.

In some embodiments, a monoclonal antibody that is an agonist of α7β1 integrin, or an antibody fragment thereof, binds specifically to an epitope disclosed herein and comprises a heavy chain variable (VH) region comprising an HCDR1, an HCDR2 and an HCDR3, and a light chain variable (VL) region comprising an LCDR1, an LCDR2 and an LCDR3, (i) wherein the HCDR3 comprises SEQ ID NO: 15; and/or wherein the LCDR3 comprises SEQ ID NO: 7; (ii) wherein the HCDR3 comprises SEQ ID NO: 66; and/or wherein the LCDR3 comprises SEQ ID NO: 7; or (iii) wherein the HCDR3 comprises SEQ ID NO: 68; and/or wherein the LCDR3 comprises SEQ ID NO: 7. In some embodiments, a monoclonal antibody that is an agonist of α7β1 integrin, or an antibody fragment thereof, binds specifically to an epitope disclosed herein and comprises a VH region comprising an HCDR1, an HCDR2 and an HCDR3, and a VL region comprising an LCDR1, an LCDR2 and an LCDR3, wherein the HCDR2 comprises SEQ ID NO: 3; and/or wherein the LCDR2 comprises SEQ ID NO: 6. In some embodiments, a monoclonal antibody that is an agonist of α7β1 integrin, or an antibody fragment thereof, binds specifically to an epitope disclosed herein and comprises a VH region comprising an HCDR1, an HCDR2 and an HCDR3, and a VL region comprising an LCDR1, an LCDR2 and an LCDR3, (i) wherein the HCDR1 comprises SEQ ID NO: 14; and/or wherein the LCDR1 comprises SEQ ID NO: 5; (ii) wherein the HCDR1 comprises SEQ ID NO: 65; and/or wherein the LCDR1 comprises SEQ ID NO: 5; (iii) wherein the HCDR1 comprises SEQ ID NO: 14; and/or wherein the LCDR1 comprises SEQ ID NO: 69; or (iv) wherein the HCDR1 comprises SEQ ID NO: 14; and/or wherein the LCDR1 comprises SEQ ID NO: 71. In some embodiments, a monoclonal antibody that is an agonist of α7β1 integrin, or an antibody fragment thereof, binds specifically to an epitope disclosed herein and comprises a VH region comprising an HCDR1, an HCDR2 and an HCDR3, and a VL region comprising an LCDR1, an LCDR2 and an LCDR3, wherein the CDRs comprise one or more of the following amino acid sequences: HCDR1: SEQ ID NO: 14 or SEQ ID NO: 65, HCDR2: SEQ ID NO: 3, HCDR3: SEQ ID NO: 15, SEQ ID NO: 66 or SEQ ID NO: 68, LCDR1: SEQ ID NO: 5, SEQ ID NO: 69 or SEQ ID NO: 71, LCDR2: SEQ ID NO: 6, and LCDR3: SEQ ID NO: 7.

In some embodiments, an antibody or antibody fragment specifically binds to the laminin binding domain (or an epitope within the laminin binding domain) of α7 protein, α6 protein and/or α3 protein. In some cases, a monoclonal antibody or an antibody fragment thereof that is an agonist of α7β1 integrin binds specifically to an epitope of α7 protein that comprises, consists essentially of, or consists of 5-10, 10-15, 15-20, 20-25, 25-30, 30-35 or 35-40 amino acids of the laminin binding domain of α7 protein, α6 protein and/or α3 protein.

As used herein, the term "epitope" includes any protein determinant capable of specific binding to an immunoglobulin or an immunoglobulin fragment. Epitopic determinants usually consist of chemically active surface groupings of molecules such as amino acids or sugar side chains and usually have specific three dimensional structural characteristics, as well as specific charge characteristics. The term "epitope" also refers to a unit of structure conventionally bound by an immunoglobulin heavy chain variable (VH) region and a light chain variable (VL) region pair. An epitope may define the minimum binding site for an antibody, and thus represent the target of specificity of an antibody.

As used herein, the terms "immunological binding," and "immunological binding properties" refer to the non-covalent interactions of the type which occur between an immunoglobulin molecule (e.g., antibody) and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) *Annual Rev Biochem* 59:439-473). An antibody of the present invention is said to specifically bind to a PD-L1 epitope when the equilibrium binding constant ($K_d$) is ≤10 μM, preferably ≤10 nM, more preferably ≤10 nM, and most preferably ≤100 pM to about 1 pM, as measured by assays such as radioligand binding assays or similar assays known to those skilled in the art.

In certain aspects, an antibody of the invention is monovalent or bivalent and comprises a single or double chain. Functionally, the binding affinity of an antibody may be within the range of $10^{-5}$ M to $10^{-12}$ M. For example, the binding affinity of an antibody is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-8}$ M to $10^{-11}$ M, from $10^{-9}$ M to $10^{-11}$ M, from $10^{-10}$ M to $10^{-11}$ M, from $10^{-5}$ M to $10^{-10}$ M, from $10^{-6}$ M to $10^{-10}$ M, from $10^{-7}$ M to $10^{-10}$ M, from $10^{-8}$ M to $10^{-10}$ M, from $10^{-9}$ M to $10^{-10}$ M, from $10^{-5}$ M to $10^{-9}$ M, from $10^{-6}$ M to $10^{-9}$ M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$ M to $10^{-7}$ M, from $10^{-6}$ M to $10^{-7}$ M or from $10^{-5}$ M to $10^{-6}$ M.

Effects of Pharmaceutical Agents

The invention encompasses pharmaceutical agents (e.g., antibodies) that activate at least one of α7β1 integrin, α6β1 integrin and α3β1 integrin. In some embodiments, a pharmaceutical agent stimulates the binding of the integrin complex to the laminins. In some embodiments, a pharmaceutical agent stabilizes the active conformation of at least one of α7β1 integrin, α6β1 integrin and α3β1 integrin.

In certain aspects, a pharmaceutical agent increases the adhesion of a myoblast to laminin-α2 (merosin). In some cases, a myoblast is a healthy human myoblast or a healthy murine myoblast. In other cases, a myoblast is a human myoblast or a murine myoblast that is dystrophin deficient, comprises a mutation in dystrophin or comprises non-functioning dystrophin.

In some embodiments, a pharmaceutical agent increases the adhesion of a myotube to laminin-α2 (merosin). In some cases, a myotube is a healthy human myotube or a healthy murine myotube. In other cases, a myotube is a human myotube or a murine myotube that is dystrophin deficient, comprises a mutation in dystrophin or comprises non-functioning dystrophin.

In some aspects, activation of an integrin heterodimer by a pharmaceutical agent may have one or more of the following effects: i) enhancement of the strength of the bonds existing between muscular cells, myoblast/myotubes and their extracellular environment; ii) enhancement of the synthesis of extracellular matrix by the muscular cells; iii) enhancement of survival of muscular cells; and iv) enhancement of the recruitment and migration of satellite cells that provide the regenerative capacity of skeletal muscle.

Nucleic Acid Molecules, Vectors, Host Cells and Methods of Producing Pharmaceutical Agents One aspect of the invention encompasses a nucleic acid molecule (e.g., an isolated nucleic acid molecule) encoding an antibody or an antibody fragment described herein (or a VH region, a VL region, or both a VH region and a VL region of an antibody or antibody fragment). In some embodiments, an isolated nucleic acid molecule encodes a VH region amino acid sequence comprising SEQ ID NO: 8, or an amino acid sequence that is at least 95%, 96%, 97%, 98% or 99% identical to the amino acid sequence of SEQ ID NO: 8. In some embodiments, an isolated nucleic acid molecule encodes a VH region amino acid sequence comprising SEQ ID NO: 16, or an amino acid sequence that is at least 95%, 96%, 97%, 98% or 99% identical to the amino acid sequence of SEQ ID NO: 16. In some embodiments, an isolated nucleic acid molecule encodes a VH region amino acid sequence comprising SEQ ID NO: 67, or an amino acid sequence that is at least 95%, 96%, 97%, 98% or 99% identical to the amino acid sequence of SEQ ID NO: 67. In some embodiments, an isolated nucleic acid molecule encodes a VL region amino acid sequence comprising SEQ ID NO: 9, or an amino acid sequence that is at least 95%, 96%, 97%, 98% or 99% identical to the amino acid sequence of SEQ ID NO: 9. In some embodiments, an isolated nucleic acid molecule encodes a VL region amino acid sequence comprising SEQ ID NO: 17, or an amino acid sequence that is at least 95%, 96%, 97%, 98% or 99% identical to the amino acid sequence of SEQ ID NO: 17. In some embodiments, an isolated nucleic acid molecule encodes a VL region amino acid sequence comprising SEQ ID NO: 70, or an amino acid sequence that is at least 95%, 96%, 97%, 98% or 99% identical to the amino acid sequence of SEQ ID NO: 70. In some embodiments, an isolated nucleic acid molecule encodes a VL region amino acid sequence comprising SEQ ID NO: 72, or an amino acid sequence that is at least 95%, 96%, 97%, 98% or 99% identical to the amino acid sequence of SEQ ID NO: 72.

In some embodiments, an isolated nucleic acid molecule encodes (i) a VH region amino acid sequence comprising SEQ ID NO: 8, or an amino acid sequence that is at least 95%, 96%, 97%, 98% or 99% identical to the amino acid sequence of SEQ ID NO: 8; and (ii) a VL region amino acid sequence comprising SEQ ID NO: 9, or an amino acid sequence that is at least 95%, 96%, 97%, 98% or 99% identical to the amino acid sequence of SEQ ID NO: 9. In some embodiments, an isolated nucleic acid molecule encodes (i) a VH region amino acid sequence comprising SEQ ID NO: 16, or an amino acid sequence that is at least 95%, 96%, 97%, 98% or 99% identical to the amino acid sequence of SEQ ID NO: 16; and (ii) a VL region amino acid sequence comprising SEQ ID NO: 17, or an amino acid sequence that is at least 95%, 96%, 97%, 98% or 99% identical to the amino acid sequence of SEQ ID NO: 17. In some embodiments, an isolated nucleic acid molecule encodes (i) a VH region amino acid sequence comprising SEQ ID NO: 67, or an amino acid sequence that is at least 95%, 96%, 97%, 98% or 99% identical to the amino acid sequence of SEQ ID NO: 67; and (ii) a VL region amino acid sequence comprising SEQ ID NO: 17, or an amino acid sequence that is at least 95%, 96%, 97%, 98% or 99% identical to the amino acid sequence of SEQ ID NO: 17. In some embodiments, an isolated nucleic acid molecule encodes (i) a VH region amino acid sequence comprising SEQ ID NO: 16, or an amino acid sequence that is at least 95%, 96%, 97%, 98% or 99% identical to the amino acid sequence of SEQ ID NO: 16; and (ii) a VL region amino acid sequence comprising SEQ ID NO: 70, or an amino acid sequence that is at least 95%, 96%, 97%, 98% or 99% identical to the amino acid sequence of SEQ ID NO: 70. In some embodiments, an isolated nucleic acid molecule encodes (i) a VH region amino acid sequence comprising SEQ ID NO: 16, or an amino acid sequence that is at least 95%, 96%, 97%, 98% or 99% identical to the amino acid sequence of SEQ ID NO: 16; and (ii) a VL region amino acid sequence comprising SEQ ID NO: 72, or an amino acid sequence that is at least 95%, 96%, 97%, 98% or 99% identical to the amino acid sequence of SEQ ID NO: 72.

Further provided herein is a nucleic acid molecule (e.g., an isolated nucleic acid molecule) encoding (i) a heavy chain, (ii) a light chain, or (iii) both a heavy chain and a light chain of an antibody or an antibody fragment disclosed herein. In some embodiments, an isolated nucleic acid molecule encodes a heavy chain amino acid sequence comprising SEQ ID NO: 18, or an amino acid sequence that is at least 95%, 96%, 97%, 98% or 99% identical to the amino acid sequence of SEQ ID NO: 18. In some embodiments, an isolated nucleic acid molecule encoding a heavy chain comprises SEQ ID NO: 20 or a nucleotide sequence that is at least 95%, 96%, 97%, 98% or 99% identical to the nucleotide sequence of SEQ ID NO: 20. In some embodiments, an isolated nucleic acid molecule encodes a heavy chain amino acid sequence comprising SEQ ID NO: 45, or an amino acid sequence that is at least 95%, 96%, 97%, 98% or 99% identical to the amino acid sequence of SEQ ID NO: 45. In some embodiments, an isolated nucleic acid molecule encodes a light chain amino acid sequence comprising SEQ ID NO: 19, or an amino acid sequence that is at least 95%, 96%, 97%, 98% or 99% identical to the amino acid sequence of SEQ ID NO: 19. In some embodiments, an isolated nucleic acid molecule encoding a light chain comprises SEQ ID NO: 21 or a nucleotide sequence that is at least 95%, 96%, 97%, 98% or 99% identical to the nucleotide sequence of SEQ ID NO: 21. In some embodiments, an isolated nucleic acid molecule encodes a light chain amino acid sequence comprising SEQ ID NO: 53, or an amino acid sequence that is at least 95%, 96%, 97%, 98% or 99% identical to the amino acid sequence of SEQ ID NO: 53. In some embodiments, an isolated nucleic acid molecule encodes a light chain amino acid sequence comprising SEQ ID NO: 62, or an amino acid sequence that is at least 95%, 96%, 97%, 98% or 99% identical to the amino acid sequence of SEQ ID NO: 62. In some embodiments, an isolated nucleic acid molecule encodes a light chain amino acid sequence comprising SEQ ID NO: 63, or an amino acid sequence that is at least 95%, 96%, 97%, 98% or 99% identical to the amino acid sequence of SEQ ID NO: 63.

In some embodiments, an isolated nucleic acid molecule encodes (i) a heavy chain amino acid sequence comprising SEQ ID NO: 18, or an amino acid sequence that is at least 95%, 96%, 97%, 98% or 99% identical to the amino acid sequence of SEQ ID NO: 18; and (ii) a light chain amino acid sequence comprising SEQ ID NO: 19, or an amino acid sequence that is at least 95%, 96%, 97%, 98% or 99% identical to the amino acid sequence of SEQ ID NO: 19. In some embodiments, an isolated nucleic acid molecule comprises (i) SEQ ID NO: 20 or a nucleotide sequence that is at least 95%, 96%, 97%, 98% or 99% identical to the nucleotide sequence of SEQ ID NO: 20; and (ii) SEQ ID NO: 21 or a nucleotide sequence that is at least 95%, 96%, 97%, 98% or 99% identical to the nucleotide sequence of SEQ ID NO: 21. In some embodiments, an isolated nucleic acid molecule encodes (i) a heavy chain amino acid sequence comprising SEQ ID NO: 45, or an amino acid sequence that is at least 95%, 96%, 97%, 98% or 99% identical to the amino acid sequence of SEQ ID NO: 45; and (ii) a light chain amino acid sequence comprising SEQ ID NO: 53, or an amino acid sequence that is at least 95%, 96%, 97%, 98% or 99% identical to the amino acid sequence of SEQ ID NO: 53. In some embodiments, an isolated nucleic acid molecule encodes (i) a heavy chain amino acid sequence comprising SEQ ID NO: 18, or an amino acid sequence that is at least 95%, 96%, 97%, 98% or 99% identical to the amino acid sequence of SEQ ID NO: 18; and (ii) a light chain amino acid sequence comprising SEQ ID NO: 62, or an amino acid sequence that is at least 95%, 96%, 97%, 98% or 99% identical to the amino acid sequence of SEQ ID NO: 62. In some embodiments, an isolated nucleic acid molecule encodes (i) a heavy chain amino acid sequence comprising SEQ ID NO: 18, or an amino acid sequence that is at least 95%, 96%, 97%, 98% or 99% identical to the amino acid sequence of SEQ ID NO: 18; and (ii) a light chain amino acid sequence comprising SEQ ID NO: 63, or an amino acid sequence that is at least 95%, 96%, 97%, 98% or 99% identical to the amino acid sequence of SEQ ID NO: 63.

The invention also encompasses an expression vector comprising a nucleic acid molecule described herein. In certain vectors, a nucleic acid molecule is operatively linked to one or more regulatory sequences suitable for expression of the nucleic acid segment in a host cell. In some cases, an expression vector comprises sequences that mediate replication and comprises one or more selectable markers.

The invention further provides a recombinant host cell comprising an expression vector disclosed herein. An expression vector can be transfected into a host cell by standard techniques. Non-limiting examples include electroporation, calcium-phosphate precipitation, DEAE-dextran transfection and the like.

In some aspects, the invention contemplates a method for producing an antibody or an antibody fragment that is an agonist of α7β1 integrin, the method comprising: culturing a recombinant host cell comprising an expression vector described herein under conditions whereby the nucleic acid segment is expressed, thereby producing the antibody or the antibody fragment that is an agonist of α7β1 integrin. Anti-α7 antibodies and α7-binding fragments thereof can be produced by any of a variety of methods known to those skilled in the art. In certain embodiments, anti-α7 antibodies and α7-binding antibody fragments can be produced recombinantly. For example, nucleic acid sequences encoding one or more of SEQ ID NOs: 2-9, 14-19 and 31-72, or portions thereof, may be introduced into a bacterial cell (e.g., *E. coli, B. subtilis*) or a eukaryotic cell (e.g., a yeast such as *S. cerevisiae*, or a mammalian cell such as a CHO cell line, various Cos cell lines, a HeLa cell, various myeloma cell lines, or a transformed B-cell or hybridoma), or into an in vitro translation system, and the translated polypeptide may be isolated. In some embodiments, antibody light chain proteins and heavy chain proteins are produced in a cell with a leader sequence (also referred to as a signal sequence) that is removed upon production of a mature anti-α7 antibody or α7-binding fragment thereof. In some embodiments, the leader sequence is MDPKGSLSWRILLFLSLAFELSYG (SEQ ID NO: 22) or METDTLLLWVLLLWVPGSTG (SEQ ID NO: 23).

Those skilled in the art will be able to determine whether an antibody or fragment comprising a given polypeptide sequence binds to α7 protein without undue experimentation using standard methodologies such as, without limitation, Western blots, ELISA assays, and the like.

Uses of Pharmaceutical Agents

The invention encompasses methods and uses of the pharmaceutical agents described herein for providing a therapeutic benefit to a subject with a disorder or a disease. In some aspects, a method comprises administering to a subject in need a therapeutically effective amount of a pharmaceutical agent (e.g., an antibody or an antibody fragment) described herein (e.g., an agonist of at least one of α7β1 integrin, α6β1 integrin and α3β1), thereby treating the disorder or the disease in the subject. The disorder or the disease can be characterized by a malfunction of α7β1 integrin in the subject. For example, the subject may have a mutation in α7β1 integrin. The subject may not have sufficient α7β1 integrin. The disorder or the disease can be characterized by a dystrophin deficiency in the subject. The disorder or the disease can be characterized by a mutation in dystrophin in the subject. The disorder or the disease can be characterized by non-functioning dystrophin in the subject. The disorder or the disease can be characterized by a muscle dysfunction other than α7β1 malfunction, or dystrophin deficiency, mutation, or non-function in the subject.

In some embodiments, the muscle dysfunction in a subject is caused by or associated with one or more of: cancer, congestive heart failure, chronic obstructive pulmonary disease, chronic kidney disease, HIV infection/AIDS, anorexia nervosa, bulimia, malnutrition, exposure, nausea, type I diabetes, type II diabetes, metabolic syndrome, cachexia, anemia, heart failure, high blood pressure, rhabdomyolysis, sepsis, sarcopenia, physical inactivity, damage due to excess physical activity, hypothermia, hyperthermia, injury, denervation, amyotrophic lateral sclerosis, multiple sclerosis, spinal muscular atrophy, alcohol-associated myopathy, burn-associated myopathy, stroke, steroid therapy or the withdrawal of steroid therapy, dermatomyositis, Guillain-Barré syndrome, neuropathy, osteoarthritis, infection, polio, polymyositis, inflammation, rheumatoid arthritis, hypocholesterolemia, electrical injury, heat stroke, prolonged immobilization, lack of blood flow to a limb, or contact with venom. In some embodiments, a method of the invention further comprises identifying a subject having or at risk of having a muscle dysfunction.

In some embodiments, a disease that can be treated by the methods and compositions of the invention is a muscle wasting disease. In some cases, a muscle wasting disease is a dystroglycan deficiency, a sarcoglycan deficiency or a merosin deficiency. In one example, a muscle wasting disease can be a muscular dystrophy. Non-limiting examples of muscular dystrophy include Duchenne muscular dystrophy (DMD), Becker muscular dystrophy, merosin-deficient congenital muscular dystrophy type 1A and limb-girdle muscular dystrophy. In some embodiments, a method of the invention further comprises identifying a subject having or at risk of having a muscle wasting disease.

In some embodiments, the efficacy of a composition of the invention on treating a muscle wasting disease may be analyzed by using an animal model. Non-limiting examples of animal models of DMD include the mouse model Mdx/C57BL/10 (affected protein: dystrophin), the mouse model Mdx/D2 (affected protein: dystrophin), the mouse model mdx-utrn−/− (affected proteins: dystrophin and utrophin), and the rat model Mdx knockout rat (affected protein: dystrophin). A non-limiting example of an animal model of limb girdle muscular dystrophy is the Sgca-null mouse (affected protein: alpha-sarcoglycan). A non-limiting example of an animal model of merosin-deficient congenital muscular dystrophy type 1A (MDC1A) is the LAMA2dyw/dyw mouse (affected protein:laminin alpha2).

In some embodiments, administering a pharmaceutical agent described herein to a subject in need thereof reverses, stabilizes or slows muscle wasting or muscle dysfunction in the subject. In other embodiments, administering a pharmaceutical agent described herein to a subject in need thereof does not worsen muscle function in the subject. A method of the invention may further comprise measuring muscle function in the subject after the administration step, wherein the rate of worsening of muscle function is reduced.

In some embodiments, administering to the subject the therapeutically effective amount of the pharmaceutical agent can be effective to upregulate the activity and/or amount of α7β1 integrin in the subject effective to treat the malfunction of α7β1 integrin in the subject.

In some embodiments, administering to the subject the therapeutically effective amount of the pharmaceutical agent can be effective to upregulate activity and/or amount of α7β1 integrin in the subject. The upregulated activity and/or amount of α7β1 integrin in the subject can be effective to at least in part mitigate the effect of the dystrophin deficiency in the subject. The upregulated activity and/or amount of α7β1 integrin in the subject can be effective to at least in part mitigate the effect of the mutation in dystrophin in the subject. The upregulated activity and/or amount of α7β1 integrin in the subject can be effective to at least in part mitigate the effect of the non-functioning dystrophin in the subject.

In some embodiments, administering to the subject the therapeutically effective amount of the pharmaceutical agent can be effective to mitigate muscle injury in the subject. For example, administering to the subject the therapeutically effective amount of the pharmaceutical agent can be effective to mitigate eccentric muscle injury in the subject. Administering to the subject the therapeutically effective amount of the pharmaceutical agent can be effective to improve diaphragm muscle function in the subject.

In several embodiments, the method can include administering to the subject one or more other therapies. The one or more other therapies can be directed to muscular dystrophy or muscle wasting, for example, any conventional or experimental therapy for muscular dystrophy. The one or more other therapies can include medication, surgery with or without transplantation, a physical intervention such as physical therapy, or a medical device. For example, the one or more other therapies can include an anticonvulsant. The one or more other therapies can include an immunosuppressant. The one or more other therapies can include an antibiotic. The one or more other therapies can include quinine. The one or more other therapies can include therapy for management of congestive heart failure. The one or more other therapies can include a gene replacement therapy. The one or more other therapies can include an exon skipping therapy. The one or more other therapies can include a nonsense suppression therapy. The one or more other therapies can include therapy using an engineered nuclease. The one or more other therapies can include cell therapy using muscle precursor cells or stem cells. The one or more other therapies can include upregulation of utrophin. The one or more other therapies can include an anti-inflammatory. The one or more other therapies can include an antifibrotic. The one or more other therapies can include a steroid therapy. In some embodiments, a steroid therapy comprises a corticosteroid or an anabolic steroid. The one or more other therapies can include a myostatin blocker. The one or more other therapies can include insulin growth factor. The one or more other therapies can include a phosphodiesterase-5 inhibitor; an ACE inhibitor. The one or more other therapies can include induction of angiogenesis through delivery of vascular endothelial growth factor (VEGF). The one or more other therapies can include downregulation of VEGF decoy-receptor type 1 (VEGFR-1 or Flt-1). The one or more other therapies can include physical therapy; occupational therapy. The one or more other therapies can include surgery. The one or more other therapies can include orthotic intervention. The one or more other therapies can include speech therapy. The one or more other therapies can include respiratory therapy. The one or more other therapies can include a pacemaker. The one or more other therapies can include a respiratory assistance device.

In various embodiments, the method can further include administering to the subject one or more other therapies. The one or more other therapies can be directed to mitigating muscular dystrophy. The one or more other therapies can be directed to mitigating muscle wasting.

In some embodiments, the one or more other therapies can include one or more of, e.g.: an anticonvulsant; an immunosuppressant, e.g. prednisone and deflazacort; an antibiotic; and quinine.

In several embodiments, the one or more other therapies may include therapy for management of congestive heart failure, e.g., dilated cardiomyopathy, e.g., using anti-congestive medications and/or cardiac transplantation. Examples of therapies which may be used for congestive heart failure include, e.g.: angiotensin-converting enzyme (ACE) inhibitors (ACE-I); angiotensin receptor blockers (ARBs); beta-adrenergic blocking agents (beta blockers); hydralazine; nitrates such as isosorbide dinitrate; an aldosterone antagonist; digoxin; diuretics, e.g., loop diuretics, thiazide-like diuretics, and potassium-sparing diuretics; an anticoagulant; a vasopressin receptor antagonist, e.g., conivaptan; sacubitril/valsartan; ivabradine; iron supplementation; fluid restriction; and sodium restriction.

In various embodiments, the one or more other therapies can include one or more genetic therapies, e.g., gene replacement therapy. For example, one genetic therapy involves dystrophin gene replacement using virus vectors. For example, adeno-associated viruses including microdystrophins have been injected into a canine model of DMD, resulting in substantial benefit to muscle histopathology. Clinical trials are underway to replace defective genes in DMD human subjects with DMD using recombinant adeno-associated viruses. Examples include, e.g., rAAV2.5-CMV-Mini-dystrophy, rAAVrh74.MCK-Mini-dystrophy, and rAAV1.CMV.huFollistatin344.

In some embodiments, the one or more genetic therapies can include, e.g., exon skipping, in which synthetic antisense oligonucleotide sequences are used to update dystrophin gene mutations. Specific exons are skipped during pre-messenger RNA (pre-mRNA) splicing of the dystrophin gene, which restores the reading frame and partial production of an internally truncated protein. Exon skipping therapies can include agents for skipping, e.g.: exon 53, such as SRP4053 (Serapta), PRO053 (Prosensa), and NS-065/NCNP-01; exon 51, such as PRO051, eteplirsen (AVI-4658), and drisapersen (GSK2402968); exon 45, such as DS-5141, PRO045, and SRP4045; and exon 44, such as PRO044. For example, PRO051, a 2'-O-methyl-phosphorothioate oligoribonucleotide which skips exon 51 in dystrophin pre-mRNA has been injected into human DMD subjects, resulting in 17%-35% restoration of dystrophin. Further, for example, eteplirsen (AVI-4658) is a phosphoramidate morpholino oligomer which also skips exon 51 in dystrophin pre-mRNA.

In several embodiments, the one or more genetic therapies can include, e.g., nonsense suppression therapy. About 10%-15% of DMD cases are due to point mutations forming a premature stop codon. Such premature stop codons usually cause loss of the functional protein. Recognition of such premature stop codons can be mitigated by nonsense mutation suppression agents effective to restore translation and production of a modified dystrophin protein. Nonsense mutation suppression agents can include, e.g., aminoglycosides such as gentamicin, Ataluren (Translarna), and arbekacin sulfate (NPC-14).

In various embodiments, the one or more genetic therapies can include, e.g., using engineered nucleases such as CRISPR-Cas9. For example, mdx mice treated with RNA-guided clustered regularly interspaced short palindromic repeats-Cas9 endonucleases delivered by adeno-associated virus, mitigated dystrophic changes in skeletal muscle fibers, cardiomyocytes, and muscle satellite cells.

In some embodiments, the one or more other therapies can include one or more cell therapies, e.g., using muscle precursor cells or stem cells, e.g., myoblast transfer, intra-arterial transplantation of human leukocyte antigen-matched sibling donor mesoangioblasts, induced pluripotent stem cells, umbilical cord based allogenic mesenchymal stem cells, and bone marrow autologous and mononuclear stem cells.

In several embodiments, the one or more other therapies can include membrane stabilization and upregulation of cytoskeletal proteins. For example, upregulation of utrophin, alpha-7-beta-1 integrin, 110 biglycan, and sarcospan stabilized the sarcolemma in mdx mice. For example, the compounds SMT C1100 and SMT022357 were shown to target the utrophin-A promoter and increase the production of utrophin and reduce dystrophic changes in skeletal and cardiac muscle.

In various embodiments, the one or more other therapies can include one or more anti-inflammatory therapies. Anti-inflammatory drugs can include, e.g.: VBP15; givinostat (HDAC inhibitor); NEMO-binding domain peptide; CAT-1004 (Edasalonexent, NF-κB inhibitor); flavocoxid; TAS-205 (PDGD2 synthase inhibitor); idebenone; pentoxifylline; coenzyme Q10; N-acetylcysteine; green tea extract; melatonin; pentoxifylline; and oxatomide. For example, NF-κB inhibition using the NEMO-binding domain peptide resulted in improved pathology and muscle function in mouse models of muscular dystrophy.

In some embodiments, the one or more other therapies can include one or more antifibrotic therapies, e.g., TGF-β blockers such as losartan, an angiotensin II-type 1 receptor blocker that reduces the expression of TGF-β; lisinopril; HT-100 (halofuginone); FG-3019 (monoclonal antibody to CTGF); and targeted microRNAs.

In several embodiments, the one or more other therapies can include muscle regeneration therapies. For example, suitable agents can include: myostatin blockers such as ACE-031, MYO-029, follistatin, PF-06252616; and BMS-986089; or insulin growth factor, alone or further combined with mesenchymal stromal cells.

In various embodiments, the one or more other therapies can include treatment of muscle ischemia, e.g., by inhibition of phosphodiesterase-5 using tadalafil, sildenafil, and vardenafil; ACE inhibitors; induction of angiogenesis through delivery of vascular endothelial growth factor (VEGF); and downregulation of the VEGF decoy-receptor type 1 (VEGFR-1 or Flt-1).

In some embodiments, the one or more other therapies can include one or more physical interventions, e.g.: physical therapy, occupational therapy, surgery, orthotic intervention (e.g., ankle-foot orthosis), speech therapy, and respiratory therapy.

In several embodiments, the one or more other therapies can include one or more medical devices, e.g.: a pacemaker; or a respiratory assistance device such as a ventilator or a continuous positive airway pressure device.

The invention further provides a method of activating α7β1 integrin in a muscle cell of a subject, the method comprising: administering to the subject a therapeutically effective amount of a pharmaceutical agent (e.g., an antibody or an antibody fragment) described herein, thereby activating α7β1 integrin in a muscle cell of the subject.

The invention also provides a method of enhancing binding of α7β1 integrin to its ligand in a muscle cell of a subject, the method comprising: administering to the subject a therapeutically effective amount of a pharmaceutical agent (e.g., an antibody or an antibody fragment) described herein, thereby enhancing binding of α7β1 integrin to its ligand in a muscle cell of the subject.

As used herein, the term "patient in need" or "subject in need" refers to a patient or subject at risk of, or suffering from, a disease, disorder or condition that is amenable to treatment or amelioration with an agonist of an integrin heterodimer comprising a β1 protein or a composition comprising such an agonist provided herein. A patient or subject in need may, for instance, be a patient or subject diagnosed with a disease associated with the malfunction of α7β1 integrin, such as a muscle wasting disease. A subject may have a mutation or a malfunction in one of the proteins in the laminin/dystroglycan/sarcoglycan/dystrophin complex. In other embodiments, a subject may have a mutation or malfunction in laminin-α2 (merosin). "Subject" and "patient" are used interchangeably herein.

In certain embodiments, a subject may be a human, a non-human primate, a pig, a horse, a cow, a dog, a cat, a mouse or a rat.

As used herein, the term "effective amount" or "therapeutically effective amount" refers to the amount of a pharmaceutical agent, e.g., an antibody, which is sufficient to reduce or ameliorate the severity and/or duration of a disorder, e.g., muscular dystrophy, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody may, for example, enhance muscle regeneration, maintenance or repair, and/or relieve to some extent one or more of the symptoms associated with the muscle wasting disease.

In certain aspects, a subject in need thereof may be treated with a pharmaceutical agent described herein and an additional pharmaceutical agent that has a different mechanism of action (e.g., gene correction, increasing muscle regeneration or decreasing inflammation and fibrosis) that is used to treat muscle wasting disease.

The invention further contemplates a use of a pharmaceutical agent (e.g., an antibody or an antibody fragment) described herein in the manufacture of a medicament for treating a disorder or a disease characterized by a malfunction of α7β1 integrin in a subject. The invention also includes a use of a pharmaceutical agent (e.g., an antibody or an antibody fragment) described herein for treating a disorder or a disease characterized by a malfunction of α7β1 integrin in a subject.

Pharmaceutical Compositions

The pharmaceutical agents of the invention (also referred to herein as "active compounds"), and derivatives, fragments, analogs and homologs thereof, can be incorporated into pharmaceutical compositions suitable for administration. Such compositions typically comprise an antibody and a pharmaceutically acceptable carrier, diluent or excipient.

In some embodiments, a pharmaceutical composition comprises a pharmaceutical agent that is an agonist of α7β1 integrin. In other embodiments, a pharmaceutical composition comprises at least two, at least three or at least four different pharmaceutical agents that are agonists of at least one of α7β1 integrin, α6β1 integrin and α3β1 integrin. As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable." As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Some examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention may be formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primojel®, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical agents can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously.

The invention will be further described in the following examples, which do not limit the scope of the invention described in the claims.

TABLE 1A

Exemplary integrin alpha protein laminin binding head domain sequences

Integrin alpha7 head domain amino acid sequence
FNLDVMGALRKEGEPGSLFGFSVALHRQLQPRPQSWLLVGAPQA
LALPGQQANRTGGLFACPLSLEETDCYRVDIDQGADMQKESKEN TABLE 1A-continued Exemplary integrin alpha protein laminin binding head domain sequences QWLGVSVRSQGPGGKIVTCAHRYEARQRVDQILETRDMIGRCFV
LSQDLAIRDELDGGEWKFCEGRPQGHEQFGFCQQGTAAAFSPDS
HYLLFGAPGTYNWKGTARVELCAQGSADLAHLDDGPYEAGGEKE
QDPRLIPVPANSYFGFSIDSGKGLVRAEELSFVAGAPRANHKGA
VVILRKDSASRLVPEVMLSGERLTSGFGYSLAVADLNSDGWPDL
IVGAPYFFERQEELGGAVYVYLNQGGHWAGISPLRLCGSPDSMF
GISLAVLGDLNQDGFPDIAVGAPFDGDGKVFIYHGSSLGVVAKP
SQVLEGEAVGIKSFGYSLSGSLDMDGNQYPDLLVGSLADTAVLF
RARPIL (SEQ ID NO: 11)

Integrin alpha6 head domain amino acid sequence
FNLDTREDNVIRKYGDPGSLFGFSLAMHWQLQPEDKRLLLVGAP
RAEALPLQRANRTGGLYSCDITARGPCTRIEFDNDADPTSESKE
DQWMGVTVQSQGPGGKVVTCAHRYEKRQHVNTKQESRDIFGRCY
VLSQNLRIEDDMDGGDWSFCDGRLRGHEKFGSCQQGVAATFTKD
FHYIVFGAPGTYNWKGIVRVEQKNNTFFDMNIFEDGPYEVGGET
EHDESLVPVPANSYLGFSLDSGKGIVSKDEITFVSGAPRANHSG
AVVLLKRDMKSAHLLPEHIFDGEGLASSFGYDVAVVDLNKDGWQ
DIVIGAPQYFDRDGEVGGAVYVYMNQQGRWNNVKPIRLNGTKDS
MFGITVKNIGDINQDGYPDIAVGAPYDDLGKVFIYHGSANGINT
KPTQVLKGISPYFGYSIAGNMDLDRNSYPDVAVGSLSDSVTIFR
SRPVI (SEQ ID NO: 12)

Integrin alpha3 head domain amino acid sequence
FNLDTRFLVVKEAGNPGSLFGYSVALHRQTERQQRYLLLAGAPR
ELAVPDGYTNRTGAVYLCPLTAHKDDCERMNITVKNDPGHHIIE
DMWLGVTVASQGPAGRVLVCAHRYTQVLWSGSEDQRRMVGKCYV
RGNDLELDSSDDWQTYHNEMCNSNTDYLETGMCQLGTSGGFTQN
TVYFGAPGAYNWKGNSYMIQRKEWDLSEYSYKDPEDQGNLYIGY
TMQVGSFILHPKNITIVTGAPRHRHMGAVFLLSQEAGGDLRRRQ
VLEGSQVGAYFGSAIALADLNNDGWQDLLVGAPYYFERKEEVGG
AIYVFMNQAGTSFPAHPSLLLHGPSGSAFGLSVASIGDINQDGF
QDIAVGAPFEGLGKVYIYHSSSKGLLRQPQQVIHGEKLGLPGLA
TFGYSLSGQMDVDENFYPDLLVGSLSDHIVLLRARPVI
(SEQ ID NO: 13)

TABLE 1B

Exemplary integrin alpha protein CALF-1 domain sequence

DNVCKPKLEVSVDSDQKKIYIGDDNPLTLIVKAQNQGEGAYEAELI
VSIPLQADFIGVVRNNEALARLSCAFKTENQTRQVVCDLGNPMKAG
TQLLAGLRFSVHQQSEMDTSVKFDLQIQSSNLFDKVSPVVSHKVDL
A (SEQ ID NO: 73)

TABLE 1C

Exemplary integrin alpha protein CALF-2 domain sequence

VLAAVEIRGVSSPDHVFLPIPNWEHKENPETEEDVGPVVQHIYE
LRNNGPSSFSKAMLHLQWPYKYNNNTLLYILHYDIDGPMNCTSD
MEINPLRIKISSLQTTEKNDTVAGQGERDHLITKRDLALSEGDI
HTLGCGVAQCLKIVCQVGRLDRGKSAILYVKSLLWTETFMNKEN
QNHSYSLKSSASFNVIEFPYKNLPIEDITNSTLVTTNVTWGIQ
(SEQ ID NO: 74)

EXAMPLES

Example 1:81 Protein Agonist Provides Compensatory Effects in Cells with a Dystrophin Deficiency Myoblasts and myotubes from healthy and dystrophin deficient human patients were treated with the β1 agonist antibody TS2/16 (J. Immunol, 1984, 132:3011). Cell adhesion assays were used to evaluate the cell attachment to laminin through integrins. Microplates were coated overnight with 10 μg/ml merosin at 4° C., and blocked with 2% BSA/PBS for 30 min before the assay. Myoblast or myotube cells were detached and washed in PBS. After that, the cells were resuspended in IMEM at 1.0×10⁶ cells/ml, and fifty microliters of cell suspension and fifty microliters of antibody solution were added into the plate. The plates were incubated for one hour at 37° C. in humidified 5% carbon dioxide. Non-adherent cells were removed by centrifugation top side down at 58 g for 5 min. The attached cells were fixed and stained with 0.5% crystal violet (in 20% methanol and 1% formaldehyde) and the wells washed with PBS. Crystal violet was dissolved in 2% Triton-X in PBS. The relative number of cells in each well was evaluated by the absorbance at 595 nm in a microplate reader (Tecan).

Figure 1:
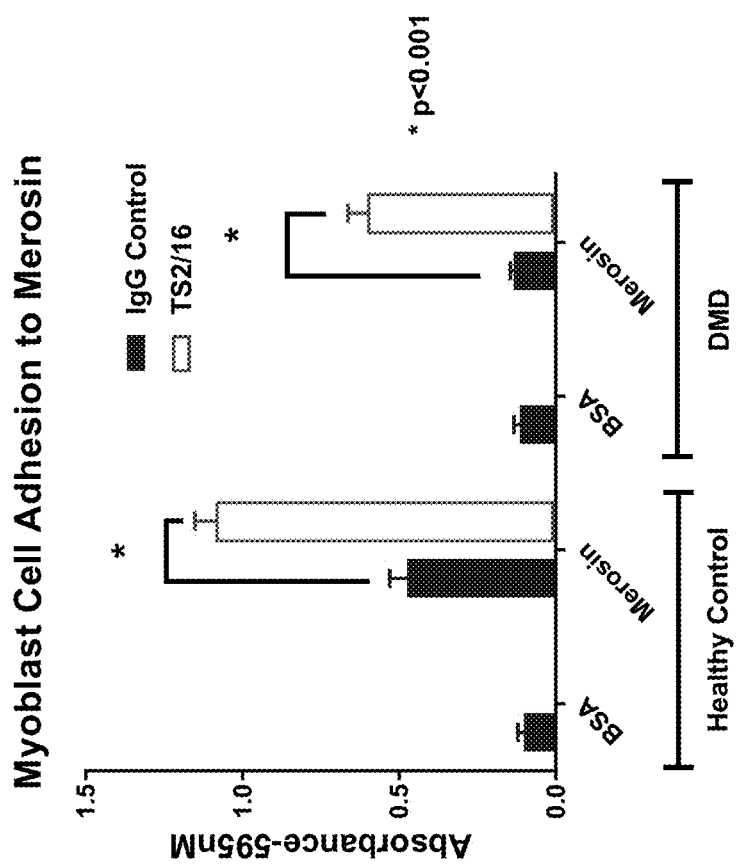
FIG. 1 is a graph showing that integrin β1 protein activation by a β1 agonist antibody (TS2/16) promotes human myoblast adhesion to merosin (laminin). "DMD" refers to myoblasts that are dystrophin deficient, possessing a mutation in dystrophin or non-functioning dystrophin.
Figure 2:
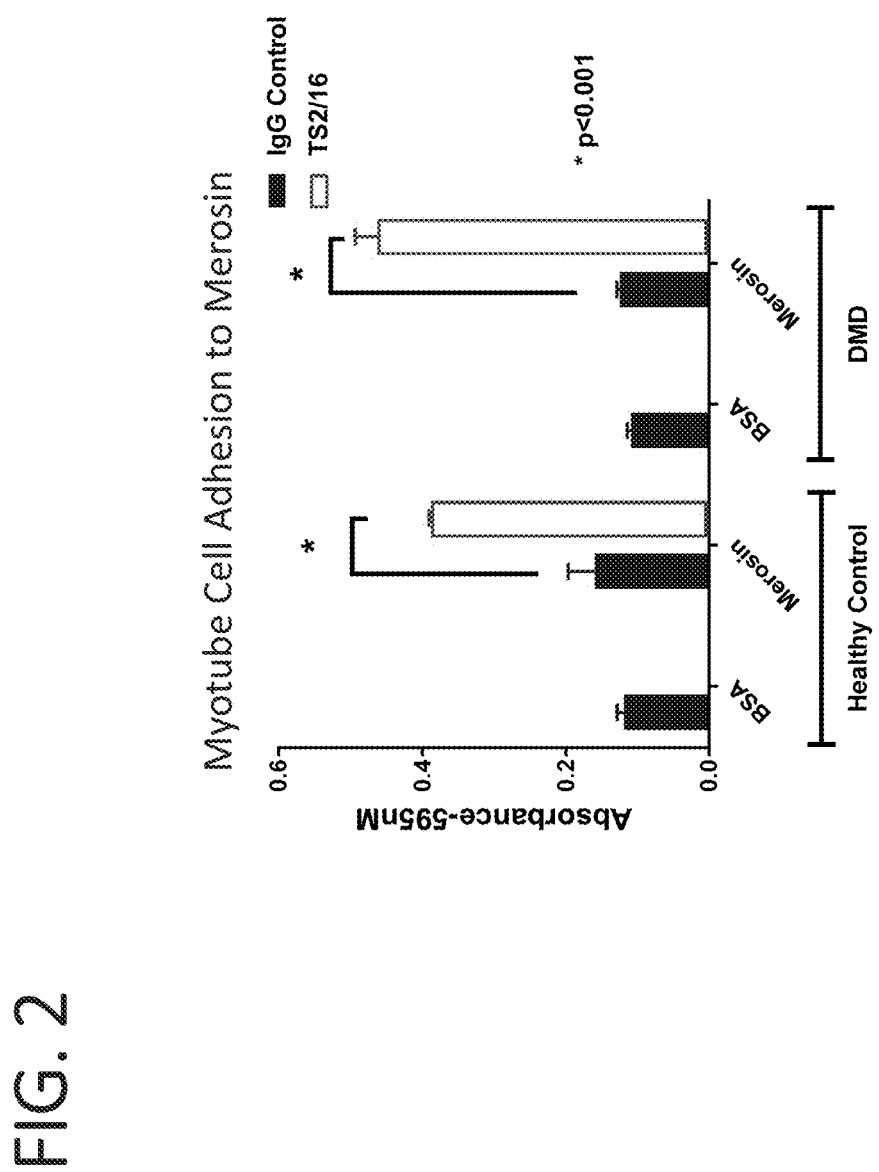
FIG. 2 is a graph showing that integrin β1 protein activation by a β1 agonist antibody (TS2/16) promotes human myotube adhesion to merosin (laminin). "DMD" refers to myoblasts that are dystrophin deficient, possessing a mutation in dystrophin or non-functioning dystrophin.
Figure 3:
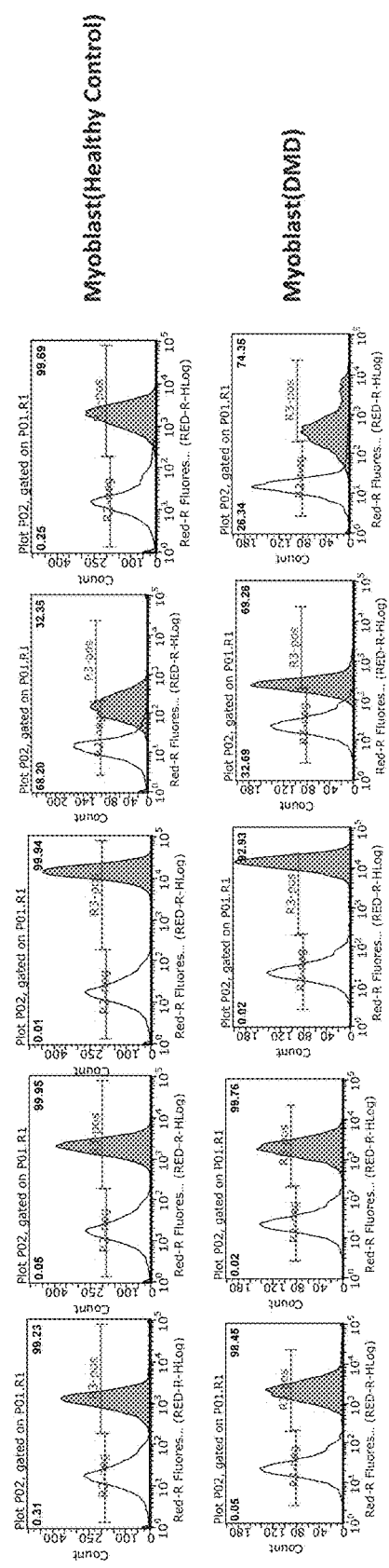
FIG. 3 is a series of graphs showing that myoblast cells express multiple laminin integrins (α3β1; α6β1; α7β1 and α6β4) as measured by FACS analysis.
Figure 4:
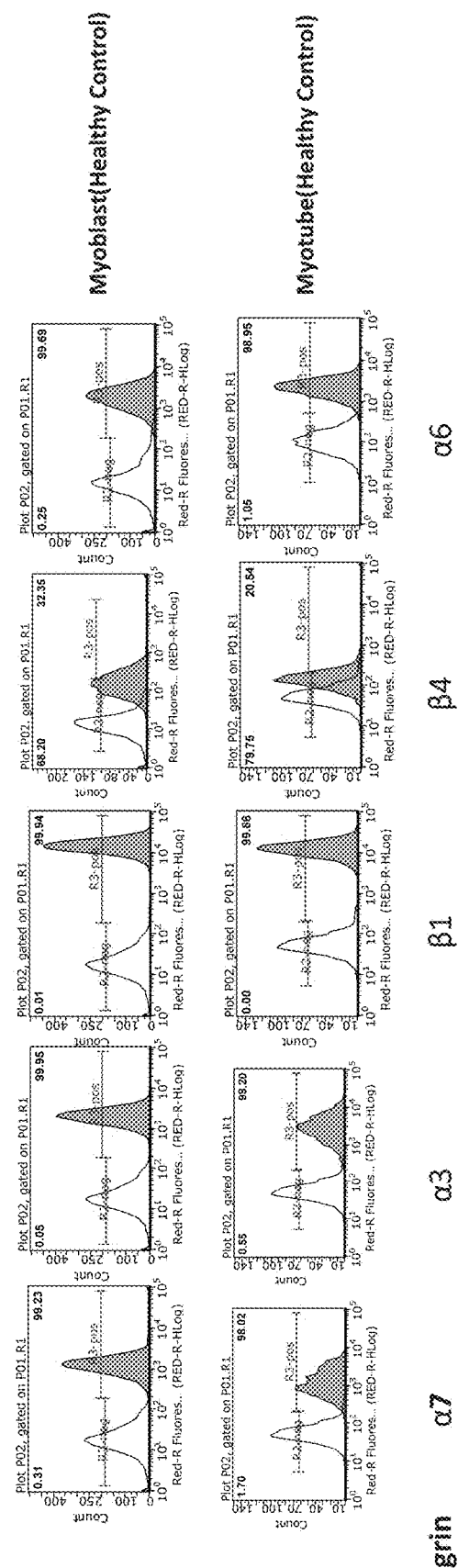
FIG. 4 is a series of graphs showing that myotube cells express multiple laminin integrins (α3β1; α6β1; α71 and α6β4) as measured by FACS analysis.
Figure 5:
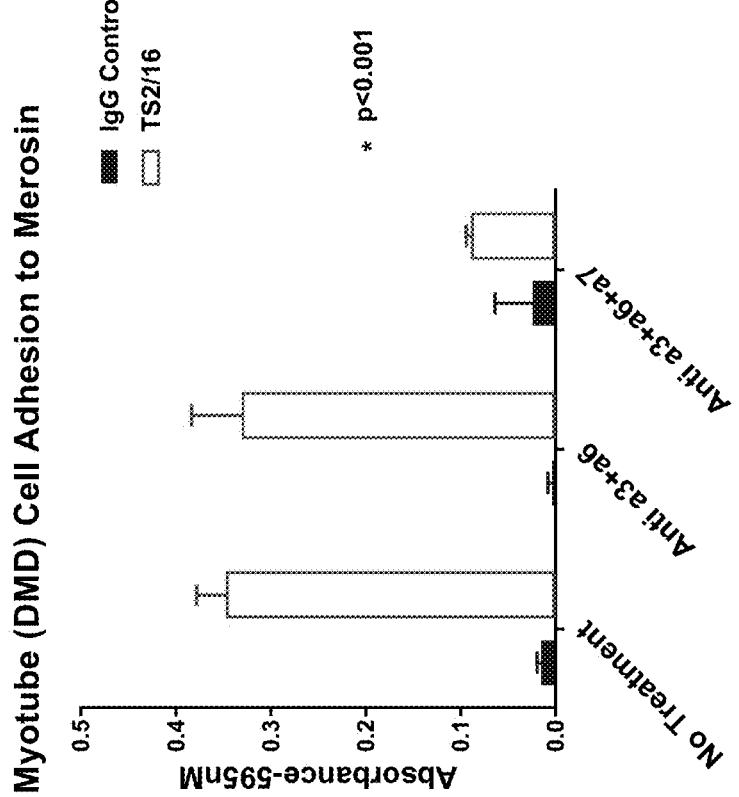
FIG. 5 is a graph showing that integrin α7β1 heterodimer activation by a β1 agonist antibody (TS2/16) promotes human myotube adhesion to merosin (laminin). "Anti a3+a6" refers to the combination of inhibitory antibodies against α3β1 and α6β1. "Anti a3+a6+a7" refers to the combination of inhibitory antibodies against α3b1, α6β1 and α7β1. "DMD" refers to myotubes that are dystrophin deficient, possessing a mutation in dystrophin or non-functioning dystrophin.

Treatment with TS2/16 promoted human myoblast adhesion to merosin (laminin) in both healthy control and dystrophin deficient myoblasts (FIG. 1) and myotubes (FIG. 2). α7β1 integrin is up-regulated upon differentiation into myotubes. Myotube adhesion to merosin can be enhanced by B1 activation. Human myoblast cells express multiple laminin integrins on the cell surface as determined by FACS (FIGS. 3 and 4). The enhanced cell adhesion mediated by β1 activation was mainly contributed by integrin α7β1 (FIG. 5) as it was not inhibited by functional blocking α3 and 6 antibodies, but blocked by a blocking α7 antibody.

Figure 6:
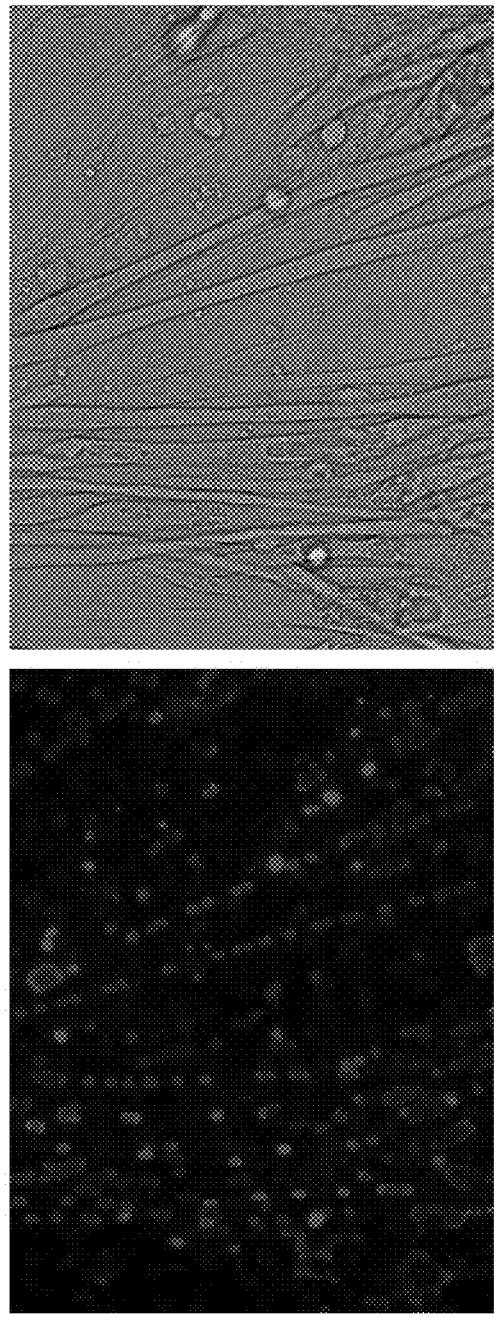
FIG. 6 shows photomicrographs depicting myotube formation of C2C12 cells five days after differentiation.
Figure 7:
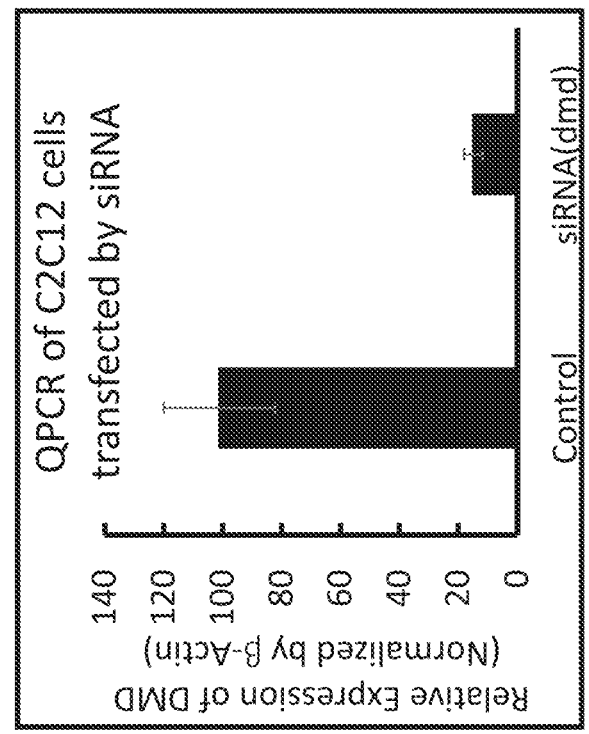
FIG. 7 is a graph showing relative expression of dystrophin as measured by QPCR (quantitative PCR) in C2C12 murine cells treated with either control siRNA or dystrophin-targeting siRNA.
Figure 8A:
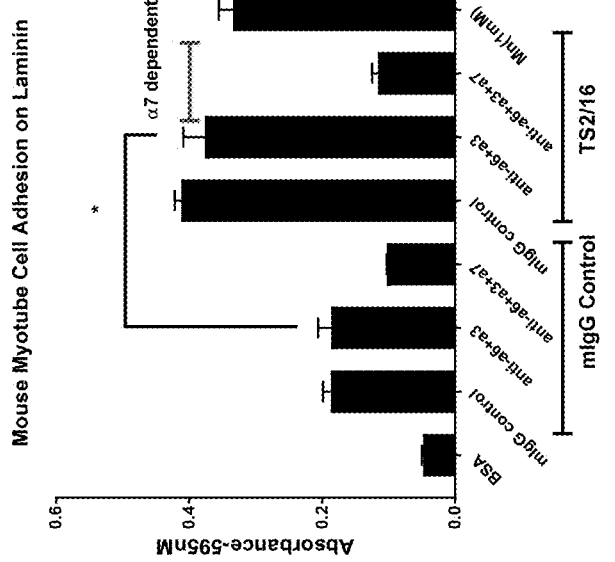
FIG. 8A is a graph showing that integrin β1 protein activation by a β1 agonist antibody (TS2/16) promotes murine myotube adhesion to laminin in C2C12 murine myotube cells treated with either control siRNA or dystrophin-targeting siRNA.
Figure 8B:
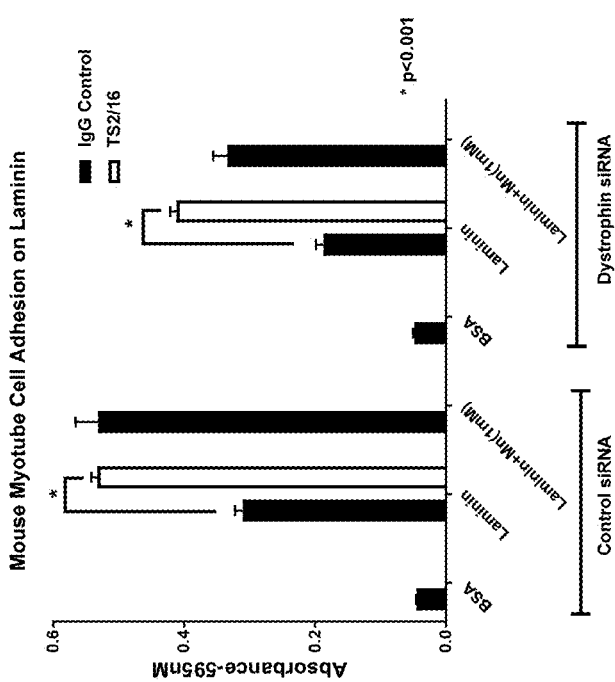
FIG. 8B is a graph showing that the adhesion to laminin is mainly contributed by α7β1 integrin upon stimulation by TS2/16. "Anti a3+a6" refers to the combination of inhibitory antibodies against α3β1 and α6β1. "Anti a3+a6+a7" refers to the combination of inhibitory antibodies against α3β1, α6β1 and α7β1. "DMD (KD)" refers to myotubes cells treated with dystrophin-targeting siRNA. Mn2+ was used as a pan-integrin activator to reach the maximum level of cell adhesion to merosin achievable.

The β1 agonist antibody TS2/16 also enhanced myotube adhesion to laminin in an α7β1-dependent manner in healthy murine myoblasts in which dystrophin expression was knocked down with siRNA. C2C12 cells (Nature, 1977, 270:725) are murine myoblasts expressing multiple laminin integrins. C2C12 cells express three laminin receptors (α3, α6 and α7β1) on their surface (J Cell Sci, 1996, 109:3139). α7A is upregulated during skeletal muscle differentiation. α7 expression levels in C2C12 cells increase during muscle differentiation (Xiao et al. (2003) J. Biol. Chem., 278:49780-49788). C2C12 cells were differentiated to myotubes (FIG. 6). Dystrophin expression in the myotubes was knocked down using siRNA (FIG. 7; Ghahramani Seno et al. (2008) Human Molecular Genetics, 17:2622-2632). TS2/16 enhanced murine myotube cell adhesion to laminin in murine myotubes treated with control siRNA and with dystrophin siRNA (FIG. 8A). The TS2/16-enhanced murine myotube cell adhesion to laminin was mainly contributed by integrin α7β1 (FIG. 8B).

Example 2: Generation of α7β1 Agonist Antibodies

Figure 9:
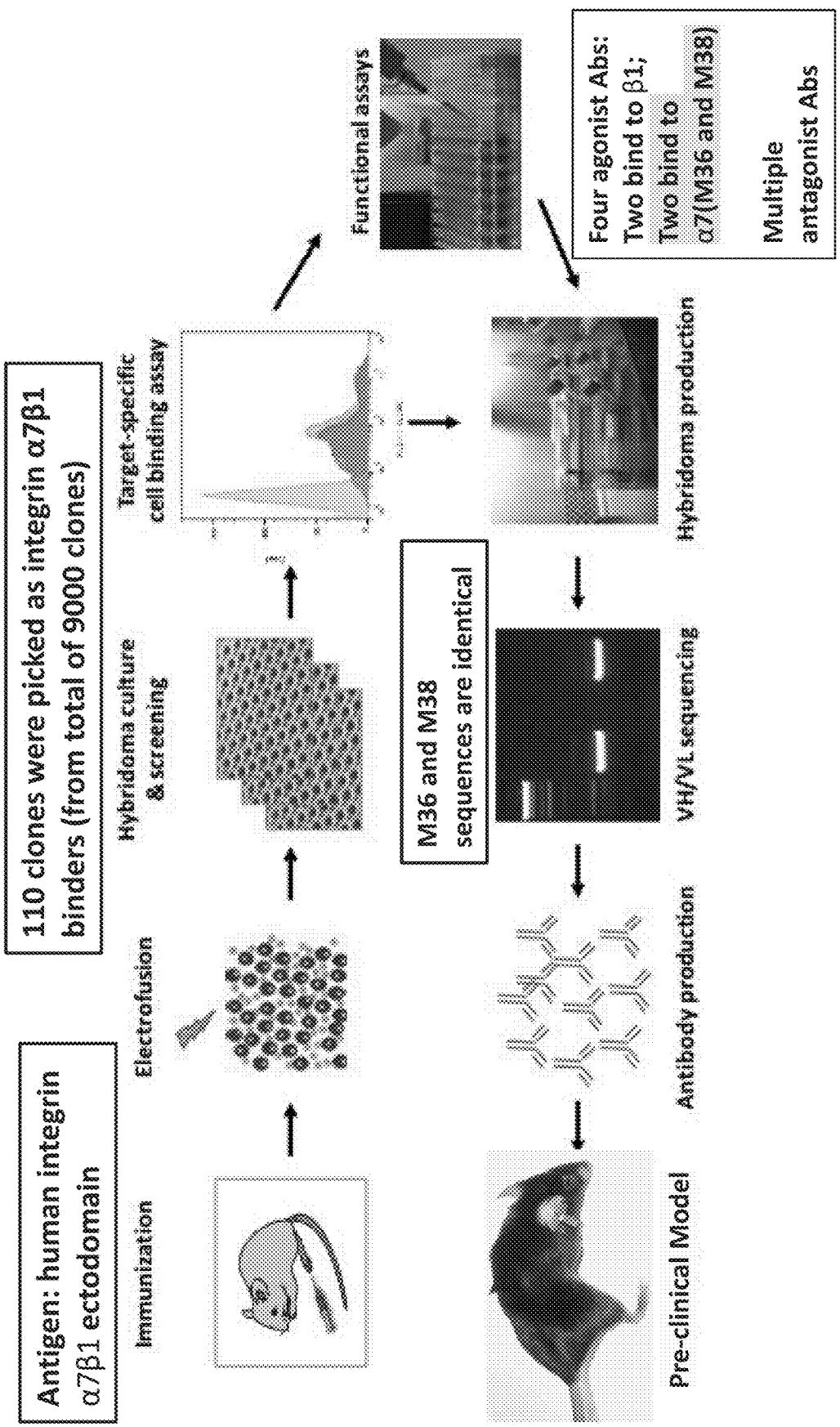
FIG. 9 is a schematic of the process by which monoclonal antibodies binding to integrin α7β1 protein were generated and characterized.
Figure 10A:
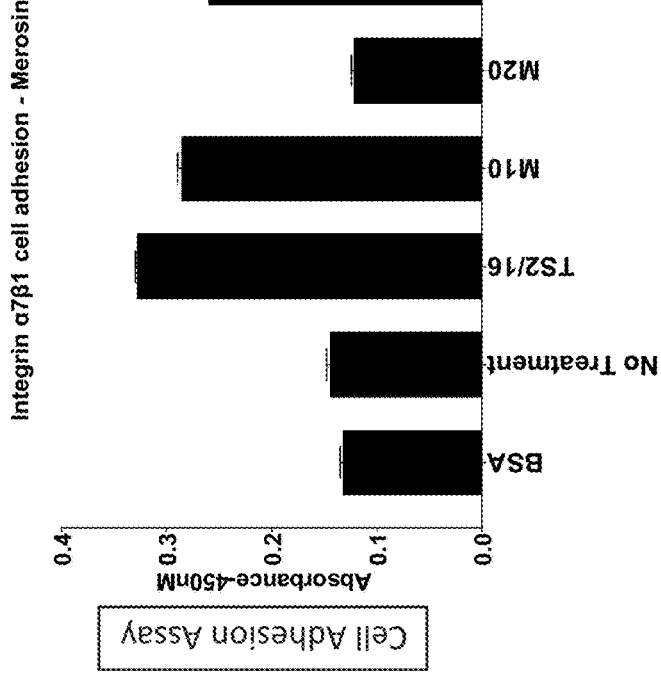
FIG. 10A is a graph showing the results of a solid phase binding assay of the activity of two activating antibodies (M10, M25) and one blocking antibody (M20) to α7β1 integrin.
Figure 10B:
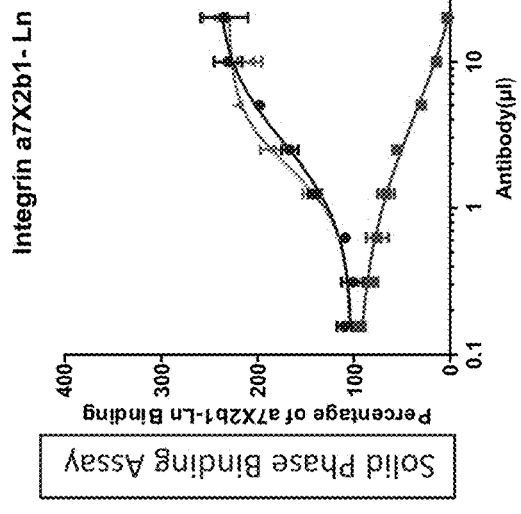
FIG. 10B is a graph showing the results of a cell adhesion assay of the activity of two activating antibodies (M10, M25) and one blocking antibody (M20) to α7β1 integrin.
Figure 10C:
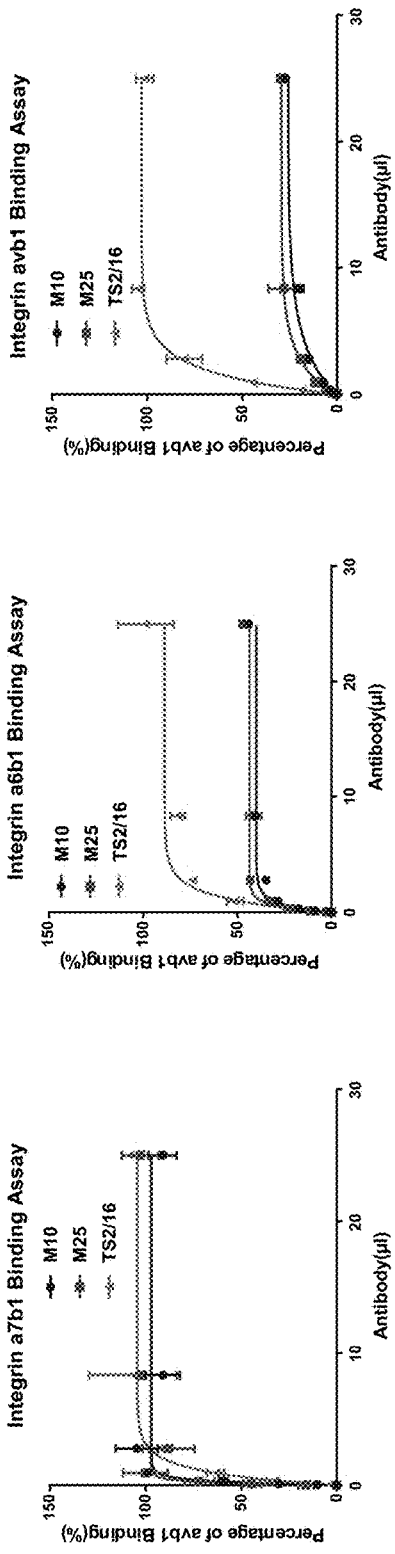
FIG. 10C is a series of graphs showing the results of direct ELISAs analyzing the binding of M10 and M25 antibodies and a β1 agonist antibody (TS2/16) to β1-containing integrins.

Monoclonal antibodies were generated by immunizing mice with human integrin α7β1 protein ectodomain. A general schematic of the process is shown in FIG. 9. Hybridomas were produced by standard techniques. From a total of 9,000 clones, 110 clones were selected as integrin α7β1 binders. Multiple antagonist (blocking) and four agonist (activating) antibodies were identified in functional biochemistry and cellular assays. These antibodies were characterized as either activating or blocking in a solid phase binding assay and a cell adhesion assay. The activating antibodies are referred to as M10, M25, M36 and M38. FIG. 10A shows an example of results from a solid phase binding assay, and FIG. 10B shows an example of results from a cell adhesion assay performed with two activating antibodies (M10, M25) and one blocking antibody (M20). The activating antibodies were further characterized (for example, by ELISA or flow cytometry) to determine whether the activation takes place through the α7 protein or the β1 protein. M10 and M25 were found to bind the β1 protein as the two antibodies stimulated binding not only to α7β1 but also to α6β1 integrin and to αvβ1 integrin (FIG. 10C).

Figure 11A:
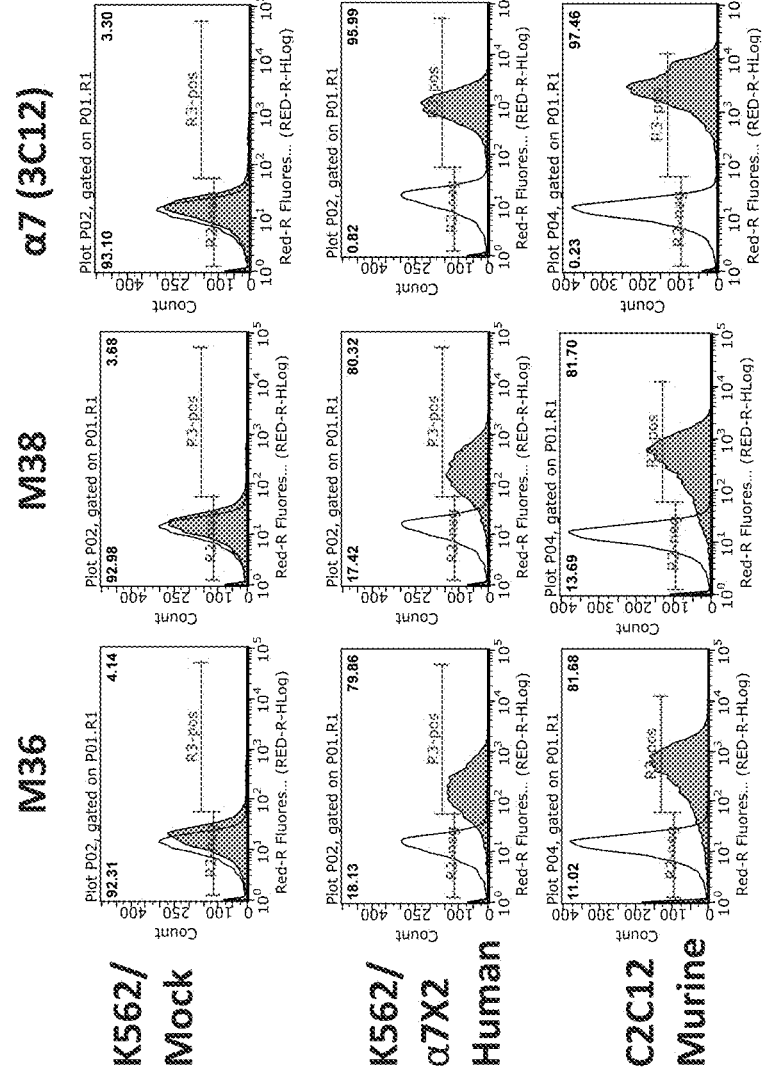
FIG. 11A is a series of graphs showing that antibodies M36 and M38 bind to cell surfaces expressing α7β1 integrins. K562/Mock (transfected with control empty vector), K562 α7X2 (transfected with plasmid encoding integrin α7X2 cDNA) and C2C12 cells were tested for binding of M36, M38 and α7 (3C12). 3C12 is a positive control antibody for integrin α7.
Figure 11B:
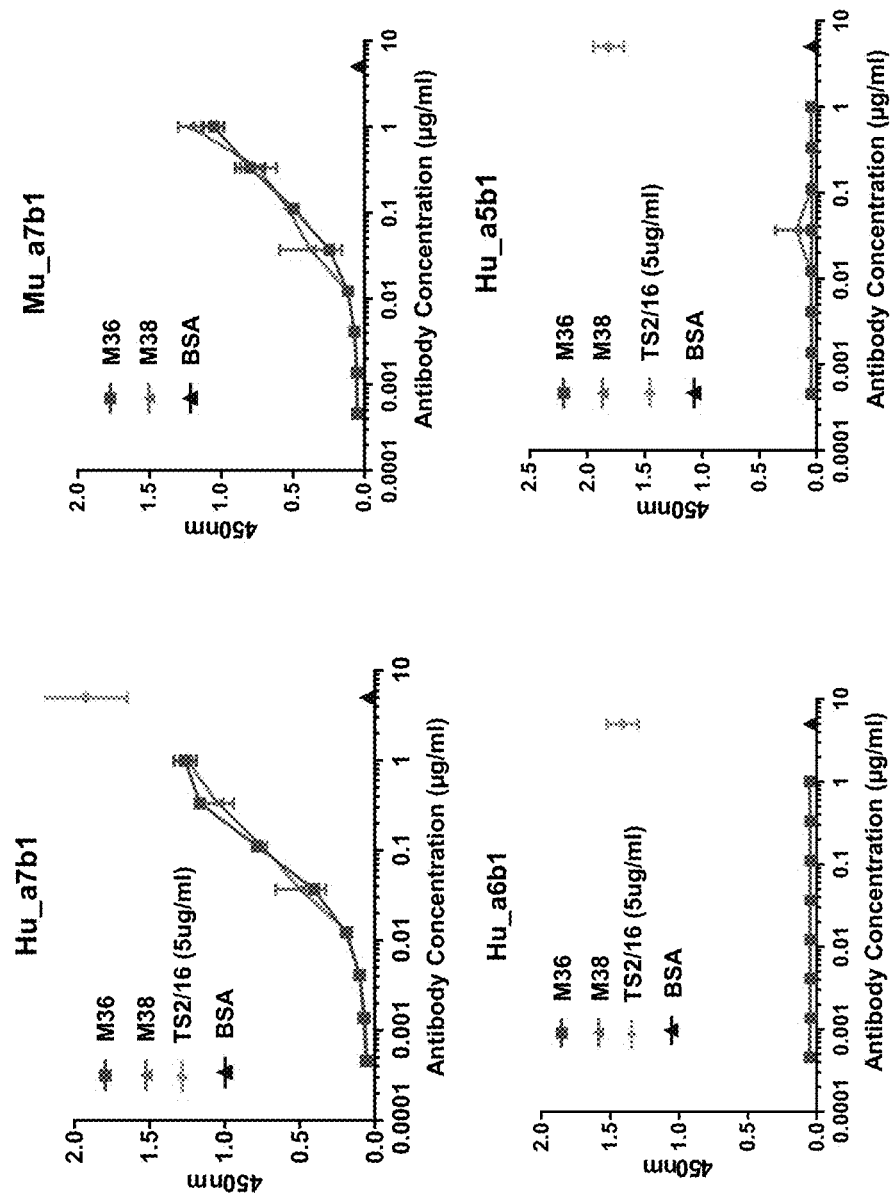
FIG. 11B is a series of graphs showing that antibodies M36 and M38 selectively bind to human and murine α7β1 integrins (Hu_a7b1 and Mu_a7b1), as opposed to human α6β1 (Hu_a6b1) or α5β1 (Hu_a5b1) integrins.

Antibodies M36 and M38 were found to bind to cell surfaces expressing α7β1 (both human (K562/α7X2) and murine (C2C12) integrins). See FIG. 11A. Binding of M36 and M38 to human and murine α7β1 integrin was dose-dependent and not mediated through the β1 subunit of the heterodimer, as M36 and M38 did not bind to α6β1 or α5β1 integrin (FIG. 11B).

Figure 12A:
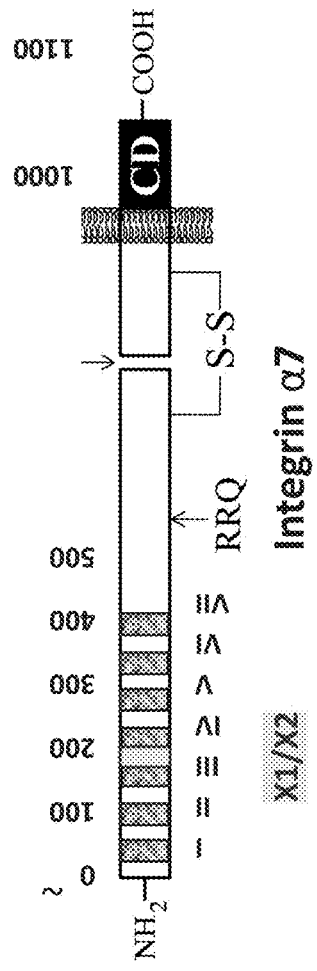
FIG. 12A is a diagram of the integrin α7 protein structure and its domains. This figure also depicts the variable region sequences X1 (SEQ ID NO: 1) and X2 (SEQ ID NO: 10) found in the extracellular domain of integrin α7 protein.
Figure 12B:
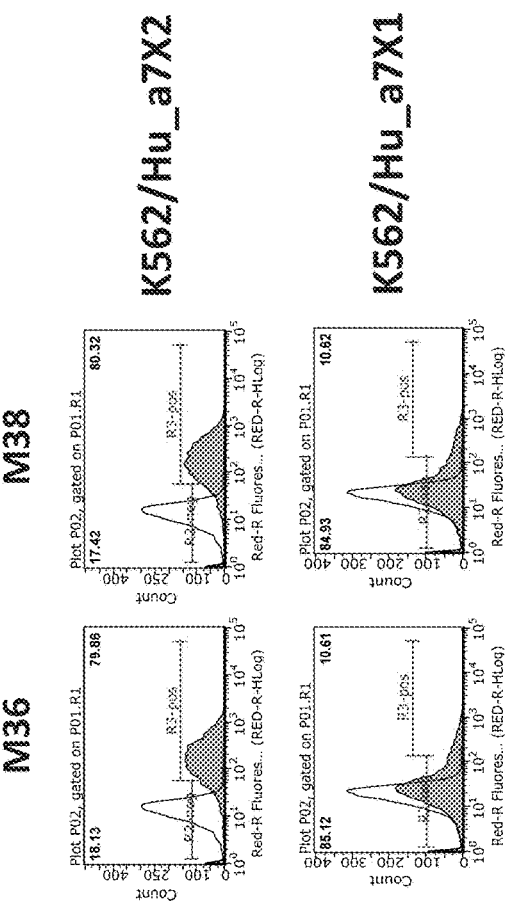
FIG. 12B is a series of graphs showing that antibodies M36 and M38 preferentially bind to cell surfaces expressing the X2 form of α7β1 integrin. K562 cell lines stably transfected with human integrin α7X1 or α7X2 cDNA are named as K562/Hu_a7X1 or K562/Hu_a7X2.

Integrin α7 protein can have two different extracellular sequences (designated "X1" and "X2") due to post-transcriptional modification. The variable region sequence (X1 or X2) is located between the III and IV homology repeat domains near the putative ligand-binding site (FIG. 12A). There are 40 amino acids in the X2 variable region sequence. Antibodies M36 and M38 preferentially bind to cell surfaces expressing the α7β1 X2 form (FIG. 12B), which is preferentially expressed in adult skeletal cells. Due to the specificity of the binding on the α7X2 isoform, but not the α7X1 isoform, it is concluded that M36 and M38 are specifically binding the α7X2 subunit of the α7β1 heterodimer integrin (FIG. 12B).

Figure 13B:
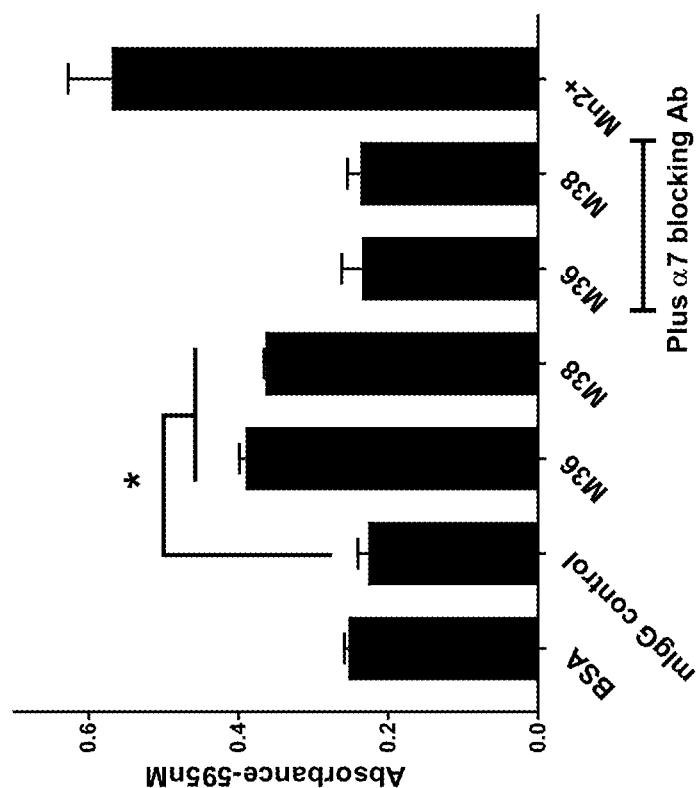
FIG. 13B is a graph showing that antibodies M36 and M38 enhance the adhesion of mouse myotubes in which dystrophin has been knocked down (KD) to laminin.
Figure 13A:
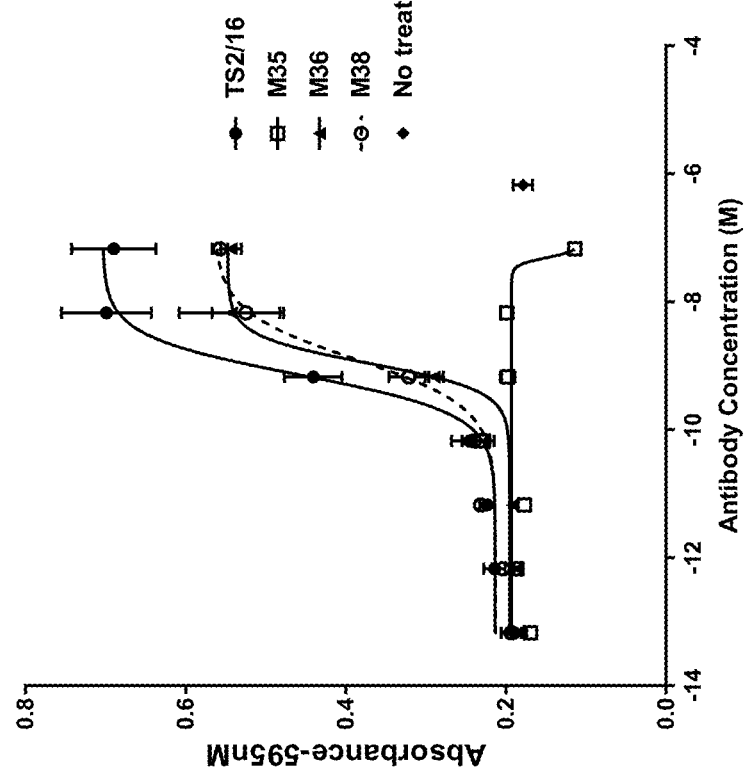
FIG. 13A is a graph showing that antibodies M36 and M38 enhance integrin α7β1 (K562/a7X2) cell adhesion to human laminin 211 (LN211). TS2/16 is a β1 agonist antibody. M35 is a control antibody having no effect on adhesion to laminin.

Antibodies M36 and M38 were found to enhance integrin α7β1-mediated adhesion of K562/α7x2β1 cells to laminin (LN211). Antibodies M36 and M38 enhanced integrin α7β1 cell adhesion to human laminin 211 (EC50s: 1.09 nM and 1.27 nM). See FIG. 13A. Control antibody M35 had no effect. Antibodies M36 and M38 enhanced mouse myotube, in which dystrophin has been knockdown, adhesion to laminin. See FIG. 13B. This effect could be reversed by α7 blocking antibody.

Figure 14:
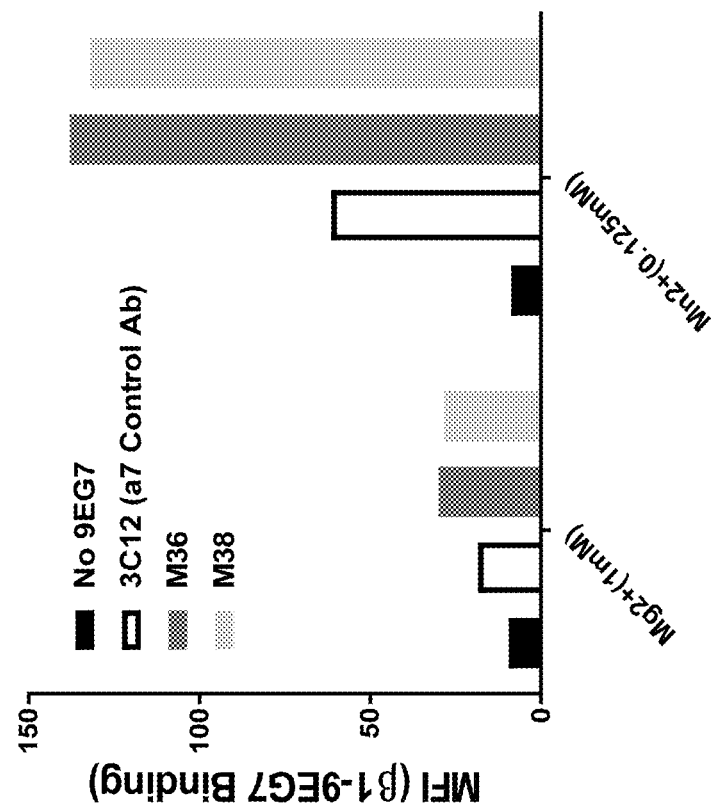
FIG. 14 is a graph showing that antibodies M36 and M38 convert integrin α7β1 to an active conformation. Monoclonal antibody 9EG7 detects β1 integrin activation. Different cations were used to adjust integrin conformations before the antibody treatment (less active (Mg2+1 mM) and active (Mn2+0.125 mM)).

Antibodies M36 and M38 were found to activate integrin α7β1 through a conformational change. Monoclonal antibody 9EG7 selectively binds to activated β1 integrins (Bazzoni et al., J Biol Chem. 1995; 270 (43): 25570-7). Mn2+ mediates β1 integrin activation and this can be detected by 9EG7 (white bar, FIG. 14). As shown in FIG. 14, antibodies M36 and M38 enhance the binding of 9EG7 (dark and light grey bars) over the α7 control (con functional) antibody (white bar), which indicates change of integrin α7β1 into a more activated conformation.

The M36 and M38 antibody heavy and light chain variable regions were sequenced and were found to be identical. These sequences are provided in Table 2.

TABLE 2

Amino acid sequences of antibody M36 and antibody M38

| | | |
|---|---|---|
| HCDR1 | GYNFTKYW | SEQ ID NO: 2 |
| HCDR2 | IYPGSSTS | SEQ ID NO: 3 |
| HCDR3 | VRGDD | SEQ ID NO: 4 |
| LCDR1 | ESVDNYGISF | SEQ ID NO: 5 |
| LCDR2 | AAS | SEQ ID NO: 6 |
| LCDR3 | HQSKEVPYT | SEQ ID NO: 7 |
| VH | QVQLQQPGAELVKPGASVKL SCKASGYNFTKYWINWVKQR PGQGLEWIGIIYPGSSTSNY NEKFKTKATLTVEISSTTAY MQLSSLTSDDSAVYYCVRGD DWGQGTTLTVSS | SEQ ID NO: 8 |
| VL | DIVLTQSPASLAVSLGQRAT ISCRASESVDNYGISFMNWF | SEQ ID NO: 9 |

TABLE 2-continued

Amino acid sequences of antibody M36 and antibody M38

```
QQKPGQPPKLLIYAASDLGS
GVPARFTGSGSGTDFSLNIH
PMEEDDSAMYFCHQSKEVPY
TFGGGTKLEIK
```

Example 3: Generation and Characterization of Humanized α7β1 Agonist Antibodies

The sequence of the M36/M38 antibody was subsequently humanized. The antibody sequence was analyzed for three dimensional structure and was built by homology modeling. Key positions supporting the CDR loop structure and VH-VL interface were identified. Multiple humanized variants were designed for both heavy and light chains. The humanness of humanized variants were assessed by the T20 humanness score described in Gao et al., (2013) *BMC Biotechnology*, 13:55. The humanized antibodies as well as a chimeric version (rodent variable regions, human constant regions) were expressed at the 10 mL scale in CHO cells (TunaCHO™ Process) and purified. Binding affinity of each antibody produced was tested by flow cytometry and ELISA.

A humanized antibody referred to as "VL3VHK20TFT" was isolated. The amino acid and nucleotide sequences of various regions of VL3VHK20TFT are provided in Table 3. VL3VHK20TFT belongs to the IgG4 isotype and S228P subclass. The light chain isotype of VL3VHK20TFT is human kappa.

TABLE 3

Amino acid and nucleotide sequences of antibody VL3VHK20TFT

| | | |
|---|---|---|
| HCDR1 | GYTFTKYW | SEQ ID NO: 14 |
| HCDR2 | IYPGSSTS | SEQ ID NO: 3 |
| HCDR3 | VKNDN | SEQ ID NO: 15 |
| LCDR1 | ESVDNYGISF | SEQ ID NO: 5 |
| LCDR2 | AAS | SEQ ID NO: 6 |
| LCDR3 | HQSKEVPYT | SEQ ID NO: 7 |
| VH (CDR sequences are underlined) | QVQLVQSGAEVKKPGASVKVSCKASGYTFTKYWINWVRQ APGQGLEWMGIIYPGSSTSNYNEKFKTRVTMTVDTSTST AYMELSSLRSEDTAVYYCVKNDNWGQGTLVTVSS | SEQ ID NO: 16 |
| VL (CDR sequences are underlined) | DIQMTQSPSSLSASVGDRVTITCRASESVDNYGISFMNW FQQKPGKAPKLLIYAASDLGSGVPSRFSGSGSGTDFTLT ISSLQPEDFATYYCHQSKEVPYTFGQGTKLEIK | SEQ ID NO: 17 |
| Heavy Chain amino acid sequence (the S228P mutation is in bold font) | QVQLVQSGAEVKKPGASVKVSCKASGYTFTKYWINWVRQ APGQGLEWMGIIYPGSSTSNYNEKFKTRVTMTVDTSTST AYMELSSLRSEDTAVYYCVKNDNWGQGTLVTVSSASTKG PSVFPLAPCSRSTSESTAALGCLVKDYFPEPVTVSWNSG ALTSGVHTFPAVLQSSGLYSLSSVVTVPSSSLGTKTYTC NVDHKPSNTKVDKRVESKYGPPCPPCPAPEFLGGPSVFL FPPKPKDTLMISRTPEVTCVVVDVSQEDPEVQFNWYVDG VEVHNAKTKPREEQFNSTYRVVSVLTVLHQDWLNGKEYK CKVSNKGLPSSIEKTISKAKGQPREPQVYTLPPSQEEMT KNQVSLTCLVKGFYPSDIAVEWESNGQPENNYKTTPPVL DSDGSFFLYSRLTVDKSRWQEGNVFSCSVMHEALHNHYT QKSLSLSLG | SEQ ID NO: 18 |
| Light Chain amino acid sequence | DIQMTQSPSSLSASVGDRVTITCRASESVDNYGISFMNW FQQKPGKAPKLLIYAASDLGSGVPSRFSGSGSGTDFTLT ISSLQP EDFATYYCHQSKEVPYTFGQGTKLEIKRTVAAPSVFIF PPSDEQLKSGTASVVCLLNNFYPREAKVQWKVDNALQS GNSQESVTEQDSKDSTYSLSSTLTLSKADYEKHKVYAC EVTHQGLSSPVTKSFNRGEC | SEQ ID NO: 19 |
| Heavy Chain nucleotide Sequence | ATGGACCCCAAGGGCAGCCTGAGCTGGAGAATCCTGCT GTTCCTGAGCCTGGCCTTCGAGCTGAGCTACGGCCAGG TGCAGCTGGTGCAGAGCGGTGCGGAAGTGAAGAAGCCC GGTGCCAGCGTGAAGGTGAGCTGCAAGGCCAGCGGCTA CACCTTCACCAAGTACTGGATCAACTGGGTGAGGCAGG CACCCGGCCAAGGCCTGGAGTGGATGGGCATCATCTAC CCCGGCAGCAGCACCAGCAATTACAACGAGAAGTTCAA GACCCGAGTAACCATGACCGTGGACACCTCCACCAGCA CCGCCTACATGGAGCTGAGCAGCCTGAGGAGCGAGGAC ACCGCAGTGTACTACTGCGTGAAGAACGACAACTGGGG CCAGGGCACCCTGGTGACCGTCAGCTCTGCTAGCACCA AGGGCCCCAGCGTGTTTCCTCTCGCTCCCTGCAGCCGG AGCACATCCGAGAGCACCGCTGCTCTGGGCTGTCTCGT | SEQ ID NO: 20 |

TABLE 3-continued

Amino acid and nucleotide sequences of antibody VL3VHK20TFT

| | | |
|---|---|---|
| | GAAGGACTACTTCCCTGAACCCGTCACCGTCAGCTGGA<br>ATAGCGGCGCCCTGACATCCGGCGTCCACACATTCCCC<br>GCTGTCCTGCAGAGCAGCGGCCTGTACAGCCTGAGCTC<br>CGTGGTCACCGTGCCTAGCAGCAGCCTGGGAACAAAGA<br>CCTACACCTGCAACGTGGACCATAAGCCCTCCAACACC<br>AACtGTGCtACAAGCGGGTGGAATCCAAGTATGGACCC<br>CCCTGTCCTCCTTGCCCTGCTCCTGAATTTCTCGGAGG<br>CCCCTCCGTCTTCCTGTTTCCCCCCAAGCCCAAGGACA<br>CCCTGATGATCTCCCGGACACCCGAAGTCACCTGCGTC<br>GTGGTGGATGTCAGCCAGGAAGATCCCGAGGTGCAGTT<br>CAACTGGTACGTGGACGGAGTGGAGGTGCATAACGCCA<br>AAACCAAGCCCAGGGAAGAGCAGTTCAACAGCACCTAT<br>CGGGTCGTGTCCGTGCTCACCGTCCTGCATCAGGATTG<br>GCTCAACGGCAAGGAGTACAAGTGCAAGGTGTCCAACA<br>AGGGCCTGCCCTCCTCCATCGAGAAGACCATCTCCAAG<br>GCTAAGGGCCAACCTCGGGAGCCCCAAGTGTATACCCT<br>CCCTCCCAGCCAGGAGGAGATGACCAAGAATCAAGTGA<br>GCCTGACCTGCCTCGTGAAGGGATTTTACCCCTCCGAC<br>ATCGCTGTGGAATGGGAAAGCAATGGCCAACCTGAGAA<br>CAACTACAAGACCACACCCCCGTGCTGGACTCCGATG<br>GCTCCTTCTTCCTGTACAGCAGGCTGACCGTGGACAAA<br>TCCCGGTGGCAAGAGGGAAACGTGTTCAGCTGCTCCGT<br>GATGCACGAGGCTCTCCACAACCACTACACCCAGAAGA<br>GCCTCTCCCTGAGCCTCGGCTAG | |
| Light<br>Chain<br>nucleotide<br>sequence | ATGGAGACCGACACCCTGCTGCTCTGGGTGCTGCTGCT<br>CTGGGTGCCCGGCTCCACCGGAGACATCCAGATGACCC<br>AGAGCCCCAGCAGCCTGTCCGCTAGCGTAGGCGACAGG<br>GTCACCATCACCTGTAGGGCCAGTGAGAGCGTGGACAA<br>CTACGGCATCAGCTTTATGAACTGGTTCCAGCAGAAGC<br>CCGGCAAGGCCCCCAAGCTGCTGATTTACGCCGCCAGCG<br>ACCTGGGCAGCGGCGTGCCCAGTAGGTTCAGCGGCTCCG<br>GTAGCGGCACCGACTTCACCCTGACTATCAGCTCTCTGC<br>AGCCCGAGGACTTCGCCACCTACTACTGCCACCAGAGCA<br>AGGAGGTCCCCTATACCTTCGGCCAAGGCACCAAGTTGG<br>AGATCAAGCGGACCGTGGCCGCCCCCAGCGTGTTCATCT<br>TCCCTCCCAGCGACGAGCAGCTGAAGTCTGGCACCGCCA<br>GCGTGGTGTGCCTGCTGAACAACTTCTACCCCCGCGAGG<br>CCAAGGTGCAGTGGAAGGTGGACAACGCCCTGCAGAGCG<br>GCAACAGCCAGGAGAGCGTGACCGAGCAGGACTCCAAGG<br>ACAGCACCTACAGCCTGAGCAGCACCCTGACCCTGAGCA<br>AGGCCGACTACGAGAAGCACAAGGTGTACGCCTGCGAGG<br>TGACCCACCAGGGACTGTCTAGCCCCGTGACCAAGAGCT<br>TCAACCGGGGCGAGTGCTAA | SEQ ID NO: 21 |

*Note that the following sequences are identical: SEQ ID NO: 15, SEQ ID NO: 66, SEQ ID NO: 68.

Conditions for binding and screening of monoclonal antibodies and Fabs using high-throughput flow cytometry were optimized using wild-type target protein cloned into a proprietary vector and expressed in HEK-293T cells. The target protein is human integrin alpha-7 (ITGA7; UniProt ID Q13683; SEQ ID NO: 24). The binding of the VL3VHK20TFT monoclonal antibody and the VL3VHK20TFT Fab to HEK-293T cells co-transfected (1:1) with integrin beta-1 precursor (ITGB1) and integrin subunit alpha 7 (ITGA7) or with vector alone (negative control) was evaluated by high-throughput flow cytometry. The antibodies 3C12, 6A11, A1-1a M20, and A1-1a M24 were used as positive controls for ITGA7 binding. These antibodies and the parameters for high-throughput flow cytometry are provided in Table 4.

TABLE 4

Experimental parameters optimized for high-throughput flow cytometry

| Experimental Parameter | Test MAb | Control MAb | Control MAb | Control MAb | Control MAb |
|---|---|---|---|---|---|
| Cell Type | HEK-293T | HEK-293T | HEK-293T | HEK-293T | HEK-293T |
| Fixative | None | None | None | None | None |
| Blocking Buffer | 10% Goat Serum | 10% Goat Serum | 10% Goat Serum | 10% Goat Serum | 10% Goat Serum |
| Primary Antibody | | | | | |
| Name | VL3VHK20TFT | 3C12 MAb (MBL) | 6A11 MAb (MBL) | A1-1 aM20 MAb | A1-1aM24 MAb |
| Target | MAb | ITGA7 | ITGA7 | ITGA7 | ITGA7 |
| Optimal Conc. | ITGA7 | 0.5 µg/ml | 2.0 µg/ml | 0.13 µg/ml | 0.5 µg/ml |
| Incubation (25° C.) | 0.5 µg/ml<br>60 min | 60 min | 60 min | 60 min | 60 min |

TABLE 4-continued

Experimental parameters optimized for high-throughput flow cytometry

| Experimental Parameter | Test MAb | Control MAb | Control MAb | Control MAb | Control MAb |
|---|---|---|---|---|---|
| Secondary Antibody | | | | | |
| Target | Human IgG | Mouse IgG | Mouse IgG | Mouse IgG | Mouse IgG |
| Optimal Conc. | 1:400 (3.75 µg/ml) | 1:400 (3.75 µg/ml) | 1:400 (3.75 µg/ml) | 1:400 (3.75 µg/ml) | 1:400 (3.75 µg/ml) |
| Incubation (25° C.) | 30 min | 30 min | 30 min | 30 min | 30 min |
| Manufacturer | Jackson ImmunoResearch | Jackson ImmunoResearch | Jackson ImmunoResearch | Jackson ImmunoResearch | Jackson ImmunoResearch |
| Cat # | 109-545-003 | 115-545-003 | 115-545-003 | 115-545-003 | 115-545-003 |
| Antibody ID | AlexaFluor ® 488 AffiniPure Goat Anti-Human IgG (H + L) | AlexaFluor ® 488 AffiniPure Goat Anti-Mouse IgG (H +L) | AlexaFluor ® 488 AffiniPure Goat Anti-Mouse IgG (H + L) | AlexaFluor ® 488 AffiniPure Goat Anti-Mouse IgG (H + L) | AlexaFluor ® 488 AffiniPure Goat Anti-Mouse IgG (H + L) |
| Wash Buffer | PBS ($Ca^{2+}$, $Mg^{2+}$ free) | PBS ($Ca^{2+}$, $Mg^{2+}$ free) | PBS ($Ca^{2+}$, $Mg^{2+}$ free) | PBS ($Ca^{2+}$, $Mg^{2+}$ free) | PBS ($Ca^{2+}$, $Mg^{2+}$ free) |
| Signal:Background | 18:1 | 16:1 | 16:1 | 17:1 | 16:1 |

The parameters used for high-throughput flow cytometry with VL3VHK20TFT Fab are provided in Table 5.

TABLE 5

| Experimental parameters optimized for high-throughput flow cytometry. | |
|---|---|
| Experimental Parameter | Test Fab |
| Cell Type | HEK-293T |
| Fixative | None |
| Blocking Buffer | 10% Goat Serum |
| Primary Antibody | |
| Name | VL3VHK20TFT Fab |
| Target | ITGA7 |
| Optimal Conc. | 2.0 µg/ml |
| Incubation (25° C.) | 60 min |
| Secondary Antibody | |
| Target | Human F(ab')2 |
| Optimal Conc. | 1:200 (7.50 µg/ml) |
| Incubation (25° C.) | 30 min |
| Manufacturer | Jackson ImmunoResearch |
| Cat # | 109-546-006 |
| Antibody ID | AlexaFluor ® 488 AffiniPure Goat Anti- Human IgG F(ab')2 Fragment |
| Wash Buffer | PBS ($Ca^{2+}$, $Mg^{2+}$ free) |
| Signal:Background | 12:1 |

Figure 15:
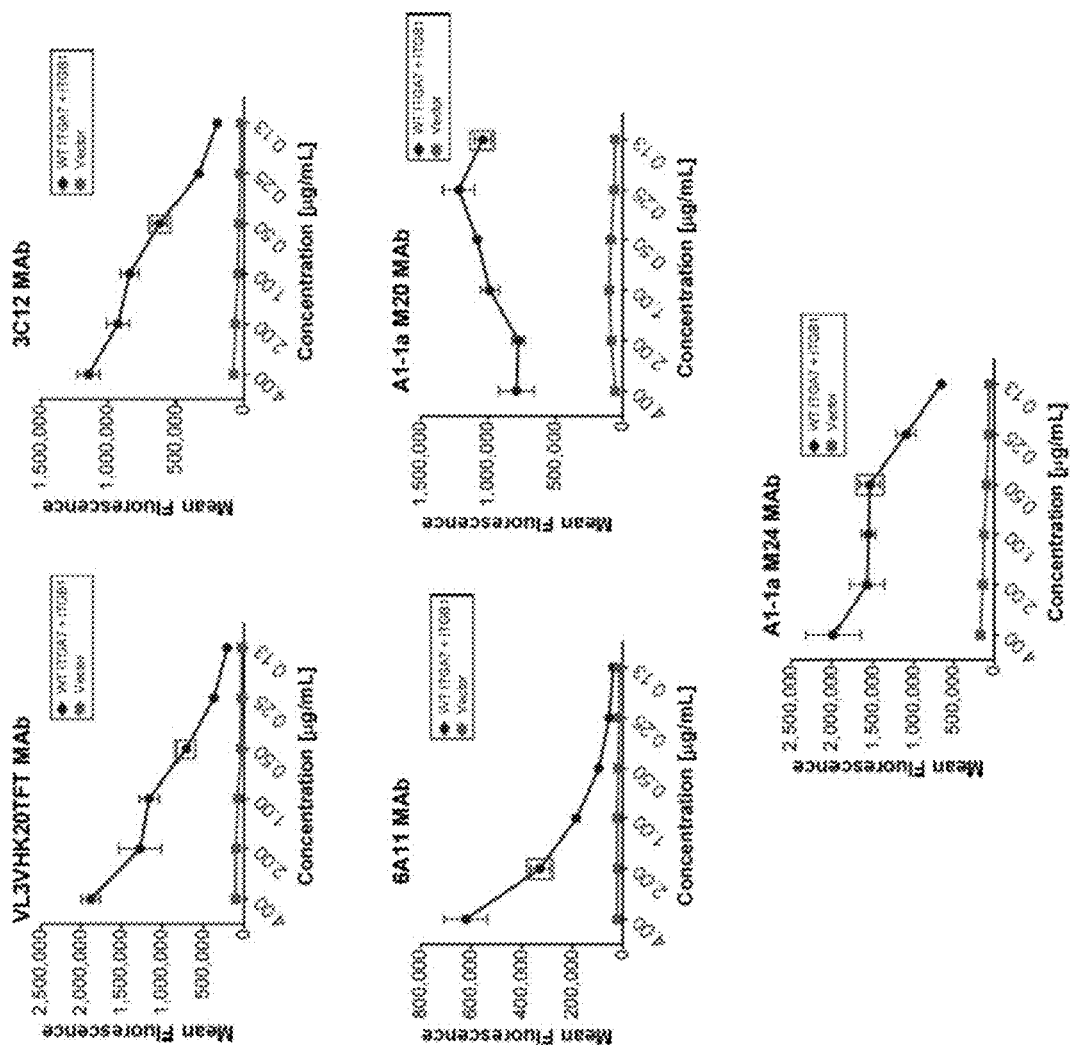
FIG. 15 is a series of graphs showing that the VL3VHK20TFT monoclonal antibody binds to cells co-transfected with integrin subunit alpha 7 (ITGA7) and integrin beta-1 (ITGB1). 3C12, 6A11, A1-1a M20, and A1-1a M24 are positive control antibodies for binding to IGTA7. These antibodies are described in Table 4. The optimal screening concentration for each monoclonal antibody is outlined by a box.
Figure 16:
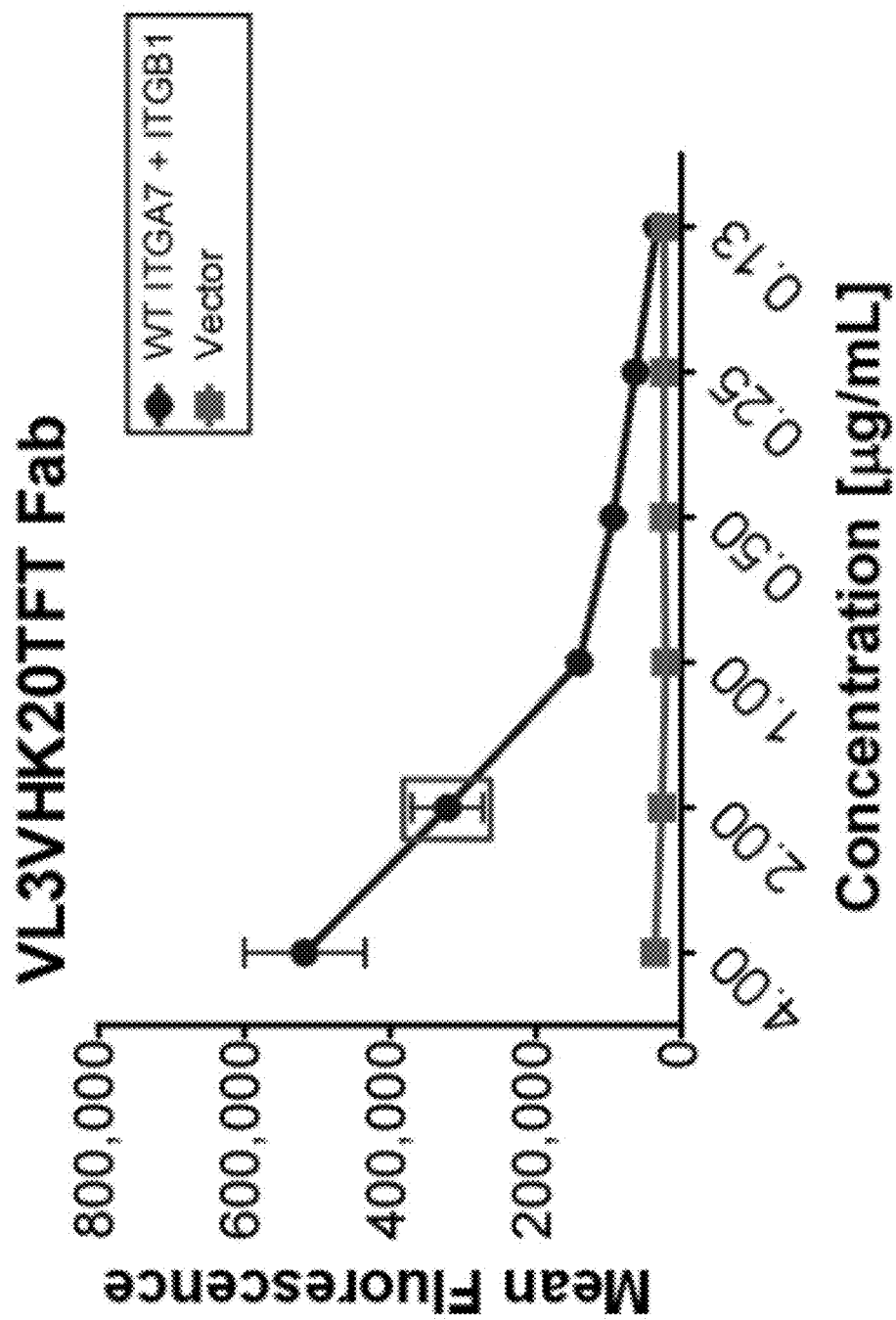
FIG. 16 is a graph showing that the VL3VHK20TFT Fab binds to cells co-transfected with integrin subunit alpha 7 (ITGA7) and integrin beta-1 (ITGB1). The optimal screening concentration for the Fab is outlined by a box.

As FIG. 15 and FIG. 16 show, VL3VHK20TFT mAb (FIG. 15) and VL3VHK20TFT Fab (FIG. 16) bind selectively to cells containing the target protein ITGA7 and do not bind to cells that do not contain the target (vector). Each point in FIG. 15 and FIG. 16 represents the mean of four replicates. The optimal screening concentration for each antibody or Fab (outlined in a box) was determined based on the raw signal values and signal-to-background calculations.

In order to map the epitope of VL3VHK20TFT, an alanine-scan library of the target protein (ITGA7; SEQ ID NO: 24) was constructed. Shotgun mutagenesis epitope mapping was performed using the general procedure described in Davidson and Doranz, 2014, *Immunology* 143, 13-20. Briefly, a mutation library of the target protein was created by high-throughput, site-directed mutagenesis. Each residue was individually mutated to alanine, with alanine codons mutated to serine. The mutant library was arrayed in 384-well microplates and transiently transfected into HEK-293T cells. Following transfection, cells were incubated with the indicated antibodies (VL3VHK20TFT Fab or 6A11 monoclonal antibody (mAb)) at concentrations pre-determined using an independent immunofluorescence titration curve on wild type protein. The antibodies were detected using an Alexa Fluor® 488-conjugated secondary antibody, which is a green fluorophore with observable excitation and emission spectra values, and mean cellular fluorescence was determined using Intellicyt® (now Essen BioScience, Inc., a Sartorius AG company) iQue® flow cytometry platform, which is a specialized microvolume-sampling device for characterizing large numbers of cells or particles. Mutated residues were identified as being critical to the VL3VHK20TFT Fab epitope if they did not support the reactivity of the VL3VHK20TFT Fab but did support the reactivity of the reference 6A11 mAb. This counterscreen strategy facilitates the exclusion of mutants that are locally misfolded or that have an expression defect.

Library screens of very-high-affinity MAbs sometimes fail to yield critical residues for antibody binding. Conversion of a high-affinity MAb to a Fab usually weakens binding sufficiently to allow identification of critical residues for binding. For cases where Fab screens under standard conditions are still insufficient to identify critical residues for binding, high stringency conditions are implemented. These conditions include combinations of increased pH, increased salinity, increased temperature, and/or increased wash time. Antibodies that required high stringency conditions are denoted "HS".

Figure 17:
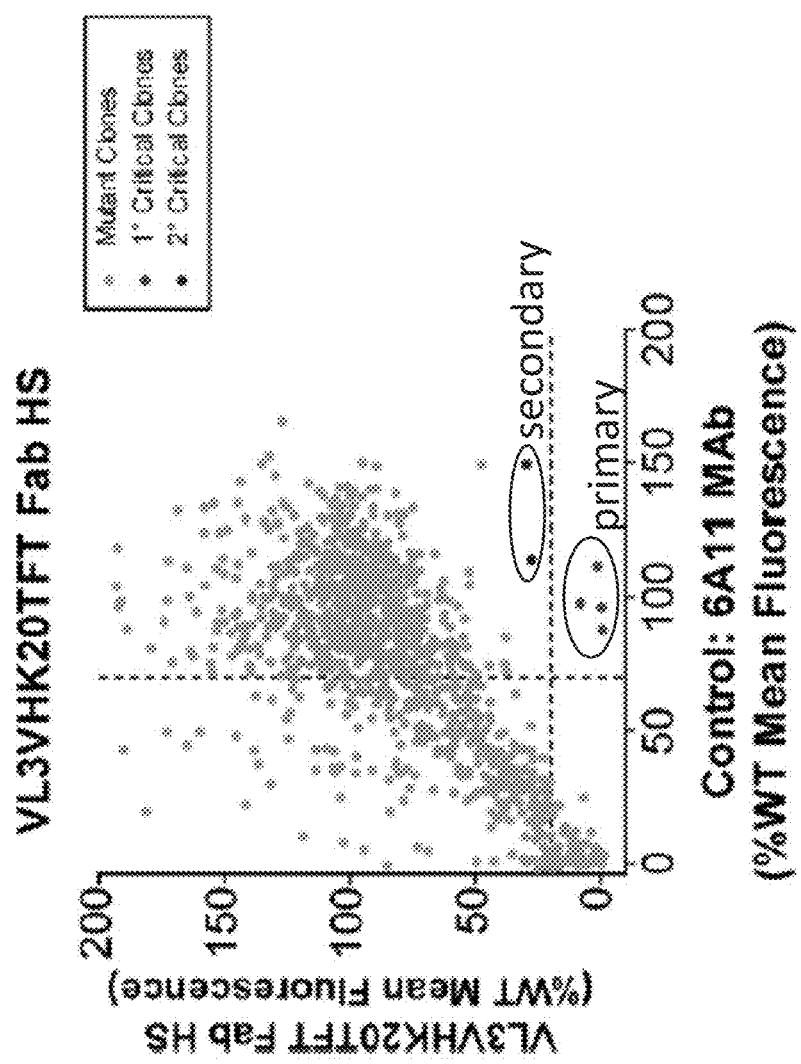
FIG. 17 is a graph showing binding of the VL3VHK20TFT Fab to a library of cells co-transfected with an alanine scanning library of ITGA7 mutants.
Figure 18:
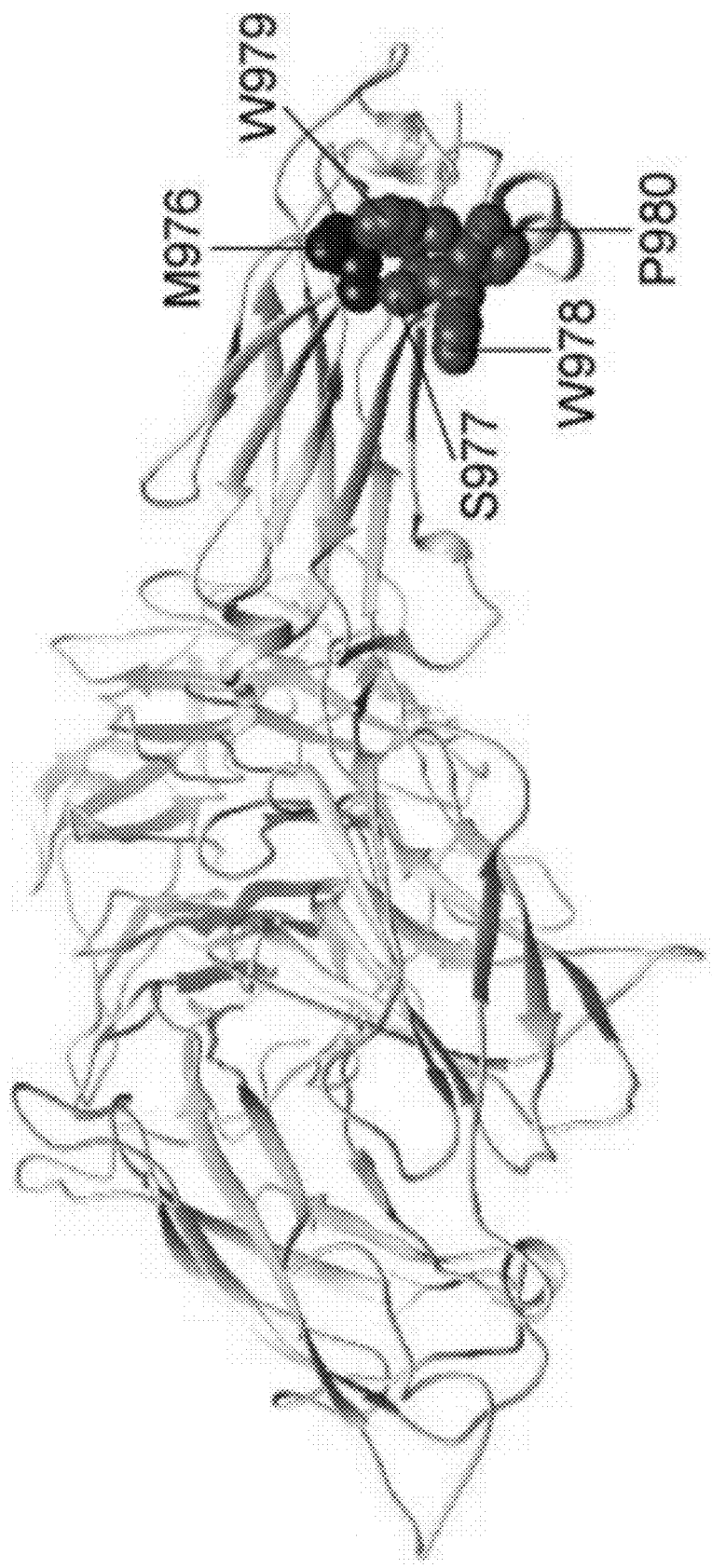
FIG. 18 is a crystal structure model showing the critical residues for binding of the VL3VHK20TFT Fab to integrin subunit alpha 7. Critical residues are shown as red spheres. Secondary residues are shown as blue spheres.
Figure 19:
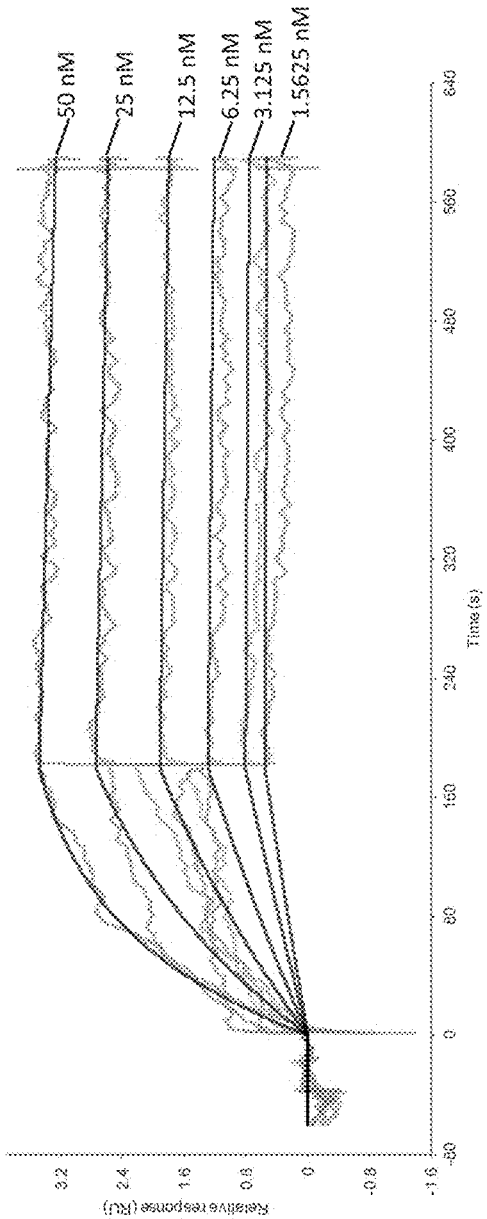
FIG. 19 is a graph showing results from Example 4 at various concentrations for VL3VHK20 TFT; 0.25 µg/mL Human Integrin α7β1; 1:1 binding.
Figure 20:
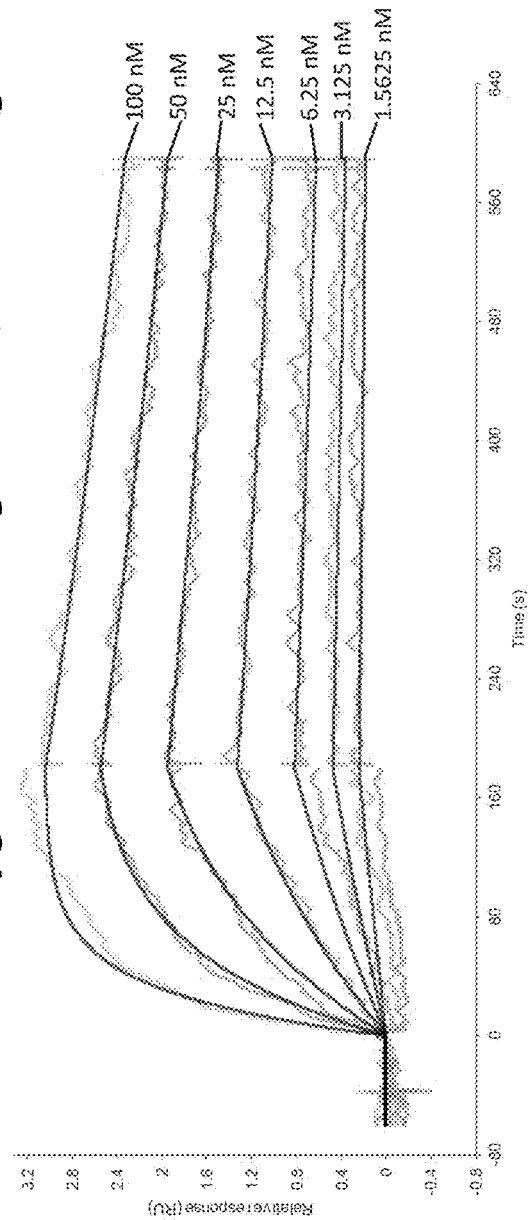
FIG. 20 is a graph showing results from Example 4 at various concentrations for VLVH; 0.25 µg/mL Human Integrin α7β1; 1:1 binding.
Figure 21A:
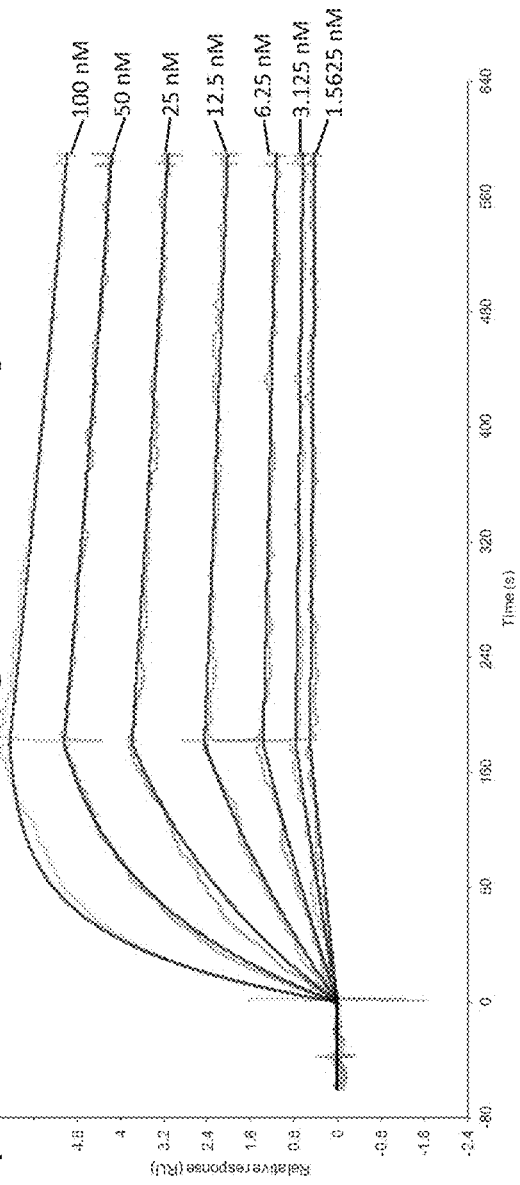
FIG. 21A is a graph showing results from Example 4 at various concentrations for VL3VHK20 TFT; 0.25 µg/mL Mouse Integrin α7β1; 1:1 binding.
Figure 21B:
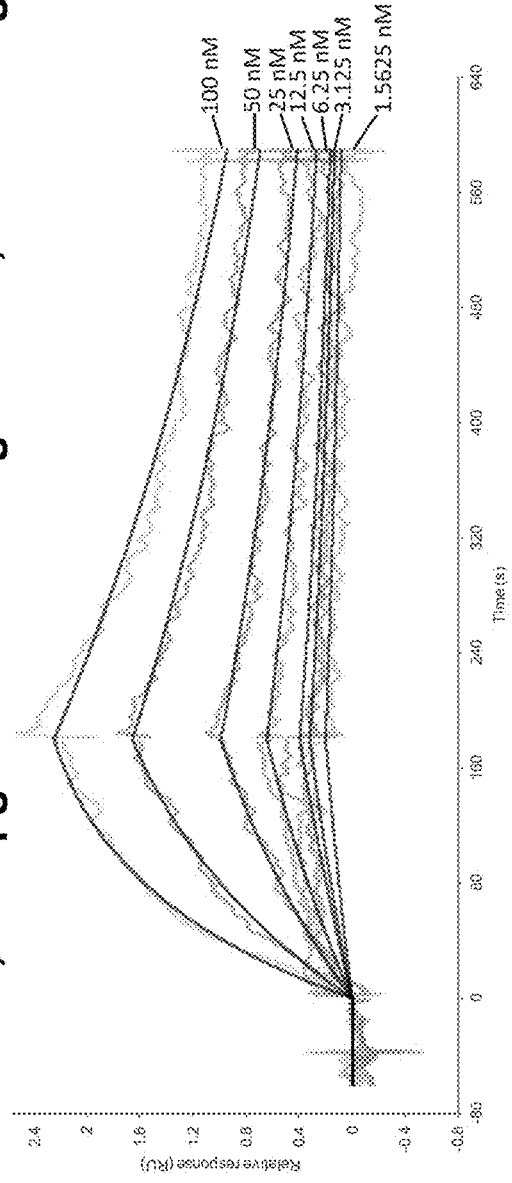
FIG. 21B is a graph showing results from Example 4 at various concentrations for VLVH; 0.25 µg/mL Mouse Integrin α7β1; 1:1 binding.
Figures 22A, 22B, 22C:
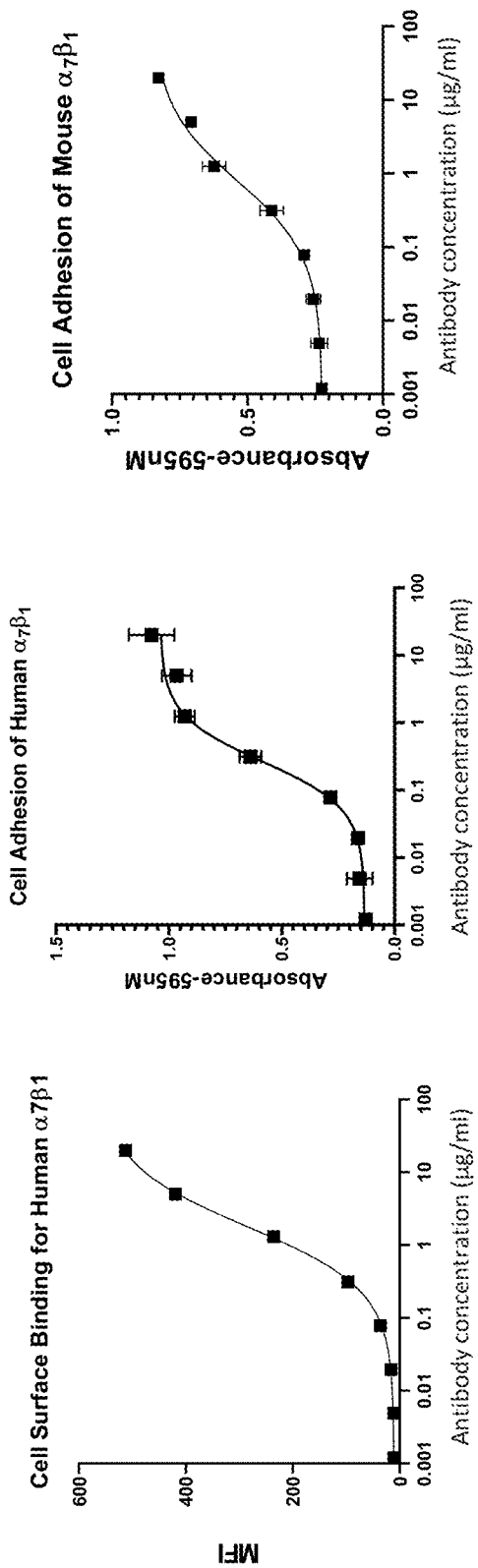
FIG. 22A is a graph showing results from Example 4 of VL3VHK20TFT binding to cell surfaces expressing integrin α7β1.
FIG. 22B is a graph showing results from Example 4 of VL3VHK20TFT enhanced human α7β1-expressing cell adhesion to laminin.
FIG. 22C is a graph showing results from Example 4 of VL3VHK20TFT enhanced murine α7β1-expressing cell adhesion to laminin.

The binding of VL3VHK20TFT Fab and 6A11 mAb to each mutant clone in an alanine scanning library of ITGA7 mutants was determined, in duplicate, by high-throughput flow cytometry. For each point, background fluorescence was subtracted from the raw data, which were then normalized to antibody (Ab) reactivity with wild-type (WT) target protein. For each mutant clone, the mean binding value was plotted as a function of expression (represented by control reactivity). To identify preliminary primary critical clones (red circles), a threshold (dashed lines) of >70% WT binding to control Ab and <20% WT binding to test Abs was applied. Secondary clones (blue circles) are highlighted for clones that did not meet the set thresholds but whose decreased binding activity and proximity to critical residues suggested that the mutated residue may be part of the antibody epitope. FIG. 17 shows a graph containing primary critical clones and secondary clones.

The critical residues for antibody binding are listed in Table 6. Mean binding reactivities (and ranges) are listed for all identified critical residues. Critical residues for Ab binding (S977, W978, W979, P980) were residues whose mutations were negative for binding to test Abs, but positive for binding to control antibody. Additional secondary residues (R958, M976) were identified that did not meet the threshold guidelines, but whose decreased binding activity and proximity to critical residues suggested that they may be part of the antibody epitope.

Critical residues (red spheres) were visualized on a crystal structure model of the target protein, based on an integrin alpha (x) beta (2) structure (PDB ID #3K71 in Xie et al., 2010, *Embo. J.* 29, 666-679) as shown in FIG. 18. Secondary residues (blue spheres) that may contribute to binding are also shown. One residue (R958) is not available on the model. Critical residues whose mutation gave the lowest reactivities with VL3VHK20TFT Fab are underlined in Table 6. Validated critical residues represent amino acids whose side chains make the highest energetic contributions to the antibody-epitope interaction (Bogan and Thorn, 1998, *J. Mol. Biol.* 280, 1-9; Lo Conte et al., 1999, *J. Mol. Biol.* 285, 2177-2198.); therefore, the highlighted residues (S977, W978, W979, P980) are likely the major energetic contributors to binding.

TABLE 6

Critical Residues for Antibody Binding
Binding Reactivity (% WT)

| Mutation | VL3VHK20TFT Fab HS | 6A11 MAb |
|---|---|---|
| R958A | 27.8 (0) | 114.3 (66) |
| M976A | 29.5 (7) | 149.4 (45) |
| S977A | 8.0 (1) | 97.6 (44) |
| W978A | −0.3 (0) | 96.4 (32) |
| W979A | −0.7 (2) | 87.9 (17) |
| P980A | 1.1 (0) | 111.8 (67) |

TABLE 7

| Human integrin alpha-7 (ITGA7; UniProt ID Q13683) amino acid sequence |
|---|
| MAGARSRDPWGASGICYLFGSLLVELLFSRAVAFNLDVMGALRK<br>EGEPGSLFGFSVALHRQLQPRPQSWLLVGAPQALALPGQQANRT<br>GGLFACPLSLEETDCYRVDIDQGADMQKESKENQWLGVSVRSQG<br>PGGKIVTCAHRYEARQRVDQILETRDMIGRCFVLSQDLAIRDEL<br>DGGEWKFCEGRPQGHEQFGFCQQGTAAAFSPDSHYLLFGAPGTY<br>NWKGTARVELCAQGSADLAHLDDGPYEAGGEKEQDPRLIPVPAN<br>SYFGLLFVTNIDSSDPDQLVYKTLDPADRLPGPAGDLALNSYLG<br>FSIDSGKGLVRAEELSFVAGAPRANHKGAVVILRKDSASRLVPE<br>VMLSGERLTSGFGYSLAVADLNSDGWPDLIVGAPYFFERQEELG<br>GAVYVYLNQGGHWAGISPLRLCGSPDSMFGISLAVLGDLNQDGF<br>PDIAVGAPFDGDGKVFIYHGSSLGVVAKPSQVLEGEAVGIKSFG<br>YSLSGSLDMDGNQYPDLLVGSLADTAVLFRARPILHVSHEVSIA |

TABLE 7-continued

| Human integrin alpha-7 (ITGA7; UniProt ID Q13683) amino acid sequence |
|---|
| PRSIDLEQPNCAGGHSVCVDLRVCFSYIAVPSSYSPTVALDYVL<br>DADTDRRLRGQVPRVTFLSRNLEEPKHQASGTVWLKHQHDRVCG<br>DAMFQLQENVKDKLRAIVVTLSYSLQTPRLRRQAPGQGLPPVAP<br>ILNAHQPSTQRAEIHFLKQGCGEDKICQSNLQLVRARFCTRVSD<br>TEFQPLPMDVDGTTALFALSGQPVIGLELMVTNLPSDPAQPQAD<br>GDDAHEAQLLVMLPDSLHYSGVRALDPAEKPLCLSNENASHVEC<br>ELGNPMKRGAQVTFYLILSTSGISIETTELEVELLLATISEQEL<br>HPVSARARVFIELPLSIAGMAIPQQLFFSGVVRGERAMQSERDV<br>GSKVKYEVTVSNQGQSLRTLGSAFLNIMWPHEIANGKWLLYPMQ<br>VELEGGQGPGQKGLCSPRPNILHLDVDSRDRRRRELEPPEQQEP<br>GERQEPSMSWWPVSSAEKKKNITLDCARGTANCVVFSCPLYSFD<br>RAAVLHVWGRLWNSTFLEEYSAVKSLEVIVRANITVKSSIKNLM<br>LRDASTVIPVMVYLDPMAVVAEGVPWWVILLAVLAGLLVLALLV<br>LLLWKMGFFKRAKHPEATVPQYHAVKIPREDRQQFKEEKTGTIL<br>RNNWGSPRREGPDAHPILAADGHPELGPDGHPGPGTA<br>(SEQ ID NO: 24) |

Example 4: Evaluation of Mouse and Humanized Antibodies to α7β1 Integrin

Antibody binding to human and mouse integrin α7β1 was evaluated. The mouse α7β1 antibody VLVH (Chimera with human IgG4 Fc, also referred to as hIgG4-23 in Table 10) and humanized α7β1 antibody VL3VHK20TFT were both found to cross react with human and mouse integrin α7β1. A comparison of the affinity measurement listed in Table 8 shows that humanized antibody VL3VHK20TFT had a lower KD for binding to both human and mouse integrin α7β1. The humanized antibody had about 3.33-fold lower KD for binding to human α7β1 and about 11.1-fold lower KD for binding to mouse α7β1 integrin. These data show an overall substantial affinity improvement for the humanized antibody VL3VHK20TFT over the chimera antibody with mouse hybridoma Fab region. FIG. 19 is a graph showing results at various concentrations for VL3VHK20TFT; 0.25 μg/mL Human Integrin α7β1; 1:1 binding. FIG. 20 is a graph showing results at various concentrations for VLVH; 0.25 μg/mL Human Integrin α7β1; 1:1 binding. FIG. 21A is a graph showing results at various concentrations for VL3VHK20 TFT; 0.25 μg/mL Mouse Integrin α7β1; 1:1 binding. FIG. 21B is a graph showing results at various concentrations for VLVH; 0.25 μg/mL Mouse Integrin α7β1; 1:1 binding.

Antibody binding to cell surface integrin α7β1 was evaluated by flow cytometry. K562 cells expressing human integrin α7β1 were used for VL3VHK20TFT antibody binding. FIG. 22A is a graph showing the antibody cell surface binding at various concentrations. Antibody VL3VHK20TFT was found to enhance both human α7β1 (FIG. 22B) and murine α7β1 (FIG. 22C) mediated adhesion to laminin.

TABLE 8

Evaluation of mouse and humanized antibodies to α7β1 integrin

| Kinetics model | Capture 1 Solution | Analyte 1 Solution | Kinetics $Chi^2$ ($RU^2$) | ka (1/Ms) | kd (1/s) | KD (M) |
|---|---|---|---|---|---|---|
| 1:1 binding | 0.25 μg/mL Human Integrin α7β1 | VL3VHK20TFT | 1.11E−01 | 2.58E+05 | 1.53E−04 | 5.93E−10 |
| 1:1 binding | 0.25 μg/mL Human Integrin α7β1 | VLVH | 7.36E−03 | 3.33E+05 | 6.52E−04 | 1.96E−09 |

TABLE 8-continued

Evaluation of mouse and humanized antibodies to α7β1 integrin

| Kinetics model | Capture 1 Solution | Analyte 1 Solution | Kinetics Chi² (RU²) | ka (1/Ms) | kd (1/s) | KD (M) |
|---|---|---|---|---|---|---|
| 1:1 binding | 0.25 µg/mL Mouse Integrin α7β1 | VL3VHK20TFT | 6.85E−03 | 2.39E+05 | 4.69E−04 | 1.96E−09 |
| 1:1 binding | 0.25 µg/mL Mouse Integrin α7β1 | VLVH | 6.70E−03 | 9.76E+04 | 2.13E−03 | 2.18E−08 |

Example 5: α7β1 Agonist Antibody Enhanced DMD Myoblast Cell Adhesion to Laminin

Method: Real-time monitoring of cellular reattachment from suspension was measured using an electrical impedance assay with an xCELLigence RTCA SP real-time cell-sensing device. DMD myoblast cells were seeded into E-plates coated with laminin 211. Cells were treated with antibodies respectively. The attachment rate was expressed as the cell index, with values expressed as the cell index±SD of triplicate wells.

Figure 23:
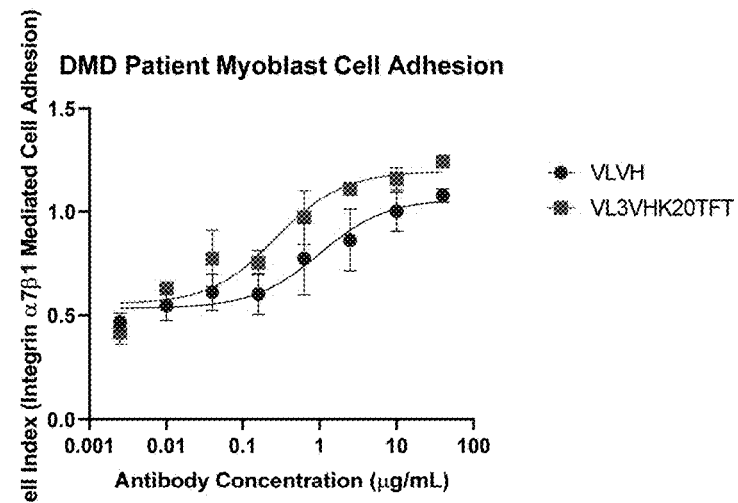
FIG. 23 is a graph showing results from Example 5 for antibody concentration in µg/mL vs cell index (integrin α7β1 mediated cell adhesion) for both murine antibody (VLVH) and humanized antibody (VL3VHK20TFT) enhanced myoblast cell adhesion on laminin.

Results: FIG. 23 is a graph showing antibody concentration in µg/mL vs cell index (integrin α7β1 mediated cell adhesion) for both murine antibody (VLVH) and humanized antibody (VL3VHK20TFT) enhanced myoblast cell adhesion on laminin. The humanized antibody was about 5-fold more potent than the murine antibody.

Example 6: α7β1 Agonist Antibody Protects Gastrocnemius Muscle from Injury

Method: Four murine test groups were established: a DBA2/IgG control, a mdx/IgG control, a mdx/Agonist antibody at 3 mg/kg, and a mdx/agonist antibody at 15 mg/kg. Muscle performance was measured in vivo with a 305C muscle lever system. The knee was isolated using a pin pressed against the tibial head and the foot firmly fixed to a footplate on the motor shaft. For the plantar flexor muscle group, contractions were elicited by percutaneous electrical stimulation of the sciatic nerve. A series of 20 tetanic stimulations (80 Hz, 0.2 ms pulse, 500 ms duration) were delivered at 0.1 Hz frequency. The foot was rotated against the direction of contraction by 10° over 250 ms, resulting in an eccentric contraction.

Figure 24:
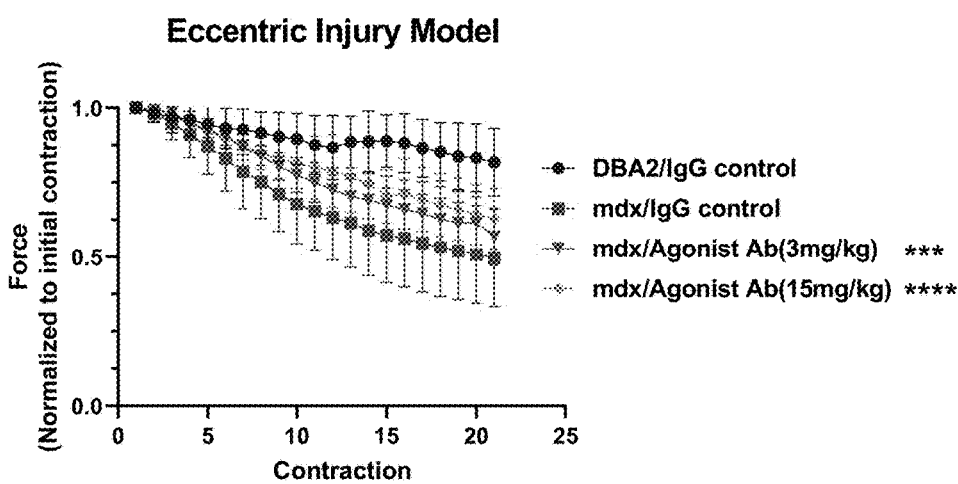
FIG. 24 is a graph showing results from Example 6 for contraction vs force (normalized to initial contraction) for the DBA2/IgG control, the mdx/IgG control, the mdx/ Agonist antibody at 3 mg/kg, and the mdx/agonist antibody at 15 mg/kg.

Results: FIG. 24 is a graph showing contraction vs force (normalized to initial contraction) for the DBA2/IgG control, the mdx/IgG control, the mdx/Agonist antibody at 3 mg/kg, and the mdx/agonist antibody at 15 mg/kg. Force for mdx mice dropped much more than the healthy control mice (DBAS). Integrin α7β1 agonist antibody treatment protected from eccentric injury with both doses (3 mg/kg and 15 mg/kg).

Example 7: α7β1 Agonist Antibody Agonist Antibody Improved Diaphragm Function

Method: Using the four murine groups from Example 6, muscle performance was measured in vitro with a 305C muscle lever system (Aurora Scientific Inc., Aurora, CAN) adapted with a horizontal perfusion bath. The entire diaphragm was placed in the horizontal bath of the 305C muscle lever system and perfused with physiological buffer oxygenated with 95% $O_2$/5% $CO_2$ and kept at 37° C. A series of 1 Hz and 100 Hz field stimulations (0.2 ms pulse, 100 ms duration) at 0.01 Hz frequency were delivered via platinum electrodes flanking the muscle to ensure that the sutures were tight and that the maximal developed force was stable.

Figure 25:
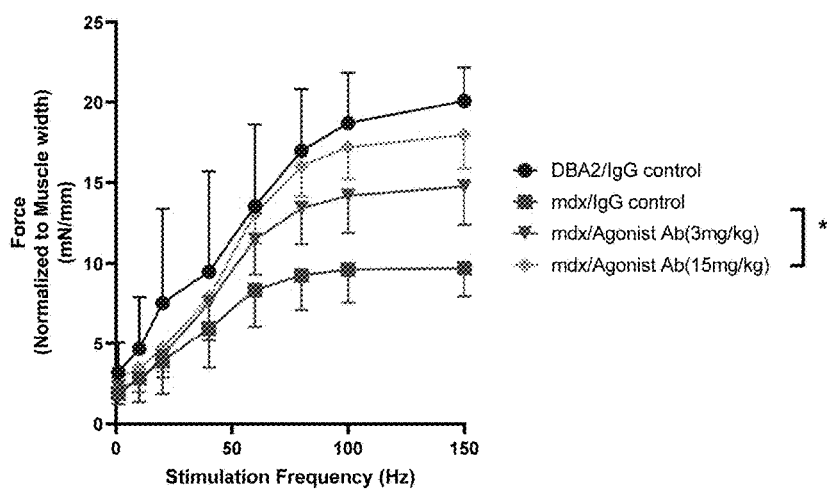
FIG. 25 is a graph showing results from Example 7 for stimulation frequency in Hz vs force (normalized to muscle width, mN/mm) for the DBA2/IgG control, the mdx/IgG control, the mdx/Agonist antibody at 3 mg/kg, and the mdx/agonist antibody at 15 mg/kg.

Results: FIG. 25 is a graph showing stimulation frequency in Hz vs force (normalized to muscle width, mN/mm) for the DBA2/IgG control, the mdx/IgG control, the mdx/Agonist antibody at 3 mg/kg, and the mdx/agonist antibody at 15 mg/kg. The mdx mice force dropped much more than the healthy control mice (DBAS). Treatment with the integrin α7β1 agonist antibody protected from eccentric injury with both doses (3 mg/kg and 15 mg/kg).

Example 8: α7β1 Agonist Antibody Treatment Improves Biomarkers

Method: Various biomarkers associated with muscular dystrophic damage were measured in mice and found to be improved with treatment.

Figure 26:
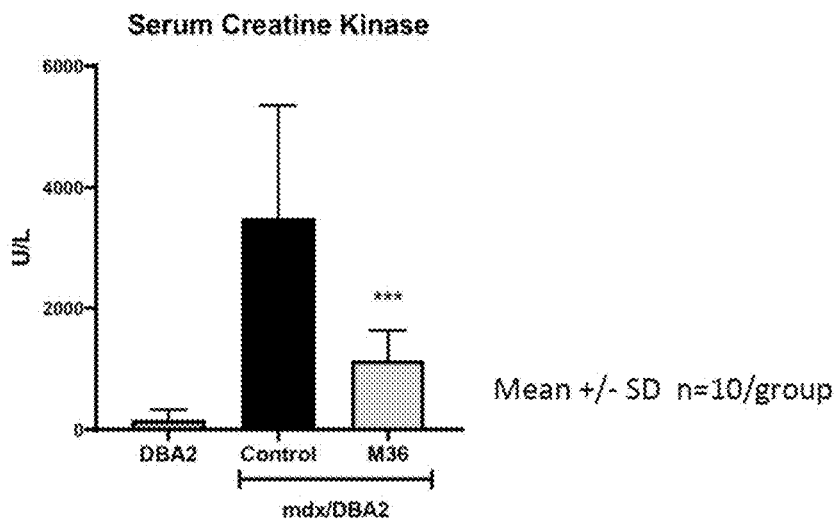
FIG. 26 is a bar graph showing the amount of serum creatine kinase, a biomarker for muscle damage, in the DBA2/IgG control, the mdx/IgG control, and treatment with the M36 agonist antibody.

FIG. 26 is a bar graph showing the amount of serum creatine kinase, a biomarker for muscle damage, in the DBA2/IgG control, the mdx/IgG control, and treatment with the M36 agonist antibody. Treatment with the M36 agonist antibody substantially reduced serum creatine kinase as compared to the mdx/IgG control.

Figure 27:
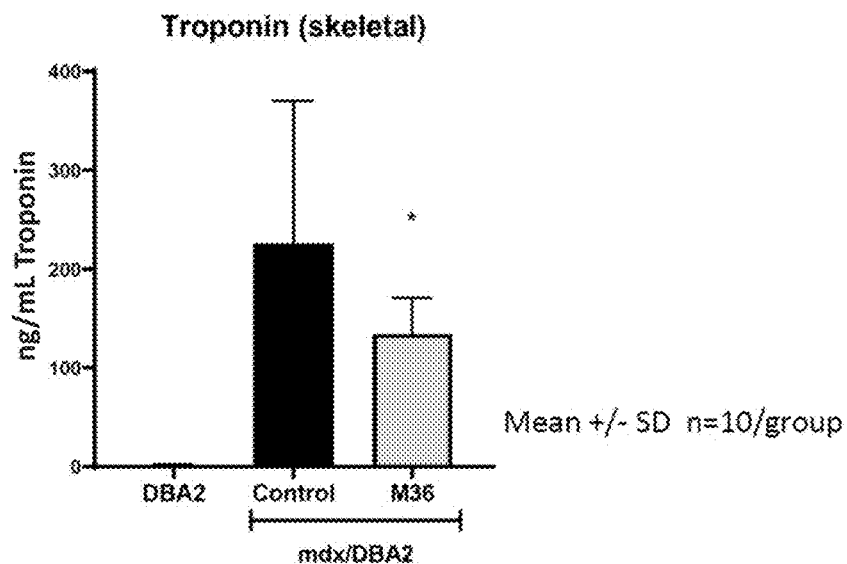
FIG. 27 is a bar graph showing the amount of skeletal troponin, a biomarker for muscular damage, in the DBA2/ IgG control, the mdx/IgG control, and treatment with the M36 agonist antibody.

FIG. 27 is a bar graph showing the amount of skeletal troponin, a biomarker for muscular damage, in the DBA2/IgG control, the mdx/IgG control, and treatment with the M36 agonist antibody. Treatment with the M36 agonist antibody substantially reduced skeletal troponin as compared to the mdx/IgG control.

Figure 28:
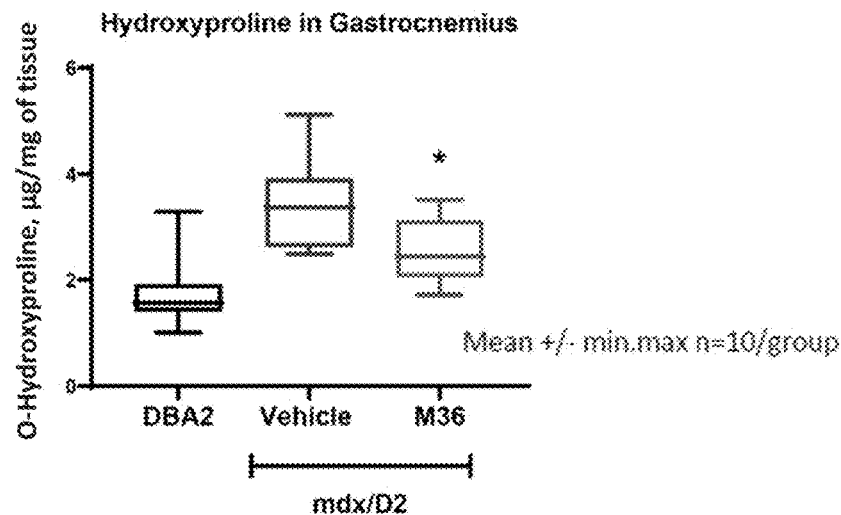
FIG. 28 is a bar graph showing the amount of O-hydroxyproline, a measure of collagen formation/fibrosis in the gastrocnemius muscle in the DBA2/IgG control, the mdx/ IgG control, and treatment with the M36 agonist antibody.

FIG. 28 is a bar graph showing the amount of O-hydroxyproline, a measure of collagen formation/fibrosis in the gastrocnemius muscle in the DBA2/IgG control, the mdx/IgG control, and treatment with the M36 agonist antibody. Treatment with the M36 agonist antibody substantially reduced collagen formation/fibrosis as determined by O-hydroxyproline when compared to the mdx/IgG control.

Example 9: Improved Properties of Modified α7β1 Agonist Antibodies

Figure 29:
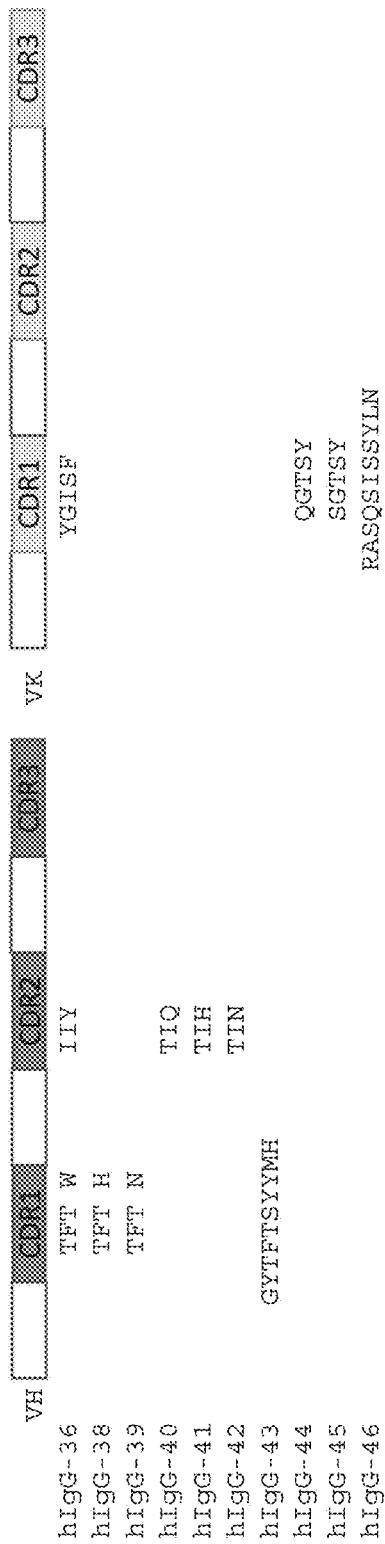
FIG. 29 shows various sequence variants generated by site-mutagenesis on amino acids located in heavy chain CDR1 and CDR2, or light chain CDR1, of antibody VL3VHK20TFT. YGISF: SEQ ID NO: 26. GYTFT-SYYMH: SEQ ID NO: 27. QGTSY: SEQ ID NO: 28. SGTSY: SEQ ID NO: 29. RASQSISSYLN: SEQ ID NO: 30.
Figure 30:
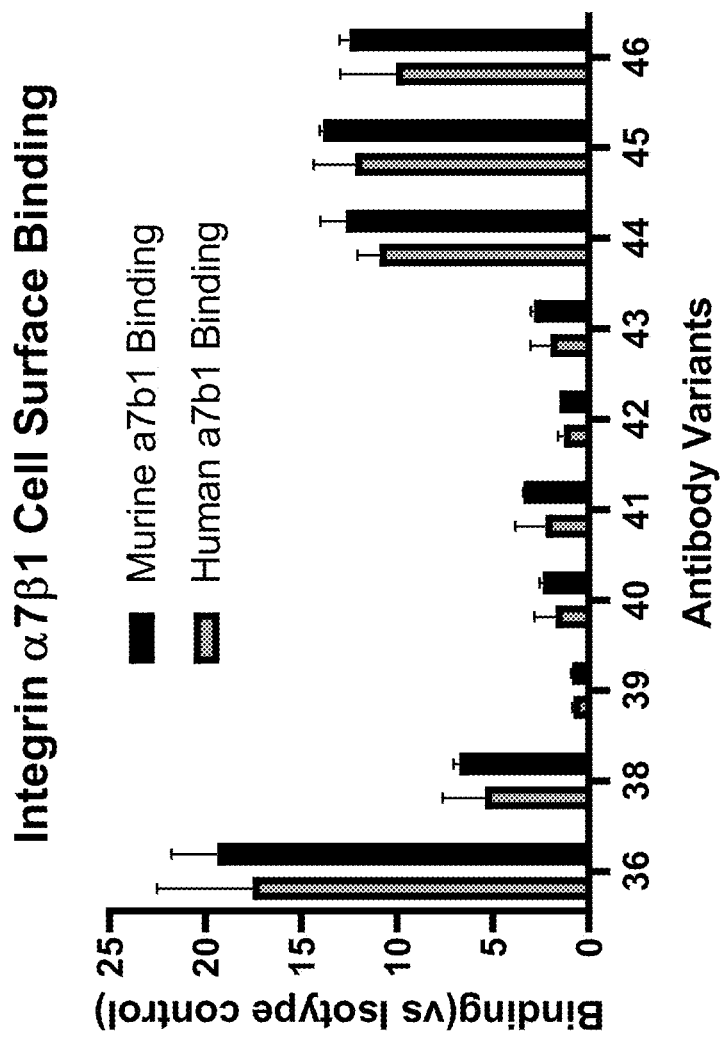
FIG. 30 is a bar graph showing binding to cell surface integrin α7β1 by antibody sequence variants. The binding was measured by flow cytometry and normalized to an IgG4 isotype control.

Amino acid substitutions, as shown in FIG. 29, were generated by site-directed mutagenesis of sequences of antibody VL3VHK20TFT (original sequences provided in Table 3) and were evaluated for an ability to reduce antibody polyspecificity. As shown further here, some of the variants that included hIgG-38 in the variable region of the heavy chain, and hIgG-44, 45 and 46 in the variable region of the light chain were found to retain integrin α7β1 binding activity (FIG. 30). An ELISA-based approach which employs the membrane proteins presented on the surface of a baculovirus particle (BVP) was used as a reagent to capture antibodies with cross-interaction propensity. Hydrophobic interaction chromatography (HIC) was used an analytical technique to probe antibody hydrophobicity. hIgG-38, 44 and 45 were shown to have more favorable biophysical properties, as shown in Table 9. Sequences of these antibodies are provided in Table 11, Table 12 and Table 13.

TABLE 9

BVP and HIC scores for humanized antibody variants

|  | BVP | HIC |
|---|---|---|
| hIgG-36 | 12.5 | 16.29 |
| hIgG-38 | 3.8 | 12.43 |
| hIgG-44 | 6.4 | 8.19 |
| hIgG-45 | 7.5 | 8.26 |
| hIgG-46 | 18.1 | 12.01 |

Example 10: Additional α7β1 Agonist Antibodies

Table 10 shows a range of α7β1 agonist IgG antibodies prepared from combinations of heavy chains and light chains whose amino acid sequences are provided after Table 10.

Heavy chain sequences VHK2, VHK4, VHK11, VHK12, VHK14, VHK20, VHK22, VHK33, VHK48, and VHK51 are humanized heavy chain sequences comprising variation in the HCDR3 sequence. Heavy chain sequences VHK20TFT-A to VHK20TFT-F comprise variation in the HCDR1 and HCDR2 sequences. Light chain sequences VL1-VL10 are humanized kappa chain sequences. Light chain sequences VL11, VL12 and VL13 comprise variation in the LCDR1 sequence. The sequences named "VH" and "VL" are chimeric molecules comprising murine IgG M36 variable regions and human IgG4 constant regions.

TABLE 10

Exemplary α7β1 IgG antibodies

| Human IgG antibody name | Light chain sequence | Heavy chain sequence | Other name for antibody |
|---|---|---|---|
| hIgG4-1 | VL1 | VHK33 | VL1VHK33 |
| hIgG4-2 | VL1 | VHK20 | VL1VHK20 |
| hIgG4-3 | VL1 | VHK22 | VL1 VHK22 |
| hIgG4-4 | VL1 | VHK48 | VL1 VHK48 |
| hIgG4-5 | VL1 | VHK14 | VL1 VHK14 |
| hIgG4-6 | VL1 | VHK7 | VL1 VHK7 |
| hIgG4-7 | VL1 | VHK51 | VL1 VHK51 |
| hIgG4-8 | VL1 | VHK11 | VL1 VHK11 |
| hIgG4-9 | VL1 | VHK2 | VL1 VHK2 |
| hIgG4-10 | VL1 | VHK4 | VL1 VHK4 |
| hIgG4-11 | VL2 | VHK33 | VL2 VHK33 |
| hIgG4-12 | VL2 | VHK20 | VL2 VHK20 |
| hIgG4-13 | VL2 | VHK22 | VL2 VHK22 |
| hIgG4-14 | VL2 | VHK48 | VL2 VHK48 |
| hIgG4-15 | VL2 | VHK14 | VL2 VHK14 |
| hIgG4-16 | VL2 | VHK7 | VL2 VHK7 |
| hIgG4-17 | VL2 | VHK51 | VL2 VHK51 |
| hIgG4-18 | VL2 | VHK11 | VL2 VHK11 |
| hIgG4-19 | VL2 | VHK2 | VL2 VHK2 |
| hIgG4-20 | VL2 | VHK4 | VL2 VHK4 |
| hIgG4-21 | VL1 | VHK12 | VL1 VHK12 |
| hIgG4-22 | VL2 | VHK12 | VL2 VHK12 |
| hIgG4-23 | VL | VH | VL VH |
| hIgG4-24 | VL1 | VH3 | VL1 VH3 |
| hIgG4-25 | VL2 | VH3 | VL2 VH3 |
| hIgG4-26 | VL | VHK20 | VL VHK20 |
| hIgG4-27 | VL | VH3 | VL VH3 |
| hIgG4-28 | VL3 | VHK20 | VL3 VHK20 |
| hIgG4-29 | VL4 | VHK20 | VL4 VHK20 |
| hIgG4-30 | VL5 | VHK20 | VL5 VHK20 |
| hIgG4-31 | VL6 | VHK20 | VL6 VHK20 |
| hIgG4-32 | VL7 | VHK20 | VL7 VHK20 |
| hIgG4-33 | VL8 | VHK20 | VL8 VHK20 |
| hIgG4-34 | VL9 | VHK20 | VL9 VHK20 |
| hIgG4-35 | VL10 | VHK20 | VL10 VHK20 |
| hIgG4-36 | VL3 | VHK20TFT | VL3 VHK20TFT |
| hIgG4-37 | VL3 | VHK20NTA | VL3 VHK20NTA |
| hIgG4-38 | VL3 | VHK20TFT-A | VL3 VHK20TFT-A |
| hIgG4-39 | VL3 | VHK20TFT-B | VL3 VHK20TFT-B |
| hIgG4-40 | VL3 | VHK20TFT-C | VL3 VHK20TFT-C |
| hIgG4-41 | VL3 | VHK20TFT-D | VL3 VHK20TFT-D |
| hIgG4-42 | VL3 | VHK20TFT-E | VL3 VHK20TFT-E |
| hIgG4-43 | VL3 | VHK20TFT-F | VL3 VHK20TFT-F |
| hIgG4-44 | VL11 | VHK20TFT | VL11 VHK20TFT |
| hIgG4-45 | VL12 | VHK20TFT | VLl2 VHK20TFT |
| hIgG4-46 | VL13 | VHK20TFT | VL13 VHK20TFT |
| hIgG4-47 | VL13 | VHK20TFT-F | VL13 VHK20TFT-F |
| hIgG4-48 | VL | VHK20TFT | VL VHK20TFT |
| hIgG4-49 | VL3 | VH | VL3 VH |

Heavy Chain Sequences (Underlined Portions in Each Sequence are, in Order, HCDR1, HCDR2 and HCDR3)

```
VHK33
                                              (SEQ ID NO: 31)
QVQLVQSGAEVKKPGASVKVSCKASGYNFTKYWINWVRQAPGQGLEWMGITYPGSSTSNYNEK

FKTRVTMTVDTSTSTAYMELSSLRSEDTAVYYCVRGDEWGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK20
                                              (SEQ ID NO: 32)
QVQLVQSGAEVKKPGASVKVSCKASGYNFTKYWINWVRQAPGQGLEWMGITYPGSSTSNYNEK

FKTRVTMTVDTSTSTAYMELSSLRSEDTAVYYCVKNDNWGQGTLVTVSSASTKGPSVFPLAPC

SRSTSESTAALGCLVKDYFPEPVTVSWNSGALTSGVHTFPAVLQSSGLYSLSSVVTVPSSSLG
```

-continued

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK22 (SEQ ID NO: 33)
QVQLVQSGAEVKKPGASVKVSCKAS<u>GYNFTKYW</u>INWVRQAPGQGLEWMGITY<u>PGSSTS</u>NYNEK

FKTRVTMTVDTSTSTAYMELSSLRSEDTAVYYC<u>VKNDV</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK48 (SEQ ID NO: 34)
QVQLVQSGAEVKKPGASVKVSCKAS<u>GYNFTKYW</u>INWVRQAPGQGLEWMGITY<u>PGSSTS</u>NYNEK

FKTRVTMTVDTSTSTAYMELSSLRSEDTAVYYC<u>VRRDN</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK14 (SEQ ID NO: 35)
QVQLVQSGAEVKKPGASVKVSCKAS<u>GYNFTKYW</u>INWVRQAPGQGLEWMGITY<u>PGSSTS</u>NYNEK

FKTRVTMTVDTSTSTAYMELSSLRSEDTAVYYC<u>VKGDV</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK7 (SEQ ID NO: 36)
QVQLVQSGAEVKKPGASVKVSCKAS<u>GYNFTKYW</u>INWVRQAPGQGLEWMGITY<u>PGSSTS</u>NYNEK

FKTRVTMTVDTSTSTAYMELSSLRSEDTAVYYC<u>VKGDK</u>WGQGTLVTVSSASTKGPSVFPLAPCS

RSTSESTAALGCLVKDYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDTLMISRTPEVTCVVVD

VSQEDPEVQFNWYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLG

VHK51 (SEQ ID NO: 37)
QVQLVQSGAEVKKPGASVKVSCKAS<u>GYNFTKYW</u>INWVRQAPGQGLEWMGITY<u>PGSSTS</u>NYNEK

FKTRVTMTVDTSTSTAYMELSSLRSEDTAVYYC<u>VRRDT</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

-continued

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK11
(SEQ ID NO: 38)
QVQLVQSGAEVKKPGASVKVSCKAS<u>GYNFTKY</u>WINWVRQAPGQGLEWMGITY<u>PGSSTS</u>NYNEK

FKTRVTMTVDTSTSTAYMELSSLRSEDTAVYYC<u>VKGDQ</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK2
(SEQ ID NO: 39)
QVQLVQSGAEVKKPGASVKVSCKAS<u>GYNFTKY</u>WINWVRQAPGQGLEWMGITY<u>PGSSTS</u>NYNEK

FKTRVTMTVDTSTSTAYMELSSLRSEDTAVYYC<u>VKGDA</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK4
(SEQ ID NO: 40)
QVQLVQSGAEVKKPGASVKVSCKAS<u>GYNFTKY</u>WINWVRQAPGQGLEWMGITY<u>PGSSTS</u>NYNEK

FKTRVTMTVDTSTSTAYMELSSLRSEDTAVYYC<u>VKGDE</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK12
(SEQ ID NO: 41)
QVQLVQSGAEVKKPGASVKVSCKAS<u>GYNFTKY</u>WINWVRQAPGQGLEWMGIIY<u>PGSSTS</u>NYNEK

FKTRVTMTVDTSTSTAYMELSSLRSEDTAVYYC<u>VKGDS</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VH
(SEQ ID NO: 42)
QVQLQQPGAELVKPGASVKLSCKAS<u>GYNFTKY</u>WINWVKQRPGQGLEWIGITY<u>PGSSTS</u>NYNEK

FKTKATLTVEISSTTAYMQLSSLTSDDSAVYYC<u>VRGDD</u>WGQGTTLTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VH3

(SEQ ID NO: 43)

QVQLVQSGAEVKKPGASVKVSCKAS<u>GYNFTKY</u>WINWVRQAPGQGLEWMGII<u>YPGSSTS</u>NYNEK

FKTRVTMTVDTSTSTAYMELSSLRSEDTAVYYC<u>VRGDD</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK20NFA (SEQ ID NO: 44)

QVQLVQSGAEVKKPGASVKVSCKAS<u>GYNFAKY</u>WINWVRQAPGQGLEWMGITY<u>PGSSTS</u>NYNE

KPFKTRVTMTVDTSTSTAYMELSSLRSEDTAVYYC<u>VKNDN</u>WGQGTLVTVSSASTKGPSVFPLAP

CSRSTSESTAALGCLVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLG

VHK20TFT-A (SEQ ID NO: 45)

QVQLVQSGAEVKKPGASVKVSCKAS<u>GYTFTKYH</u>INWVRQAPGQGLEWMGIIY<u>PGSSTS</u>NYNEK

FKTRVTMTVDTSTSTAYMELSSLRSEDTAVYYC<u>VKNDN</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK20TFT-B (SEQ ID NO: 46)

QVQLVQSGAEVKKPGASVKVSCKAS<u>GYTFTKYN</u>INWVRQAPGQGLEWMGITY<u>PGSSTS</u>NYNEK

FKTRVTMTVDTSTSTAYMELSSLRSEDTAVYYC<u>VKNDN</u>WGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG

VHK20TFT-C (SEQ ID NO: 47)

QVQLVQSGAEVKKPGASVKVSCKAS<u>GYTFTKYW</u>INWVRQAPGQGLEWMGTIQ<u>PGSSTS</u>NYNE

KPFKTRVTMTVDTSTSTAYMELSSLRSEDTAVYYC<u>VKNDN</u>WGQGTLVTVSSASTKGPSVFPLAP

CSRSTSESTAALGCLVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPPKPKDTLMISRTPEV

```
TCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLG

VHK20TFT-D
                                                    (SEQ ID NO: 48)
QVQLVQSGAEVKKPGASVKVSCKASGYTFTKYWINWVRQAPGQGLEWMGTIHPGSSTSNYNE

KFKTRVTMTVDTSTSTAYMELSSLRSEDTAVYYCVKNDNWGQGTLVTVSSASTKGPSVFPLAP

CSRSTSESTAALGCLVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLG

VHK20TFT-E
                                                    (SEQ ID NO: 49)
QVQLVQSGAEVKKPGASVKVSCKASGYTFTKYWINWVRQAPGQGLEWMGTINPGSSTSNYNE

KFKTRVTMTVDTSTSTAYMELSSLRSEDTAVYYCVKNDNWGQGTLVTVSSASTKGPSVFPLAP

CSRSTSESTAALGCLVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLG

VHK20TFT-F
                                                    (SEQ ID NO: 50)
QVQLVQSGAEVKKPGASVKVSCKASGYTFTSYYMHWVRQAPGQGLEWMGIIYPGSSTSNYNEK

FKTRVTMTVDTSTSTAYMELSSLRSEDTAVYYCVKNDNWGQGTLVTVSSASTKGPSVFPLAPC

SRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLG
```

Additional Heavy-Chain Complementarity Determining Regions (HCDRs)
HCDR1
  GYNFAKYW (SEQ ID NO: 75)
  GYTFTKYN (SEQ ID NO: 76)
HCDR3
  VRGDE (SEQ ID NO: 77)
  VKNDV (SEQ ID NO: 78)
  VRRDN (SEQ ID NO: 79)
  VKGDV (SEQ ID NO: 80)
  VKGDK (SEQ ID NO: 81)
  VRRDT (SEQ ID NO: 82)
  VKGDQ (SEQ ID NO: 83)
  VKGDA (SEQ ID NO: 84)
  VKGDE (SEQ ID NO: 85)
  VRGDE (SEQ ID NO: 86)
  VKGDS (SEQ ID NO: 87)

Light Chain Sequences (Underlined Portions in Each Sequence are, in Order, LCDR1, LCDR2 and LCDR3)

```
VL1
                                                    (SEQ ID NO: 51)
DIQMTQSPSSLSASVGDRVTITCRASESVDNYGISFMNWYQQKPGKAPKLLIYAASDLGSVPSR

FSGSGSGTDFTLTISSLQPEDFATYYCHQSKEVPYTFGQGTKLEIKRTVAAPSVFIFPPSDEQLK

TASVVCLLNNFYPREAKVQWKVDNALQSGNSQESVTEQDSKDSTYSLSSTLTLSKADYEKHKV

SGYACEVTHQGLSSPVTKSFNRGEC
```

-continued

VL2

(SEQ ID NO: 52)
DIQLTQSPSFLSASVGDRVTITCRAS<u>ESVDNYGISF</u>MNWYQQKPGKAPKLLIY<u>AAS</u>DLGSGVPSRF
SGSGSGTDFTLTISSLQPEDFATYFC<u>HQSKEVPYT</u>FGQGTKLEIKRTVAAPSVFIFPPSDEQLKSG
TASVVCLLNNFYPREAKVQWKVDNALQSGNSQESVTEQDSKDSTYSLSSTLTLSKADYEKHKVYAC
EVTHQGLSSPVTKSFNRGEC

VL3

(SEQ ID NO: 53)
DIQMTQSPSSLSASVGDRVTITCRAS<u>ESVDNYGISF</u>MNWFQQKPGKAPKLLIY<u>AAS</u>DLGSGVPSR
FSGSGSGTDFTLTISSLQPEDFATYYC<u>HQSKEVPYT</u>FGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

VL4

(SEQ ID NO: 54)
DIQLTQSPSSLSVSVGDRATITCRAS<u>ESVDNYGISF</u>MNWFQQKPGKAPKLLIY<u>AAS</u>DLGSGVPSRF
SGSGSGTDFTLTISSMQPEDFATYYC<u>HQSKEVPYT</u>FGQGTKLEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

VL5

(SEQ ID NO: 55)
DIQLTQSPSSLSVSVGDRATITCRAS<u>ESVDNYGISF</u>MNWFQQKPGKAPKLLIY<u>AAS</u>DLGSGVPSRF
SGSGSGTDFTLTISSMQPEDSATYYC<u>HQSKEVPYT</u>FGQGTKLEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

VL (SEQ ID NO: 56)
DIVLTQSPASLAVSLGQRATISCRAS<u>ESVDNYGISF</u>MNWFQQKPGQPPKLLIY<u>AAS</u>DLGSGVPARF
TGSGSGTDFSLNIHPMEEDDSAMYFC<u>HQSKEVPYT</u>FGGGTKLEIKRTVAAPSVFIFPPSDEQLKSG
TASVVCLLNNFYPREAKVQWKVDNALQSGNSQESVTEQDSKDSTYSLSSTLTLSKADYEKHKV
YACEVTHQGLSSPVTKSFNRGEC

VL6

(SEQ ID NO: 57)
DIQLTQSPSSLSASVGDRVTITCRAS<u>ESVDNYGISF</u>MNWYQQKPGKAPKLLIY<u>AAS</u>DLGSGVPSRF
SGSGSGTDFTLTISSLQPEDFATYFC<u>HQSKEVPYT</u>FGQGTKLEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

VL7

(SEQ ID NO: 58)
DIQLTQSPSSLSASVGDRVTITCRAS<u>ESVDNYGISF</u>MNWYQQKPGKAPKLLIY<u>AAS</u>DLGSGVPSR
FTGSGSGTDFSLTISSLQPEDFATYFC<u>HQSKEVPYT</u>FGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

VL8

(SEQ ID NO: 59)
DIQLTQSPSSLSVSVGDRATITCRAS<u>ESVDNYGISF</u>MNWYQQKPGKAPKLLIY<u>AAS</u>DLGSGVPSR
FTGSGSGTDFSLTISSMQPEDFATYFC<u>HQSKEVPYT</u>FGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

-continued

VL9 (SEQ ID NO: 60)
DIQMTQSPSSLSASVGDRVTITCRASESVDNYGISFMNWFQQKPGKAPKLLIYAASDLGSGVPSR
FSGSGSGTDFTLTISSLQPEDFATYFCHQSKEVPYTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

VL10 (SEQ ID NO: 61)
DIQLTQSPSFLSASVGDRVTITCRASESVDNYGISFMNWFQQKPGKAPKLLIYAASDLGSGVPSRF
SGSGSGTDFTLTISSLQPEDFATYFCHQSKEVPYTFGQGTKLEIKRTVAAPSVFIFPPSDEQLKS
GTASVVCLLNNFYPREAKVQWKVDNALQSGNSQESVTEQDSKDSTYSLSSTLTLSKADYEKHKVY
ACEVTHQGLSSPVTKSFNRGEC

VL11 (SEQ ID NO: 62)
DIQMTQSPSSLSASVGDRVTITCRASESVDNQGTSYMNWFQQKPGKAPKLLIYAASDLGSGVPSR
FSGSGSGTDFTLTISSLQPEDFATYYCHQSKEVPYTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

VL12 (SEQ ID NO: 63)
DIQMTQSPSSLSASVGDRVTITCRASESVDNSGTSYMNWFQQKPGKAPKLLIYAASDLGSGVPSR
FSGSGSGTDFTLTISSLQPEDFATYYCHQSKEVPYTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

VL13 (SEQ ID NO: 64)
DIQMTQSPSSLSASVGDRVTITCRASQSISSYLNSFMNWFQQKPGKAPKLLIYAASDLGSGVPSR
FSGSGSGTDFTLTISSLQPEDFATYYCHQSKEVPYTFGQGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

TABLE 11

Amino acid sequences of antibody hIgG-38

| | | |
|---|---|---|
| HCDR1 | GYTFTKYH | SEQ ID NO: 65 |
| HCDR2 | IYPGSSTS | SEQ ID NO: 3 |
| HCDR3 | VKNDN | SEQ ID NO: 66 |
| LCDR1 | ESVDNYGISF | SEQ ID NO: 5 |
| LCDR2 | AAS | SEQ ID NO: 6 |
| LCDR3 | HQSKEVPYT | SEQ ID NO: 7 |
| VH (CDR sequences are underlined) | QVQLVQSGAEVKKPGASVKVSCKASGYTFTKYHINWVRQAPGQGLEWMGIIYPGSSTSNYNEKFKTRVTMTVDTSTSTAYMELSSLRSEDTAVYYCVKNDNWGQGTLVTVSS | SEQ ID NO: 67 |
| VL (CDR sequences are underlined) | DIQMTQSPSSLSASVGDRVTITCRASESVDNYGISFMNWFQQKPGKAPKLLIYAASDLGSGVPSRFSGSGSGTDFTLTISSLQPEDFATYYCHQSKEVPYTFGQGTKLEIK | SEQ ID NO: 17 |
| Heavy Chain amino acid sequence (IgG4) (CDR sequences are underlined) | QVQLVQSGAEVKKPGASVKVSCKASGYTFTKYHINWVRQAPGQGLEWMGIIYPGSSTSNYNEKFKTRVTMTVDTSTSTAYMELSSLRSDETAVYYCVKNDNWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPR | SEQ ID NO: 45 |

TABLE 11-continued

Amino acid sequences of antibody hIgG-38

| | | |
|---|---|---|
| | EPQVYTLPPSQEEM TKNQVSLTCLVKGF YPSDIAVEWESNGQ PENNYKTTPPVLDS DGSFFLYSRLTVDK SRWQEGNVFSCSVM HEALHNHYTQKSLS LSLG | |
| Light Chain amino acid sequence (CDR sequences are underlined) | DIQMTQSPSSLSAS VGDRVTITCRASES VDNYGISFMNWFQQ KPGKAPKLLIYAAS DLGSGVPSRFSGSG SGTDFTLTISSLQP EDFATYYCHQSKEV PYTFGQGTKLEIKR TVAAPSVFIFPPSD EQLKSGTASVVCLL NNFYPREAKVQWKV DNALQSGNSQESVT EQDSKDSTYSLSST LTLSKADYEKHKVY ACEVTHQGLSSPVT KSFNRGEC | SEQ ID NO: 53 |

TABLE 12

Amino acid sequences of antibody hIgG-44

| | | |
|---|---|---|
| HCDR1 | GYTFTKYW | SEQ ID NO: 14 |
| HCDR2 | IYPGSSTS | SEQ ID NO: 3 |
| HCDR3 | VKNDN | SEQ ID NO: 68 |
| LCDR1 | ESVDNQGTSY | SEQ ID NO: 69 |
| LCDR2 | AAS | SEQ ID NO: 6 |
| LCDR3 | HQSKEVPYT | SEQ ID NO: 7 |
| VH (CDR sequences are underlined) | QVQLVQSGAEVKKPGASVKVSCKA SGYTFTKYWINWVRQAPGQGLEWM GIIYPGSSTSNYNEKFKTRVTMTV DTSTSTAYMELSSLRSEDTAVYYC VKNDNWGQGTLVTVSS | SEQ ID NO: 16 |
| VL (CDR sequences are underlined) | DIQMTQSPSSLSASVGDRVTITCR ASESVDNQGTSYMNWFQQKPGKAP KLLIYAASDLGSGVPSRFSGSGSG TDFTLTISSLQPEDFATYYCHQSK EVPYTFGQGTKLEIK | SEQ ID NO: 70 |
| Heavy Chain amino acid sequence (IgG4) (CDR sequences are underlined) | QVQLVQSGAEVKKPGASVKVSCKA SGYTFTKYWINWVRQAPGQGLEWM GIIYPGSSTSNYNEKFKTRVTMTV DTSTSTAYMELSSLRSEDTAVYYC VKNDNWGQGTLVTVSSASTKGPSV FPLAPCSRSTSESTAALGCLVKDY FPEPVTVSWNSGALTSGVHTFPAV LQSSGLYSLSSVVTVPSSSLGTKT YTCNVDHKPSNTKVDKRVESKYGP PCPPCPAPEFLGGPSVFLFPPKPK DTLMISRTPEVTCVVVDVSQEDPE VQFNWYVDGVEVHNAKTKPREEQF NSTYRVVSVLTVLHQDWLNGKEYK CKVSNKGLPSSIEKTISKAKGQPR EPQVYTLPPSQEEMTKNQVSLTCL | SEQ ID NO: 18 |

TABLE 12 -continued

Amino acid sequences of antibody hIgG-44

| | | |
|---|---|---|
| | VKGFYPSDIAVEWESNGQPENNYK TTPPVLDSDGSFFLYSRLTVDKSR WQEGNVFSCSVMHEALHNHYTQKS LSLSLG | |
| Light Chain amino acid sequence (CDR sequences are underlined) | DIQMTQSPSSLSASVGDRVTITCR ASESVDNQGTSYMNWFQQKPGKAP KLLIYAASDLGSGVPSRFSGSGSG TDFTLTISSLQPEDFATYYCHQSK EVPYTFGQGTKLEIKRTVAAPSVF IFPPSDEQLKSGTASVVCLLNNFY PREAKVQWKVDNALQSGNSQESVT EQDSKDSTYSLSSTLTLSKADYEK HKVYACEVTHQGLSSPVTKSFNRG EC | SEQ ID NO: 62 |

TABLE 13

Amino acid sequences of antibody hIgG-45

| | | |
|---|---|---|
| HCDR1 | GYTFTKYW | SEQ ID NO: 14 |
| HCDR2 | IYPGSSTS | SEQ ID NO: 3 |
| HCDR3 | VKNDN | SEQ ID NO: 68 |
| LCDR1 | ESVDNSGTSY | SEQ ID NO: 71 |
| LCDR2 | AAS | SEQ ID NO: 6 |
| LCDR3 | HQSKEVPYT | SEQ ID NO: 7 |
| VH (CDR sequences are underlined) | QVQLVQSGAEVKKPGASVKVSCKASGYTF TKYWINWVRQAPGQGLEWMGIIYPGSSTS NYNEKFKTRVTMTVDTSTSTAYMELSSLR SEDTAVYYCVKNDNWGQGTLVTVSS | SEQ ID NO: 16 |
| VL (CDR sequences are underlined) | DIQMTQSPSSLSASVGDRVTITCRASESV DNSGTSYMNWFQQKPGKAPKLLIYAASDL GSGVPSRFSGSGSGTDFTLTISSLQPEDF ATYYCHQSKEVPYTFGQGTKLEIK | SEQ ID NO: 72 |
| Heavy Chain amino acid sequence (IgG4) (CDR sequences are underlined) | QVQLVQSGAEVKKPGASVKVSCKASGYTF TKYWINWVRQAPGQGLEWMGIIYPGSSTS NYNEKFKTRVTMTVDTSTSTAYMELSSLR SEDTAVYYCVKNDNWGQGTLVTVSSASTK GPSVFPLAPCSRSTSESTAALGCLVKDYF PEPVTVSWNSGALTSGVHTFPAVLQSSGL YSLSSVVTVPSSSLGTKTYTCNVDHKPSN TKVDKRVESKYGPPCPPCPAPEFLGGPSV FLFPPKPKDTLMISRTPEVTCVVVDVSQE DPEVQFNWYVDGVEVHNAKTKPREEQFNS TYRVVSVLTVLHQDWLNGKEYKCKVSNKG LPSSIEKTISKAKGQPREPQVYTLPPSQE EMTKNQVSLTCLVKGFYPSDIAVEWESNG QPENNYKTTPPVLDSDGSFFLYSRLTVDK SRWQEGNVFSCSVMHEALHNHYTQKSLSL SLG | SEQ ID NO: 18 |
| Light Chain amino acid sequence (CDR sequences are underlined) | DIQMTQSPSSLSASVGDRVTITCRASESV DNSGTSYMNWFQQKPGKAPKLLIYAASDL GSGVPSRFSGSGSGTDFTLTISSLQPEDF ATYYCHQSKEVPYTFGQGTKLEIKRTVAA PSVFIFPPSDEQLKSGTASVVCLLNNFYP REAKVQWKVDNALQSGNSQESVTEQDSKD STYSLSSTLTLSKADYEKHKVYACEVTHQ GLSSPVTKSFNRGEC | SEQ ID NO: 63 |

Each document cited herein, including publications, patents, patent applications and published patent applications, is entirely incorporated by reference herein.

Although the foregoing invention has been described in some detail by way of illustration and example for purposes of clarity of understanding, it is apparent to those skilled in the art that certain minor changes and modifications will be practiced. The description and examples should not be construed as limiting the scope of the invention.

NUMBERED EMBODIMENTS

Notwithstanding the appended claims, the disclosure sets forth the following numbered embodiments:

1. A pharmaceutical agent that is an agonist of at least one of α7β1 integrin, α6β1 integrin and α3β1 integrin and that binds to the extracellular domain of at least one of α7 protein, α6 protein and α3 protein.

2. The pharmaceutical agent of embodiment 1, wherein the pharmaceutical agent binds at least one of:
   the laminin binding domain of at least one of α7 protein, α6 protein and α3 protein;
   the CALF-1 domain of at least one of α7 protein, α6 protein and α3 protein; and
   the CALF-2 domain of at least one of α7 protein, α6 protein and α3 protein.

3. The pharmaceutical agent of embodiment 1 that is an agonist of α7β1 integrin and that binds specifically to the α7 protein.

4. The pharmaceutical agent of embodiment 1, with the negative proviso that the pharmaceutical agent does not increase the amount of α7 protein in a muscle cell of a subject when the pharmaceutical agent is administered to the subject.

5. The pharmaceutical agent of any one of embodiments 1-4, wherein the pharmaceutical agent is an antibody.

6. The pharmaceutical agent of embodiment 5, wherein the antibody is a monoclonal antibody.

7. The pharmaceutical agent of embodiment 5, wherein the antibody is a multispecific antibody.

8. The pharmaceutical agent of embodiment 7, wherein the multispecific antibody is a bispecific antibody.

9. The pharmaceutical agent of embodiment 5, wherein the antibody is human, humanized or chimeric.

10. The pharmaceutical agent of embodiment 1, wherein the pharmaceutical agent activates at least one of α7β1 integrin, α6β1 integrin and α3β1 integrin.

11. The pharmaceutical agent of embodiment 1, wherein the pharmaceutical agent stabilizes the active conformation of at least one of α7β1 integrin, α6β1 integrin and α3β1 integrin.

12. The pharmaceutical agent of embodiment 3, wherein the pharmaceutical agent does not bind specifically to the β1 protein.

13. The pharmaceutical agent of any one of embodiments 1-12, wherein the pharmaceutical agent increases the adhesion of a myoblast to merosin.

14. The pharmaceutical agent of embodiment 13, wherein the myoblast is a healthy human myoblast or a healthy murine myoblast.

15. The pharmaceutical agent of embodiment 13, wherein the myoblast is a human myoblast or a murine myoblast that is at least one of: dystrophin deficient, comprises a mutation in dystrophin or comprises non-functioning dystrophin.

16. The pharmaceutical agent of any one of embodiments 1-12, wherein the pharmaceutical agent increases the adhesion of a myotube to merosin.

17. The pharmaceutical agent of embodiment 16, wherein the myotube is a healthy human myotube or a healthy murine myotube.

18. The pharmaceutical agent of embodiment 16, wherein the myotube is a human myotube or a murine myotube that is at least one of: dystrophin deficient, comprises a mutation in dystrophin or comprises non-functioning dystrophin.

19. A monoclonal antibody that is an agonist of α7β1 integrin, or an antibody fragment thereof, wherein the antibody or the antibody fragment binds specifically to an epitope of α7 protein, wherein the epitope comprises, consists essentially of, or consists of:
   (i) the amino acid sequence of SEQ ID NO: 10 or SEQ ID NO: 1;
   (ii) 5-10, 10-15, 15-20, 20-25, 25-30, 30-35 or 35-40 amino acids of SEQ ID NO: 10 or SEQ ID NO: 1; or
   (iii) 5-10, 10-15, 15-20, 20-25, 25-30, 30-35 or 35-40 amino acids of SEQ ID NO: 24.

20. A monoclonal antibody that is an agonist of α7β1 integrin, or an antibody fragment thereof, wherein the antibody or the antibody fragment binds specifically to an epitope of α7 protein, wherein the epitope comprises SWWP (SEQ ID NO: 25).

21. A monoclonal antibody that is an agonist of α7β1 integrin, or an antibody fragment thereof, wherein the antibody or the antibody fragment binds specifically to an epitope comprising the residues S977, W978, W979 and P980 of SEQ ID NO: 24.

22. The antibody or the antibody fragment of embodiment 20 or 21, wherein the epitope comprises, consists essentially of, or consists of 5-10 or 10-15 amino acids of SEQ ID NO: 24.

23. A monoclonal antibody that is an agonist of α71 integrin, or an antibody fragment thereof, wherein the antibody or the antibody fragment binds specifically to an epitope comprising the residues R958, M976, S977, W978, W979 and P980 of SEQ ID NO: 24.

24. The antibody or the antibody fragment of embodiment 23, wherein the epitope comprises, consists essentially of, or consists of 6-10 or 10-15 amino acids of SEQ ID NO: 24.

25. The antibody or the antibody fragment of any one of embodiments 20-24, wherein the epitope is continuous.

26. The antibody or the antibody fragment of any one of embodiments 20-24, wherein the epitope is discontinuous.

27. The antibody or the antibody fragment of any one of embodiments 20-26, wherein the antibody or the antibody fragment comprises a heavy chain variable (VH) region comprising an HCDR1, an HCDR2 and an HCDR3, and a light chain variable (VL) region comprising an LCDR1, an LCDR2 and an LCDR3,
   (i) wherein the HCDR3 comprises SEQ ID NO: 15; and/or wherein the LCDR3 comprises SEQ ID NO: 7;
   (ii) wherein the HCDR3 comprises SEQ ID NO: 66; and/or wherein the LCDR3 comprises SEQ ID NO: 7; or
   (iii) wherein the HCDR3 comprises SEQ ID NO: 68; and/or wherein the LCDR3 comprises SEQ ID NO: 7.

28. The antibody or the antibody fragment of embodiment 27, wherein the HCDR2 comprises SEQ ID NO: 3; and/or wherein the LCDR2 comprises SEQ ID NO: 6.

29. The antibody or the antibody fragment of embodiment 27 or 28,
   (i) wherein the HCDR1 comprises SEQ ID NO: 14; and/or wherein the LCDR1 comprises SEQ ID NO: 5;
   (ii) wherein the HCDR1 comprises SEQ ID NO: 65; and/or wherein the LCDR1 comprises SEQ ID NO: 5;

(iii) wherein the HCDR1 comprises SEQ ID NO: 14; and/or wherein the LCDR1 comprises SEQ ID NO: 69; or (iv) wherein the HCDR1 comprises SEQ ID NO: 14; and/or wherein the LCDR1 comprises SEQ ID NO: 71.

30. A monoclonal antibody that is an agonist of α7β1 integrin, or an antibody fragment thereof, wherein the antibody or the antibody fragment comprises a heavy chain variable (VH) region and a light chain variable (VL) region, wherein the VH region amino acid sequence comprises HCDR1 of SEQ ID NO: 2, HCDR2 of SEQ ID NO: 3 and HCDR3 of SEQ ID NO: 4, or a variant thereof having 5 or fewer conservative amino acid substitutions in HCDR1, HCDR2, and/or HCDR3;

wherein the VH region amino acid sequence comprises HCDR1 of SEQ ID NO: 14, HCDR2 of SEQ ID NO: 3 and HCDR3 of SEQ ID NO: 15, or a variant thereof having 5 or fewer conservative amino acid substitutions in HCDR1, HCDR2, and/or HCDR3;

wherein the VH region amino acid sequence comprises HCDR1 of SEQ ID NO: 65, HCDR2 of SEQ ID NO: 3 and HCDR3 of SEQ ID NO: 66, or a variant thereof having 5 or fewer conservative amino acid substitutions in HCDR1, HCDR2, and/or HCDR3; or wherein the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3.

31. A monoclonal antibody that is an agonist of α7β1 integrin, or an antibody fragment thereof, wherein the antibody or the antibody fragment comprises a light chain variable (VL) region and a heavy chain variable (VH) region, wherein the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3;

wherein the VL region amino acid sequence comprises LCDR1 of SEQ ID NO: 69, LCDR2 of SEQ ID NO: 6 and LCDR3 of SEQ ID NO: 7, or a variant thereof having 5 or fewer conservative amino acid substitutions in LCDR1, LCDR2, and/or LCDR3; or wherein the VL region amino acid sequence comprises LCDR1 of SEQ ID NO: 71, LCDR2 of SEQ ID NO: 6 and LCDR3 of SEQ ID NO: 7, or a variant thereof having 5 or fewer conservative amino acid substitutions in LCDR1, LCDR2, and/or LCDR3.

32. A monoclonal antibody that is an agonist of α7β1 integrin, or an antibody fragment thereof, wherein the antibody or the antibody fragment comprises a heavy chain variable (VH) region and a light chain variable (VL) region, wherein:

(i) the VH region amino acid sequence comprises HCDR1 of SEQ ID NO: 2, HCDR2 of SEQ ID NO: 3 and HCDR3 of SEQ ID NO: 4, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3;

(ii) the VH region amino acid sequence comprises HCDR1 of SEQ ID NO: 14, HCDR2 of SEQ ID NO: 3 and HCDR3 of SEQ ID NO: 15, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3;

(iii) the VH region amino acid sequence comprises HCDR1 of SEQ ID NO: 65, HCDR2 of SEQ ID NO: 3 and HCDR3 of SEQ ID NO: 66, or a variant thereof having 5 or fewer conservative amino acid substitutions in HCDR1, HCDR2, and/or HCDR3; and the VL region amino acid sequence comprises LCDR1 of SEQ ID NO: 5, LCDR2 of SEQ ID NO: 6 and LCDR3 of SEQ ID NO: 7, or a variant thereof having 5 or fewer conservative amino acid substitutions in LCDR1, LCDR2, and/or LCDR3;

(iv) the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3; and the VL region amino acid sequence comprises LCDR1 of SEQ ID NO: 69, LCDR2 of SEQ ID NO: 6 and LCDR3 of SEQ ID NO: 7, or a variant thereof having 5 or fewer conservative amino acid substitutions in LCDR1, LCDR2, and/or LCDR3; or (v) the VH region amino acid sequence comprises HCDR1 of SEQ ID NO: 14, HCDR2 of SEQ ID NO: 3 and HCDR3 of SEQ ID NO: 68, or a variant thereof having 5 or fewer conservative amino acid substitutions in HCDR1, HCDR2, and/or HCDR3; and the VL region amino acid sequence comprises LCDR1 of SEQ ID NO: 71, LCDR2 of SEQ ID NO: 6 and LCDR3 of SEQ ID NO: 7, or a variant thereof having 5 or fewer conservative amino acid substitutions in LCDR1, LCDR2, and/or LCDR3.

33. The antibody or the antibody fragment of embodiment 30, wherein the VH region amino acid sequence comprises (i) SEQ ID NO: 8, or an amino acid sequence that is at least 95%, 96%, 97%, 98% or 99% identical to the amino acid sequence of SEQ ID NO: 8;

(ii) SEQ ID NO: 16, or an amino acid sequence that is at least 95%, 96%, 97%, 98% or 99% identical to the amino acid sequence of SEQ ID NO: 16; or (iii) SEQ ID NO: 67, or an amino acid sequence that is at least 95%, 96%, 97%, 98% or 99% identical to the amino acid sequence of SEQ ID NO: 67.

34. The antibody or the antibody fragment of embodiment 31, wherein the VL region amino acid sequence comprises (i) SEQ ID NO: 9, or an amino acid sequence that is at least 95%, 96%, 97%, 98% or 99% identical to the amino acid sequence of SEQ ID NO: 9;

(ii) SEQ ID NO: 17, or an amino acid sequence that is at least 95%, 96%, 97%, 98% or 99% identical to the amino acid sequence of SEQ ID NO: 17;

(iii) SEQ ID NO: 70, or an amino acid sequence that is at least 95%, 96%, 97%, 98% or 99% identical to the amino acid sequence of SEQ ID NO: 70; or (iv) SEQ ID NO: 72, or an amino acid sequence that is at least 95%, 96%, 97%, 98% or 99% identical to the amino acid sequence of SEQ ID NO: 72.

35. The antibody or the antibody fragment of embodiment 32, wherein (i) the VH region amino acid sequence comprises SEQ ID NO: 8, or an amino acid sequence that is at least 95%, 96%, 97%, 98% or 99% identical to the amino acid sequence of SEQ ID NO: 8; and the VL region amino acid sequence comprises SEQ ID NO: 9, or an amino acid sequence that is at least 95%, 96%, 97%, 98% or 99% identical to the amino acid sequence of SEQ ID NO: 9;

(ii) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 17, or an amino acid sequence that is at least 95%, 96%, 97%, 98% or 99% identical to the amino acid sequence of SEQ ID NO: 17;

(iii) the VH region amino acid sequence comprises SEQ ID NO: 67, or an amino acid sequence that is at least 95%, 96%, 97%, 98% or 99% identical to the amino acid sequence of SEQ ID NO: 67; and the VL region amino acid sequence comprises SEQ ID NO: 17, or an amino acid sequence that is at least 95%, 96%, 97%, 98% or 99% identical to the amino acid sequence of SEQ ID NO: 17;

(iv) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 70, or an amino acid sequence that is at least 95%, 96%, 97%, 98% or 99% identical to the amino acid sequence of SEQ ID NO: 70; or (v) the VH region amino acid sequence comprises SEQ ID NO: 16, or an amino acid sequence that is at least 95%, 96%, 97%, 98% or 99% identical to the amino acid sequence of SEQ ID NO: 16; and the VL region amino acid sequence comprises SEQ ID NO: 72, or an amino acid sequence that is at least 95%, 96%, 97%, 98% or 99% identical to the amino acid sequence of SEQ ID NO: 72.

36. A monoclonal antibody that is an agonist of $\alpha7\beta1$ integrin, or an antibody fragment thereof, wherein the antibody comprises a heavy chain and a light chain,
(i) wherein the heavy chain amino acid sequence comprises SEQ ID NO: 18, and the light chain amino acid sequence comprises SEQ ID NO: 19;
(ii) wherein the heavy chain amino acid sequence comprises SEQ ID NO: 45, and the light chain amino acid sequence comprises SEQ ID NO: 53;
(iii) wherein the heavy chain amino acid sequence comprises SEQ ID NO: 18, and the light chain amino acid sequence comprises SEQ ID NO: 62; or
(iv) wherein the heavy chain amino acid sequence comprises SEQ ID NO: 18, and the light chain amino acid sequence comprises SEQ ID NO: 63.

37. The antibody or the antibody fragment of any one of embodiments 30-36, wherein the antibody or the antibody fragment binds specifically to $\alpha7$ protein.

38. The antibody or the antibody fragment of any one of embodiments 30-37, wherein the antibody or the antibody fragment binds specifically to an epitope of $\alpha7$ protein, the epitope of $\alpha7$ protein comprising, consisting essentially of, or consisting of the amino acid sequence of
(i) SEQ ID NO: 10;
(ii) 5-10, 10-15, 15-20, 20-25, 25-30, 30-35 or 35-40 amino acids of SEQ ID NO: 10; or
(iii) 5-10, 10-15, 15-20, 20-25, 25-30, 30-35 or 35-40 amino acids of SEQ ID NO: 24.

39. The pharmaceutical agent of any one of embodiments 1-18 or the antibody or the antibody fragment of any one of embodiments 19-38, wherein the $\alpha71$ integrin is human $\alpha7\beta1$ integrin.

40. The antibody fragment of any one of embodiments 19-39, wherein the antibody fragment is an Fab, an $F(ab')_2$, an Fab', an scFv, a single domain antibody, a diabody or a single chain camelid antibody.

41. An isolated nucleic acid molecule encoding the antibody or the antibody fragment of any one of embodiments 30-40.

42. An expression vector comprising the nucleic acid molecule of embodiment 41.

43. The expression vector of embodiment 42, wherein the nucleic acid molecule is operatively linked to regulatory sequences suitable for expression of the nucleic acid segment in a host cell.

44. A recombinant host cell comprising the expression vector of embodiment 42 or 43.

45. A method for producing an antibody or an antibody fragment that is an agonist of $\alpha7\beta1$ integrin, the method comprising: culturing a recombinant host cell comprising the expression vector of embodiment 42 or 43 under conditions effective to express the nucleic acid molecule to produce the antibody or the antibody fragment that is an agonist of $\alpha7\beta1$ integrin.

46. A pharmaceutical composition comprising: the pharmaceutical agent of any one of embodiments 1-18 or the antibody or the antibody fragment of any one of embodiments 19-40, and a pharmaceutically acceptable carrier, diluent or excipient.

47. The pharmaceutical composition of embodiment 46, further comprising an additional pharmaceutical agent that is an agonist of at least one of: $\alpha7\beta1$ integrin, $\alpha6\beta1$ integrin and $\alpha3\beta1$ integrin.

48. A method of treating a disorder or a disease in a subject, comprising administering to the subject a therapeutically effective amount of the pharmaceutical agent of any one of embodiments 1-19 or the antibody or the antibody fragment of any one of embodiments 19-40, thereby treating the disorder or the disease in the subject;
wherein the disorder or the disease is characterized by one or more of:
a malfunction of $\alpha7\beta1$ integrin in the subject;
a dystrophin deficiency in the subject;
a mutation in dystrophin in the subject;
non-functioning dystrophin in the subject; or
a muscle dysfunction other than $\alpha7\beta1$ malfunction, or dystrophin deficiency, mutation, or non-function.

49. The method of embodiment 48, wherein the muscle dysfunction is caused by or associated with one or more of: cancer, congestive heart failure, chronic obstructive pulmonary disease, chronic kidney disease, HIV infection/AIDS, anorexia nervosa, bulimia, malnutrition, exposure, nausea, type I diabetes, type II diabetes, metabolic syndrome, cachexia, anemia, heart failure, high blood pressure, rhabdomyolysis, sepsis, sarcopenia, physical inactivity, damage due to excess physical activity, hypothermia, hyperthermia, injury, denervation, amyotrophic lateral sclerosis, multiple sclerosis, spinal muscular atrophy, alcohol-associated myopathy, burn-associated myopathy, stroke, steroid therapy or the withdrawal of steroid therapy, dermatomyositis, Guillain-Barre syndrome, neuropathy, osteoarthritis, infection, polio, polymyositis, inflammation, rheumatoid arthritis, hypocholesterolemia, electrical injury, heat stroke, prolonged immobilization, lack of blood flow to a limb, or contact with venom.

50. The method of embodiment 48, wherein the disease is a muscle wasting disease.

51. The method of embodiment 50, wherein the muscle wasting disease is a muscular dystrophy.

52. The method of embodiment 51, wherein the muscular dystrophy is Duchenne muscular dystrophy (DMD), Becker muscular dystrophy, merosin-deficient congenital muscular dystrophy type 1A or limb-girdle muscular dystrophy.

53. The method of embodiment 49, further comprising identifying a subject having a muscle dysfunction.

54. The method of embodiment 50, further comprising identifying a subject having a muscle wasting disease.

55. The method of any one of embodiments 49-54, wherein the administering reverses, stabilizes or slows muscle wasting or muscle dysfunction in the subject.

56. The method of any one of embodiments 49-54, wherein the administering improves muscle function in the subject.

57. The method of any one of embodiments 49-54, wherein the administering does not worsen muscle function in the subject.

58. The method of any one of embodiments 49-54, further comprising measuring muscle function in the subject after the administration step, wherein the rate of worsening of muscle function is reduced.

59. The method of any one of embodiments 50-52 and 54, wherein administering to the subject the therapeutically effective amount of the pharmaceutical agent is effective to upregulate the activity and/or amount of α7β1 integrin in the subject effective to treat the malfunction of α7β1 integrin in the subject.

60. The method of any one of embodiments 50-52 and 54, wherein administering to the subject the therapeutically effective amount of the pharmaceutical agent is effective to upregulate activity and/or amount of α7β1 integrin in the subject, the upregulated activity and/or amount of α7β1 integrin in the subject being effective to at least in part mitigate the effect of at least one of: the dystrophin deficiency in the subject; the mutation in dystrophin in the subject; or the non-functioning dystrophin in the subject.

61. The method of any one of embodiments 49-54, wherein administering to the subject the therapeutically effective amount of the pharmaceutical agent is effective to mitigate muscle injury in the subject.

62. The method of any one of embodiments 49-54, wherein administering to the subject the therapeutically effective amount of the pharmaceutical agent is effective to mitigate eccentric muscle injury in the subject.

63. The method of any one of embodiments 49-54, wherein administering to the subject the therapeutically effective amount of the pharmaceutical agent is effective to improve diaphragm muscle function in the subject.

64. The method of any one of embodiments 49-54, further comprising administering to the subject one or more other therapies, the one or more other therapies directed to muscular dystrophy or muscle wasting.

65. The method of any one of embodiments 49-54, wherein the one or more other therapies comprises one or more of: an anticonvulsant; an immunosuppressant; an antibiotic; quinine; therapy for management of congestive heart failure; a gene replacement therapy; an exon skipping therapy; a nonsense suppression therapy; therapy using an engineered nuclease; cell therapy using muscle precursor cells or stem cells; upregulation of utrophin; an anti-inflammatory therapy; an antifibrotic therapy; a steroid therapy; a myostatin blocker; insulin growth factor; a phosphodiesterase-5 inhibitor; an ACE inhibitor; induction of angiogenesis through delivery of vascular endothelial growth factor (VEGF); downregulation of VEGF decoy-receptor type 1 (VEGFR-1 or Flt-1); physical therapy; occupational therapy; surgery; orthotic intervention; speech therapy; respiratory therapy; a pacemaker; and a respiratory assistance device.

66. A method of activating α7β1 integrin in a muscle cell of a subject, the method comprising: administering to the subject a therapeutically effective amount of the pharmaceutical agent of any one of embodiments 1-18 or the antibody or the antibody fragment of any one of embodiments 19-40, thereby activating α7β1 integrin in a muscle cell of the subject.

67. A method of enhancing binding of α7β1 integrin to its ligand in a muscle cell of a subject, the method comprising:
administering to the subject a therapeutically effective amount of the pharmaceutical agent of any one of embodiments 1-18 or the antibody or the antibody fragment of any one of embodiments 19-40, thereby enhancing binding of α7β1 integrin to its ligand in a muscle cell of the subject.

68. Use of the pharmaceutical agent of any one of embodiments 1-18 or the antibody or the antibody fragment of any one of embodiments 19-40 in the manufacture of a medicament for treating a disorder or a disease characterized by a malfunction of α7β1 integrin in a subject.

What is claimed is:

1. A monoclonal antibody or an antigen-binding fragment thereof that binds to α7β1 integrin, wherein the antibody or the antigen-binding fragment comprises a heavy chain variable (VH) region and a light chain variable (VL) region, wherein the VH region comprises three complementarity determining regions (HCDRs 1-3) and the VL region comprises three complementarity determining regions (LCDRs 1-3), and wherein the VH region comprises a HCDR1 comprising the amino acid sequence of SEQ ID NO: 14, a HCDR2 comprising the amino acid sequence of SEQ ID NO: 3 and a HCDR3 comprising the amino acid sequence of SEQ ID NO: 68; and the VL region comprises a LCDR1 comprising the amino acid sequence of SEQ ID NO: 71, a LCDR2 comprising the amino acid sequence of SEQ ID NO: 6 and a LCDR3 comprising the amino acid sequence of SEQ ID NO: 7.

2. The antibody or antigen-binding fragment of claim 1, wherein the antibody or antigen-binding fragment thereof is an agonist of α7β1 integrin.

3. The antibody or the antigen-binding fragment of claim 1, wherein the antibody or the antigen-binding fragment binds specifically to α7 protein.

4. The antibody or the antigen-binding fragment of claim 1, wherein the α7β1 integrin is human α7β1 integrin.

5. The antibody or antigen-binding fragment of claim 1, wherein the antigen-binding fragment is a Fab, a F(ab') 2, a Fab', an scFv, a single domain antibody, or a diabody.

6. The antibody or antigen-binding fragment of claim 1, wherein the antibody or antigen-binding fragment is humanized.

7. The antibody or antigen-binding fragment of claim 1, wherein the antibody or antigen-binding fragment comprises a constant region of an immunoglobulin (Ig) selected from IgG1, IgG2, IgG3, IgG4, IgA1, or IgA2.

8. The antibody or antigen-binding fragment of claim 7, wherein the antibody or antigen-binding fragment comprises a constant region of an IgG4.

9. The antibody or antigen-binding fragment of claim 1, wherein the antibody comprises a heavy chain and a light chain, wherein the heavy chain comprises a VH comprising the amino acid sequence of SEQ ID NO: 16 and the light chain comprises a VL comprising the amino acid sequence of SEQ ID NO: 72.

10. The antibody or antigen-binding fragment of claim 9, wherein the antibody or antigen-binding fragment is humanized.

11. The antibody or antigen-binding fragment of claim 9, wherein the antibody or antigen-binding fragment comprises a constant region of an immunoglobulin (Ig) selected from IgG1, IgG2, IgG3, IgG4, IgA1, or IgA2.

12. The antibody or antigen-binding fragment of claim 11, wherein the antibody or antigen-binding fragment comprises a constant region of an IgG4.

13. A pharmaceutical composition comprising:
the antibody or the antigen-binding fragment of claim 1, and
a pharmaceutically acceptable carrier, diluent or excipient.

14. The pharmaceutical composition of claim 13, further comprising an additional pharmaceutical agent that is an agonist of at least one of: α7β1 integrin, α6β1 integrin and α3β1 integrin.

15. A monoclonal antibody that is an agonist of α7β1 integrin, wherein the antibody comprises a heavy chain and a light chain, wherein the heavy chain comprises the amino acid sequence of SEQ ID NO: 18, and the light chain comprises the amino acid sequence of SEQ ID NO: 63.

* * * * *